United States Patent [19]
Hlavka et al.

[11] Patent Number: 5,840,683
[45] Date of Patent: Nov. 24, 1998

[54] PEPTIDES INHIBITING THE ONCOGENIC ACTION OF P21 RAS

[75] Inventors: Joseph J. Hlavka, Tuxedo Park; Matthew R. Pincus, Brooklyn; John Fowler Noble, Pomona, all of N.Y.; Henry Baxter Abajian, Hillsdale, N.J.; Andrew S. Kende, Pittsford, N.Y.

[73] Assignee: Innapharma, Inc., Upper Saddle River, N.J.

[21] Appl. No.: 531,525

[22] Filed: Sep. 21, 1995

[51] Int. Cl.$^6$ .............................. A61K 38/12; C07K 5/08
[52] U.S. Cl. .................... 514/9; 514/11; 514/14; 514/15; 514/16; 514/17; 514/18; 530/317; 530/326; 530/327; 530/328; 530/329; 530/330; 530/331
[58] Field of Search .............................. 514/9, 11, 14–18; 530/317, 326–331

[56] References Cited

U.S. PATENT DOCUMENTS

| | | | |
|---|---|---|---|
| 4,699,877 | 10/1987 | Cline et al. | 435/6 |
| 4,855,406 | 8/1989 | Yanaihara et al. | 530/324 |
| 5,364,851 | 11/1994 | Joran | 530/345 |

FOREIGN PATENT DOCUMENTS

| | | |
|---|---|---|
| 0 203 587 | 12/1986 | European Pat. Off. . |
| 2694296 | 2/1994 | France . |
| 93/21314 | 10/1993 | WIPO . |

OTHER PUBLICATIONS

Liwo et al., J. Prot. Chem. vol. 13 No. 2 (May/1994) pp. 237–251.

Dykes et al., J. Biomol. Struct. 9 Dyn. vol. 11 No. 3 (1993) pp. 443–458.

Lee et al., Med. Sci. Res. vol. 18 No. 19 (Oct. 1990) pp. 771–772.

Spatola et al., "Chemistry & Biochemistry of Amino Acids, Peptides and Proteins", vol. 7 (Weinstein Ed. Marcell Dekkea 1953) 284–285; 344–45.

Science, vol. 256 (Apr./1992) p. 441.

Liwo et al., Embase Abstract No. 94142373 (1994).

Dykes et al., Embase Absrac No. 94032058 (1993).

Kohl et al. (1993) Science 260:1934–1937.

James et al. (1993) Science 260:1937–1942.

Chung et al. (1991) Anticancer Res. 11:1373–1378.

Chung et al. (1992) Exp. Cell Res. 203:329–335.

Hu et al. (1995) Science 268:100–102.

Pincus et al. (1992) Ann. Clin. Lab. Sci. U.S. 22:323–342.

Chung et al. (1991) Biochem. Biophys. Res. Comm. 181:1378–1384.

Haspel et al. (1992) Med. Sci. Res. 20:809–811.

Yamasaki et al. (1994) Biochemistry 33:65–73.

*Primary Examiner*—Cecilia J. Tsang
*Assistant Examiner*—Bennett Celsa
*Attorney, Agent, or Firm*—Greenlee, Winner and Sullivan, PC

[57] ABSTRACT

The present invention provides peptides and cyclized peptides which inhibit the oncogenic and/or transforming activity of the p21 ras protein, pharmaceutical compositions containing at least one of the ras-inhibiting peptides, cyclized peptides and peptidomimetics, and methods for inhibiting the ras-mediated oncogenic and/or transformation process in mammalian cells or tissues.

10 Claims, No Drawings

SEQUENCE LISTING ( 1 ) GENERAL INFORMATION:

( i i i ) NUMBER OF SEQUENCES: 52

( 2 ) INFORMATION FOR SEQ ID NO:1:

( i ) SEQUENCE CHARACTERISTICS:
      ( A ) LENGTH: 6 amino acids
      ( B ) TYPE: amino acid
      ( C ) STRANDEDNESS:
      ( D ) TOPOLOGY: linear ( i i ) MOLECULE TYPE: peptide ( i i i ) HYPOTHETICAL: NO ( x i ) SEQUENCE DESCRIPTION: SEQ ID NO:1:

Ile  Lys  Arg  Val  Lys  Asp
   1                       5

( 2 ) INFORMATION FOR SEQ ID NO:2:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( x i ) SEQUENCE DESCRIPTION: SEQ ID NO:2:

Lys  Cys  Asp  Leu  Ala
   1                  5

( 2 ) INFORMATION FOR SEQ ID NO:3:

( i ) SEQUENCE CHARACTERISTICS:
      ( A ) LENGTH: 7 amino acids
      ( B ) TYPE: amino acid
      ( C ) STRANDEDNESS:
      ( D ) TOPOLOGY: linear ( i i ) MOLECULE TYPE: peptide ( i i i ) HYPOTHETICAL: NO ( x i ) SEQUENCE DESCRIPTION: SEQ ID NO:3:

Cys  Asp  Leu  Ala  Ala  Arg  Thr
   1                       5

( 2 ) INFORMATION FOR SEQ ID NO:4:

( i ) SEQUENCE CHARACTERISTICS:
      ( A ) LENGTH: 4 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( x i ) SEQUENCE DESCRIPTION: SEQ ID NO:4:

Asp  Leu  Ala  Ala
   1

( 2 ) INFORMATION FOR SEQ ID NO:5:

( i ) SEQUENCE CHARACTERISTICS:
        ( A ) LENGTH: 188 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:5:

```
Met Thr Glu Tyr Lys Leu Val Val Val Gly Ala Gly Gly Val Gly Lys
 1               5                  10                      15

Ser Ala Leu Thr Ile Gln Leu Ile Gln Asn His Phe Val Asp Glu Tyr
            20              25                      30

Asp Pro Thr Ile Glu Asp Ser Tyr Arg Lys Gln Val Val Ile Asp Gly
            35              40              45

Glu Thr Cys Leu Leu Asp Ile Leu Asp Thr Ala Gly Gln Glu Glu Tyr
    50              55              60

Ser Ala Met Arg Asp Gln Tyr Met Arg Thr Gly Glu Gly Phe Leu Cys
65              70              75                      80

Val Phe Ala Ile Asn Asn Thr Lys Ser Phe Glu Asp Ile His Gln Tyr
                85              90                      95

Arg Glu Gln Ile Lys Arg Val Lys Asp Ser Asp Val Pro Met Val
                100             105             110

Leu Val Gly Asn Lys Cys Asp Leu Ala Ala Thr Val Glu Ser Arg Gln
            115             120             125

Ala Gln Asp Leu Ala Arg Ser Tyr Gly Ile Pro Tyr Ile Glu Thr Ser
    130             135             140

Ala Lys Thr Arg Gln Gly Val Glu Asp Ala Phe Tyr Thr Leu Val Arg
145             150             155             160

Glu Ile Arg Gln His Lys Leu Arg Lys Leu Asn Pro Pro Asp Glu Ser
                165             170             175

Gly Pro Gly Cys Met Ser Cys Lys Cys Val Leu Ser
            180             185
```

( 2 ) INFORMATION FOR SEQ ID NO:6:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( x i ) SEQUENCE DESCRIPTION: SEQ ID NO:6:

```
Thr Ile Glu Asp Ser Tyr Arg Lys Gln Val Val Ile Asp
 1               5                  10
```

( 2 ) INFORMATION FOR SEQ ID NO:7:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( x i ) SEQUENCE DESCRIPTION: SEQ ID NO:7:

Tyr Arg Glu Gln Ile Lys Arg Val Lys Asp Ser Asp Asp Val Pro
1               5                   10                  15

( 2 ) INFORMATION FOR SEQ ID NO:8:

( i ) SEQUENCE CHARACTERISTICS:
      ( A ) LENGTH: 12 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( x i ) SEQUENCE DESCRIPTION: SEQ ID NO:8:

Gly Asn Lys Cys Asp Leu Ala Ala Arg Thr Val Glu
1               5                   10

( 2 ) INFORMATION FOR SEQ ID NO:9:

( i ) SEQUENCE CHARACTERISTICS:
      ( A ) LENGTH: 7 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( x i ) SEQUENCE DESCRIPTION: SEQ ID NO:9:

Cys Asp Leu Ala Ala Arg Thr
1               5

( 2 ) INFORMATION FOR SEQ ID NO:10:

( i ) SEQUENCE CHARACTERISTICS:
      ( A ) LENGTH: 215 amino acids
      ( B ) TYPE: amino acid
      ( C ) STRANDEDNESS: single
      ( D ) TOPOLOGY: linear ( i i ) MOLECULE TYPE: protein ( i i i ) HYPOTHETICAL: NO ( v i ) ORIGINAL SOURCE:
      ( A ) ORGANISM: Arabidopsis thaliana ( x i ) SEQUENCE DESCRIPTION: SEQ ID NO:10:

Met Ala Ala Pro Pro Ala Arg Ala Arg Ala Asp Tyr Asp Tyr Leu Ile
1               5                   10                  15

Lys Leu Leu Leu Ile Gly Asp Ser Gly Val Gly Lys Ser Cys Leu Leu
                20                  25                  30

Leu Arg Phe Ser Asp Gly Ser Phe Thr Thr Ser Phe Ile Thr Thr Ile
            35                  40                  45

Gly Ile Asp Phe Lys Ile Arg Thr Ile Glu Leu Asp Gly Lys Arg Ile
        50                  55                  60

Lys Leu Gln Ile Trp Asp Thr Ala Gly Gln Glu Arg Arg Thr Ile Thr
65                  70                  75                  80

Thr Ala Tyr Tyr Arg Gly Ala Met Gly Ile Leu Leu Val Tyr Asp Val
                85                  90                  95

Thr Asp Glu Ser Ser Phe Asn Asn Ile Arg Asn Trp Ile Arg Asn Ile
                100                 105                 110

5,840,683

-continued

```
Glu  Gln  His  Ala  Ser  Asp  Asn  Val  Asn  Lys  Ile  Leu  Val  Gly  Asn  Lys
          115                      120                      125

Ala  Asp  Met  Asp  Glu  Ser  Lys  Arg  Ala  Val  Pro  Thr  Ala  Lys  Gly  Gln
     130                      135                      140

Ala  Leu  Ala  Asp  Glu  Tyr  Gly  Ile  Lys  Phe  Phe  Glu  Thr  Ser  Ala  Lys
145                      150                      155                      160

Thr  Asn  Leu  Asn  Val  Glu  Glu  Val  Phe  Phe  Ser  Ile  Gly  Arg  Asp  Ile
                    165                      170                      175

Lys  Gln  Arg  Leu  Ser  Asp  Thr  Asp  Ser  Arg  Ala  Glu  Pro  Ala  Thr  Ile
               180                      185                      190

Lys  Ile  Ser  Gln  Thr  Asp  Gln  Ala  Ala  Gly  Ala  Gly  Gln  Ala  Thr  Gln
          195                      200                      205

Lys  Ser  Ala  Cys  Cys  Gly  Thr
     210                      215
```

( 2 ) INFORMATION FOR SEQ ID NO:11:

( i ) SEQUENCE CHARACTERISTICS:
( A ) LENGTH: 213 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( v i ) ORIGINAL SOURCE:
( A ) ORGANISM: Arabidopsis thaliana ( x i ) SEQUENCE DESCRIPTION: SEQ ID NO:11:

```
Met  Ala  Gly  Tyr  Ala  Asp  Glu  Glu  Tyr  Asp  Tyr  Leu  Phe  Lys  Leu  Val
1                   5                        10                       15

Leu  Ile  Gly  Asp  Ser  Gly  Val  Gly  Lys  Ser  Asn  Leu  Leu  Ser  Arg  Phe
               20                       25                       30

Thr  Lys  Asn  Phe  Asn  Leu  Glu  Ser  Lys  Ser  Thr  Ile  Gly  Val  Glu  Phe
          35                       40                       45

Ala  Thr  Lys  Thr  Thr  Lys  Val  Glu  Gly  Lys  Val  Val  Lys  Ala  Gln  Ile
     50                       55                       60

Trp  Asp  Thr  Ala  Gly  Gln  Glu  Arg  Tyr  Arg  Ala  Ile  Thr  Ser  Ala  Tyr
65                       70                       75                       80

Tyr  Arg  Gly  Ala  Val  Gly  Ala  Leu  Leu  Ile  Tyr  Asp  Val  Thr  Arg  His
               85                       90                       95

Ala  Thr  Phe  Glu  Asn  Ala  Ala  Arg  Trp  Leu  Arg  Glu  Leu  Arg  Gly  His
               100                      105                      110

Thr  Asp  Pro  Asn  Ile  Val  Val  Met  Leu  Ile  Gly  Asn  Lys  Cys  Asp  Leu
          115                      120                      125

Arg  His  Leu  Val  Ala  Val  Lys  Thr  Glu  Glu  Ala  Lys  Ala  Phe  Ala  Glu
     130                      135                      140

Arg  Glu  Ser  Leu  Tyr  Phe  Met  Glu  Thr  Ser  Ala  Leu  Asp  Ala  Thr  Asn
145                      150                      155                      160

Val  Glu  Asn  Ala  Phe  Thr  Glu  Val  Leu  Thr  Gln  Ile  His  Lys  Ile  Val
                    165                      170                      175

Ser  Lys  Arg  Ser  Val  Asp  Gly  Gly  Ser  Ala  Asp  Leu  Pro  Gly  Lys
               180                      185                      190

Gly  Glu  Thr  Ile  Asn  Val  Lys  Glu  Asp  Gly  Ser  Val  Leu  Lys  Arg  Met
          195                      200                      205

Gly  Cys  Cys  Ser  Asn
```

5,840,683

37

38

-continued 2 1 0

( 2 ) INFORMATION FOR SEQ ID NO:12:

( i ) SEQUENCE CHARACTERISTICS:
        ( A ) LENGTH: 213 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Arabidopsis thaliana ( x i ) SEQUENCE DESCRIPTION: SEQ ID NO:12:

```
Met Ser Ser Asp Asp Glu Gly Arg Glu Glu Tyr Phe Lys Ile Val Val
 1               5                  10                  15

Ile Gly Asp Ser Ala Val Gly Lys Ser Asn Leu Leu Ser Arg Tyr Ala
                20                  25                  30

Arg Asn Glu Phe Ser Ala Asn Ser Lys Ala Thr Ile Gly Val Glu Phe
            35                  40                  45

Gln Thr Gln Ser Met Ile Glu Gly Lys Glu Val Lys Ala Gln Ile Trp
        50                  55                  60

Asp Thr Ala Gly Gln Glu Phe Arg Ala Val Thr Ser Tyr Tyr Arg Gly
65                  70                  75                  80

Ala Val Gly Ala Leu Val Val Tyr Asp Ile Thr Arg Arg Thr Thr Phe
                85                  90                  95

Glu Ser Val Gly Arg Trp Leu Asp Glu Leu Lys Ile His Ser Asp Thr
               100                 105                 110

Thr Val Ala Arg Met Leu Val Gly Asn Lys Cys Asp Leu Glu Asn Ile
            115                 120                 125

Arg Ala Val Ser Val Glu Glu Gly Lys Ala Leu Ala Glu Glu Glu Gly
        130                 135                 140

Leu Phe Phe Val Glu Thr Ser Ala Leu Asp Ser Thr Asn Val Lys Thr
145                 150                 155                 160

Ala Phe Glu Met Val Ile Leu Asp Ile Tyr Asn Asn Val Ser Arg Lys
                165                 170                 175

Gln Leu Asn Ser Asp Thr Tyr Lys Asp Glu Leu Thr Val Arg Val Ser
            180                 185                 190

Leu Val Lys Asp Asp Asn Ser Ala Ser Lys Gln Ser Ser Gly Phe Ser
        195                 200                 205

Cys Cys Ser Ser Thr
        210
```

( 2 ) INFORMATION FOR SEQ ID NO:13:

( i ) SEQUENCE CHARACTERISTICS:
        ( A ) LENGTH: 201 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Discopyge ommata ( x i ) SEQUENCE DESCRIPTION: SEQ ID NO:13:

| Met | Asn | Pro | Glu | Tyr | Asp | Tyr | Leu | Phe | Lys | Leu | Leu | Leu | Ile | Gly | Asp |
| 1 | | | | 5 | | | | | 10 | | | | | | 15 |

| Ser | Gly | Val | Gly | Lys | Ser | Cys | Leu | Leu | Leu | Arg | Phe | Ala | Asp | Asp | Thr |
| | | | 20 | | | | | 25 | | | | | 30 | | |

| Tyr | Thr | Glu | Ser | Tyr | Ile | Ser | Thr | Ile | Gly | Val | Asp | Phe | Lys | Ile | Arg |
| | | 35 | | | | | 40 | | | | | 45 | | | |

| Thr | Ile | Glu | Leu | Asp | Gly | Lys | Thr | Ile | Lys | Leu | Gln | Ile | Trp | Asp | Thr |
| | 50 | | | | | 55 | | | | | 60 | | | | |

| Ala | Gly | Gln | Glu | Arg | Phe | Arg | Thr | Ile | Thr | Ser | Ser | Tyr | Tyr | Arg | Gly |
| 65 | | | | | 70 | | | | | 75 | | | | | 80 |

| Ala | His | Gly | Ile | Ile | Val | Val | Tyr | Asp | Val | Thr | Asp | Gln | Glu | Ser | Phe |
| | | | | 85 | | | | | 90 | | | | | 95 | |

| Asn | Asn | Val | Lys | Gln | Trp | Leu | Gln | Glu | Ile | Asp | Arg | Tyr | Ala | Ser | Glu |
| | | | 100 | | | | | 105 | | | | | 110 | | |

| Asn | Val | Asn | Lys | Leu | Leu | Val | Gly | Asn | Lys | Cys | Asp | Leu | Thr | Thr | Lys |
| | | 115 | | | | | 120 | | | | | 125 | | | |

| Lys | Val | Val | Asp | Tyr | Thr | Thr | Lys | Glu | Phe | Ala | Asp | Ser | Leu | Gly | Ile |
| | 130 | | | | | 135 | | | | | 140 | | | | |

| Pro | Phe | Leu | Glu | Thr | Ser | Ala | Lys | Asn | Ala | Thr | Asn | Val | Glu | Gln | Ala |
| 145 | | | | | 150 | | | | | 155 | | | | | 160 |

| Phe | Met | Thr | Met | Ala | Ala | Glu | Ile | Lys | Lys | Arg | Met | Gly | Pro | Gly | Ala |
| | | | | 165 | | | | | 170 | | | | | 175 | |

| Thr | Ser | Gly | Gly | Ser | Glu | Lys | Ser | Asn | Val | Asn | Ile | Gln | Ser | Thr | Pro |
| | | | 180 | | | | | 185 | | | | | 190 | | |

| Val | Lys | Ser | Ser | Gly | Gly | Gly | Cys | Cys | | | | | | | |
| | | 195 | | | | | 200 | | | | | | | | |

( 2 ) INFORMATION FOR SEQ ID NO:14:

( i ) SEQUENCE CHARACTERISTICS:
        ( A ) LENGTH: 202 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Lymnea stagnalis ( x i ) SEQUENCE DESCRIPTION: SEQ ID NO:14:

| Met | Ser | Thr | Met | Asn | Pro | Asp | Tyr | Asp | Tyr | Leu | Phe | Lys | Leu | Leu | Leu |
| 1 | | | | 5 | | | | | 10 | | | | | | 15 |

| Ile | Gly | Asp | Ser | Gly | Val | Gly | Lys | Ser | Cys | Leu | Leu | Leu | Arg | Phe | Ala |
| | | | 20 | | | | | 25 | | | | | 30 | | |

| Asp | Asp | Thr | Tyr | Thr | Glu | Ser | Tyr | Ile | Ser | Thr | Ile | Gly | Val | Asp | Phe |
| | | 35 | | | | | 40 | | | | | 45 | | | |

| Lys | Ile | Arg | Thr | Ile | Glu | Leu | Asp | Gly | Lys | Thr | Ile | Lys | Leu | Gln | Ile |
| | 50 | | | | | 55 | | | | | 60 | | | | |

| Trp | Asp | Thr | Ala | Gly | Gln | Glu | Arg | Phe | Arg | Thr | Ile | Thr | Ser | Ser | Tyr |
| 65 | | | | | 70 | | | | | 75 | | | | | 80 |

| Tyr | Arg | Gly | Ala | His | Gly | Ile | Ile | Val | Val | Tyr | Asp | Val | Thr | Asp | Gln |
| | | | | 85 | | | | | 90 | | | | | 95 | |

| Glu | Ser | Phe | Asn | Asn | Val | Lys | Gln | Trp | Leu | Gln | Glu | Ile | Asp | Arg | Tyr |
| | | | 100 | | | | | 105 | | | | | 110 | | |

| Ala | Ser | Glu | Asn | Val | Asn | Lys | Leu | Leu | Val | Gly | Asn | Lys | Ser | Asp | Leu |
| | | 115 | | | | | 120 | | | | | 125 | | | |

|   |   |   |   |   |   |   |   |   |   |   |   |   |   |   |
|---|---|---|---|---|---|---|---|---|---|---|---|---|---|---|
| Thr | Thr 130 | Lys | Lys | Val | Asp | Phe 135 | Thr | Thr | Ala | Lys 140 | Glu | Tyr | Ala | Asp | Gln |
| Leu 145 | Gly | Ile | Pro | Phe | Leu 150 | Glu | Thr | Ser | Ala | Lys 155 | Asn | Ala | Thr | Asn | Val 160 |
| Glu | Gln | Ala | Phe | Met 165 | Thr | Met | Ala | Ala | Glu 170 | Ile | Lys | Asn | Arg | Met 175 | Gly |
| Pro | Ile | Thr | Ala 180 | Ser | Asp | Ser | Lys | Pro 185 | Ser | Val | Lys | Ile | Asn 190 | Ser | Ser |
| Thr 195 | Pro | Ser | Ala | Asn | Lys | Gly | Gly 200 | Cys | Cys |

( 2 ) INFORMATION FOR SEQ ID NO:15:

( i ) SEQUENCE CHARACTERISTICS:
        ( A ) LENGTH: 208 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:15:

|   |   |   |   |   |   |   |   |   |   |   |   |   |   |   |   |
|---|---|---|---|---|---|---|---|---|---|---|---|---|---|---|---|
| Met 1 | Ala | Tyr | Ala | Tyr 5 | Leu | Phe | Lys | Tyr | Ile 10 | Ile | Ile | Gly | Asp | Thr 15 | Gly |
| Val | Gly | Lys | Ser 20 | Cys | Leu | Leu | Leu | Gln 25 | Phe | Thr | Asp | Lys | Arg 30 | Phe | Gln |
| Pro | Val | His 35 | Asp | Leu | Thr | Ile | Gly 40 | Val | Glu | Phe | Gly | Ala 45 | Arg | Met | Ile |
| Thr | Ile 50 | Asp | Gly | Lys | Gln | Ile 55 | Lys | Leu | Gln | Ile | Trp 60 | Asp | Thr | Ala | Gly |
| Gln 65 | Glu | Ser | Phe | Arg | Ser 70 | Ile | Thr | Arg | Ser | Tyr 75 | Tyr | Arg | Gly | Ala | Ala 80 |
| Gly | Ala | Leu | Leu | Val 85 | Tyr | Asp | Ile | Thr | Arg 90 | Arg | Asp | Thr | Phe | Asn 95 | His |
| Leu | Thr | Thr | Trp 100 | Leu | Glu | Asp | Ala | Arg 105 | Gln | His | Ser | Asn | Ser 110 | Asn | Met |
| Val | Ile | Met 115 | Leu | Ile | Gly | Asn | Lys 120 | Ser | Asp | Leu | Glu | Arg 125 | Arg | Glu | Val |
| Lys | Lys 130 | Glu | Glu | Gly | Glu | Ala 135 | Phe | Ala | Glu | His | Gly 140 | Leu | Ile | Phe | Met |
| Glu 145 | Thr | Ala | Lys | Thr | Ala 150 | Ser | Val | Glu | Glu | Ala 155 | Phe | Ile | Asn | Thr 160 | Ala |
| Lys | Glu | Ile | Tyr | Glu 165 | Lys | Ile | Gln | Glu | Gly 170 | Val | Phe | Asp | Ile | Asn 175 | Asn |
| Glu | Ala | Asn | Gly 180 | Ile | Lys | Ile | Gly | Pro 185 | Gln | His | Ala | Ala | Thr 190 | Asn | Ala |
| Thr | His | Ala 195 | Gly | Asn | Gln | Gly | Gly 200 | Gln | Gln | Ala | Gly | Gly 205 | Gly | Cys | Cys |

( 2 ) INFORMATION FOR SEQ ID NO:16:

( i ) SEQUENCE CHARACTERISTICS:
        ( A ) LENGTH: 210 amino acids
        ( B ) TYPE: amino acid
        ( C ) STRANDEDNESS: single (D) TOPOLOGY: linear (i i) MOLECULE TYPE: protein (i i i) HYPOTHETICAL: NO (v i) ORIGINAL SOURCE:
    (A) ORGANISM: Lymnea stagnalis (x i) SEQUENCE DESCRIPTION: SEQ ID NO:16:

| Met | Ser | Tyr | Ala | Tyr | Leu | Phe | Lys | Tyr | Ile | Ile | Ile | Gly | Asp | Thr | Gly |
|---|---|---|---|---|---|---|---|---|---|---|---|---|---|---|---|
| 1 | | | | 5 | | | | | 10 | | | | | 15 | |
| Val | Gly | Lys | Ser | Cys | Leu | Leu | Leu | Gln | Phe | Thr | Asp | Lys | Arg | Phe | Gln |
| | | | 20 | | | | | 25 | | | | | 30 | | |
| Pro | Val | His | Asp | Leu | Thr | Ile | Gly | Val | Glu | Phe | Gly | Ala | Arg | Met | Ile |
| | | | 35 | | | | 40 | | | | | 45 | | | |
| Thr | Ile | Asp | Gly | Lys | Gln | Ile | Lys | Leu | Gln | Ile | Trp | Asp | Thr | Ala | Gly |
| | 50 | | | | | 55 | | | | | 60 | | | | |
| Gln | Glu | Ser | Phe | Arg | Ser | Ile | Thr | Arg | Ser | Tyr | Tyr | Arg | Gly | Ala | Ala |
| 65 | | | | | 70 | | | | | 75 | | | | | 80 |
| Gly | Ala | Leu | Leu | Val | Tyr | Asp | Ile | Thr | Arg | Arg | Asp | Thr | Phe | Asn | His |
| | | | | 85 | | | | | 90 | | | | | 95 | |
| Leu | Thr | Thr | Trp | Leu | Glu | Asp | Ala | Arg | Gln | His | Ser | Asn | Ser | Asn | Met |
| | | | 100 | | | | | 105 | | | | | 110 | | |
| Val | Ile | Met | Leu | Ile | Gly | Asn | Lys | Ser | Asp | Leu | Glu | Ala | Arg | Arg | Val |
| | | 115 | | | | | 120 | | | | | 125 | | | |
| Lys | Lys | Glu | Glu | Gly | Glu | Ala | Phe | Arg | Glu | His | Gly | Leu | Ile | Phe | Met |
| | 130 | | | | | 135 | | | | | 140 | | | | |
| Glu | Thr | Ser | Ala | Lys | Thr | Ala | Ala | Asn | Val | Glu | Glu | Ala | Phe | Ile | Asn |
| 145 | | | | | 150 | | | | | 155 | | | | | 160 |
| Thr | Ala | Lys | Glu | Ile | Tyr | Gln | Lys | Ile | Gln | Asp | Gly | Val | Phe | Asp | Ile |
| | | | | 165 | | | | | 170 | | | | | 175 | |
| Asn | Asn | Glu | Ala | Asn | Gly | Ile | Lys | Ile | Gly | Pro | Gln | His | Ser | Pro | Ala |
| | | | 180 | | | | | 185 | | | | | 190 | | |
| Ser | Gln | Ser | Leu | Asn | Val | Gly | Gly | Ser | Gly | Gly | Asn | Gln | Gly | Gly | Asn |
| | | 195 | | | | | 200 | | | | | 205 | | | |
| Cys | Cys | | | | | | | | | | | | | | |
| | 210 | | | | | | | | | | | | | | |

(2) INFORMATION FOR SEQ ID NO:17:

(i) SEQUENCE CHARACTERISTICS:
    (A) LENGTH: 208 amino acids
    (B) TYPE: amino acid
    (C) STRANDEDNESS: single
    (D) TOPOLOGY: linear (i i) MOLECULE TYPE: protein (i i i) HYPOTHETICAL: NO (v i) ORIGINAL SOURCE:
    (A) ORGANISM: Oryctolagus cuniculus (x i) SEQUENCE DESCRIPTION: SEQ ID NO:17:

| Met | Ala | Tyr | Ala | Tyr | Leu | Phe | Lys | Tyr | Ile | Ile | Ile | Gly | Asp | Thr | Gly |
|---|---|---|---|---|---|---|---|---|---|---|---|---|---|---|---|
| 1 | | | | 5 | | | | | 10 | | | | | 15 | |
| Val | Gly | Lys | Ser | Cys | Leu | Leu | Leu | Gln | Phe | Thr | Asp | Lys | Arg | Phe | Gln |
| | | | 20 | | | | | 25 | | | | | 30 | | |
| Pro | Val | His | Asp | Leu | Thr | Ile | Gly | Val | Glu | Phe | Gly | Ala | Arg | Met | Ile |
| | | | 35 | | | | 40 | | | | | 45 | | | |

```
        Thr  Ile  Asp  Gly  Lys  Gln  Ile  Lys  Leu  Gln  Ile  Trp  Asp  Thr  Ala  Gln
              50                      55                            60

Glu  Ser  Phe  Arg  Ser  Ile  Arg  Ser  Tyr  Tyr  Arg  Gly  Ala  Gly  Ala  Leu
        65                       70                       75                           80

Leu  Val  Tyr  Asp  Ile  Thr  Arg  Arg  Asp  Phe  Asn  His  Leu  Thr  Thr
                        85                            90                       95

Trp  Leu  Glu  Asp  Ala  Arg  Gln  His  Ser  Asn  Ser  Asn  Met  Val  Ile  Met
                       100                      105                      110

Leu  Ile  Gly  Asn  Lys  Ser  Asp  Leu  Glu  Ser  Arg  Arg  Glu  Val  Lys  Lys
                       115                      120                      125

Glu  Glu  Gly  Glu  Ala  Phe  Ala  Arg  Glu  His  Gly  Leu  Ile  Phe  Met  Glu
                  130                      135                      140

Thr  Ser  Ala  Lys  Thr  Ala  Ser  Asn  Val  Glu  Glu  Ala  Phe  Ile  Asn  Thr
        145                           150                      155                      160

Ala  Lys  Glu  Ile  Tyr  Glu  Lys  Ile  Gln  Glu  Gly  Val  Phe  Asp  Ile  Asn
                             165                      170                      175

Asn  Glu  Ala  Asn  Gly  Ile  Lys  Ile  Gly  Pro  Gln  His  Gly  Ala  Thr  Asn
                        180                      185                      190

Ala  His  Ala  Gly  Asn  Gln  Gly  Gly  Gln  Gln  Ala  Gly  Gly  Gly  Cys  Cys
                        195                      200                      205
```

( 2 ) INFORMATION FOR SEQ ID NO:18:

( i ) SEQUENCE CHARACTERISTICS:
        ( A ) LENGTH: 212 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Rattus norvegicus ( x i ) SEQUENCE DESCRIPTION: SEQ ID NO:18:

```
        Met  Ala  Tyr  Ala  Tyr  Leu  Phe  Lys  Tyr  Ile  Ile  Ile  Gly  Asp  Thr  Gly
        1                        5                       10                           15

Val  Gly  Lys  Ser  Cys  Leu  Leu  Leu  Gln  Phe  Thr  Asp  Lys  Arg  Phe  Gln
                       20                       25                            30

Pro  Val  His  Asp  Leu  Thr  Met  Gly  Val  Glu  Phe  Gly  Ala  Arg  Met  Ile
                        35                       40                            45

Thr  Ile  Asp  Gly  Lys  Gln  Ile  Lys  Leu  Gln  Ile  Trp  Asp  Thr  Ala  Gly
                       50                       55                            60

Gln  Glu  Ser  Phe  Arg  Ser  Ile  Thr  Arg  Ser  Tyr  Tyr  Arg  Gly  Ala  Ala
        65                       70                           75                       80

Gly  Ala  Leu  Leu  Val  Tyr  Asp  Ile  Thr  Arg  Arg  Asp  Thr  Phe  Asn  His
                             85                            90                       95

Leu  Thr  Thr  Trp  Leu  Glu  Asp  Ala  Arg  Gln  His  Ser  Asn  Ser  Asn  Met
                            100                      105                      110

Val  Ile  Met  Leu  Ile  Gly  Asn  Lys  Ser  Asp  Leu  Glu  Ser  Arg  Arg  Glu
                       115                      120                      125

Val  Lys  Lys  Glu  Glu  Gly  Glu  Ala  Phe  Ala  Arg  Glu  His  Gly  Leu  Ile
                       130                      135                      140

Phe  Met  Glu  Thr  Ser  Ala  Lys  Thr  Ala  Ser  Asn  Val  Glu  Glu  Ala  Phe
        145                           150                      155                      160

Ile  Asn  Thr  Ala  Lys  Glu  Ile  Tyr  Glu  Lys  Ile  Gln  Glu  Gly  Val  Phe
                             165                      170                      175
```

|  |  |  |  |  |  |  |  |  |  |  |  |  |  |
|---|---|---|---|---|---|---|---|---|---|---|---|---|---|
| Asp | Ile | Asn | Asn | Glu | Ala | Asn | Gly | Ile | Lys | Ile | Gly | Pro | Gln | His | Ala |
|  |  |  | 180 |  |  |  |  | 185 |  |  |  |  | 190 |
| Ala | Thr | Asn | Ala | Ser | His | Gly | Gly | Asn | Gln | Gly | Gly | Gln | Gln | Ala | Gly |
|  |  | 195 |  |  |  |  | 200 |  |  |  |  | 205 |
| Gly | Gly | Cys | Cys |
|  |  | 210 |

( 2 ) INFORMATION FOR SEQ ID NO:19:

( i ) SEQUENCE CHARACTERISTICS:
        ( A ) LENGTH: 218 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Drosophila melanogaster ( x i ) SEQUENCE DESCRIPTION: SEQ ID NO:19:

| Met | Ala | Gly | Gly | Asp | Pro | Lys | Trp | Gln | Lys | Asp | Ala | Ala | Asp | Gln | Asn |
|---|---|---|---|---|---|---|---|---|---|---|---|---|---|---|---|
| 1 |  |  |  | 5 |  |  |  |  | 10 |  |  |  |  | 15 |  |
| Phe | Asp | Tyr | Met | Phe | Lys | Leu | Leu | Ile | Ile | Gly | Asn | Ser | Ser | Val | Gly |
|  |  |  | 20 |  |  |  |  | 25 |  |  |  |  | 30 |
| Lys | Thr | Ser | Phe | Leu | Phe | Arg | Tyr | Ala | Asp | Asp | Ser | Phe | Thr | Ser | Ala |
|  |  | 35 |  |  |  |  | 40 |  |  |  |  | 45 |
| Phe | Val | Ser | Thr | Val | Gly | Ile | Asp | Phe | Lys | Val | Lys | Thr | Val | Phe | Arg |
|  | 50 |  |  |  |  | 55 |  |  |  |  | 60 |
| His | Asp | Lys | Arg | Val | Lys | Leu | Gln | Ile | Trp | Asp | Thr | Ala | Gly | Gln | Glu |
| 65 |  |  |  | 70 |  |  |  |  | 75 |  |  |  |  | 80 |
| Arg | Tyr | Arg | Thr | Ile | Thr | Thr | Ala | Tyr | Tyr | Arg | Gly | Ala | Met | Gly | Phe |
|  |  |  |  | 85 |  |  |  |  | 90 |  |  |  |  | 95 |
| Ile | Leu | Met | Tyr | Asp | Val | Thr | Asn | Glu | Asp | Ser | Phe | Asn | Ser | Val | Gln |
|  |  |  | 100 |  |  |  |  | 105 |  |  |  |  | 110 |
| Asp | Trp | Val | Thr | Gln | Ile | Lys | Thr | Tyr | Ser | Trp | Asp | Asn | Ala | Gln | Val |
|  |  | 115 |  |  |  |  | 120 |  |  |  |  | 125 |
| Ile | Leu | Val | Gly | Asn | Lys | Cys | Asp | Met | Glu | Asp | Gln | Arg | Val | Ile | Ser |
|  | 130 |  |  |  |  | 135 |  |  |  |  | 140 |
| Phe | Glu | Arg | Gly | Arg | Gln | Leu | Ala | Asp | Gln | Leu | Gly | Val | Glu | Phe | Phe |
| 145 |  |  |  |  | 150 |  |  |  |  | 155 |  |  |  |  | 160 |
| Glu | Thr | Ser | Ala | Lys | Glu | Asn | Val | Asn | Val | Lys | Ala | Val | Phe | Glu | Arg |
|  |  |  |  | 165 |  |  |  |  | 170 |  |  |  |  | 175 |
| Leu | Val | Asp | Ile | Ile | Cys | Lys | Met | Ser | Glu | Ser | Leu | Asp | Ala | Asp | Pro |
|  |  |  | 180 |  |  |  |  | 185 |  |  |  |  | 190 |
| Thr | Leu | Val | Gly | Gly | Gly | Gln | Lys | Gly | Gln | Arg | Leu | Thr | Asp | Gln | Pro |
|  |  | 195 |  |  |  |  | 200 |  |  |  |  | 205 |
| Gln | Gly | Thr | Pro | Asn | Ala | Asn | Cys | Asn | Cys |
|  |  | 210 |  |  |  |  | 215 |

( 2 ) INFORMATION FOR SEQ ID NO:20:

( i ) SEQUENCE CHARACTERISTICS:
        ( A ) LENGTH: 208 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v i ) ORIGINAL SOURCE:
    ( A ) ORGANISM: Rattus norvegicus ( x i ) SEQUENCE DESCRIPTION: SEQ ID NO:20:

```
Met Ser Glu Thr Tyr Asp Phe Leu Lys Phe Leu Val Ile Gly Asn Ala
1               5                   10                  15

Gly Thr Gly Lys Ser Cys Leu Leu His Gln Phe Ile Glu Lys Lys Phe
            20                  25                  30

Lys Asp Asp Ser Asn His Thr Ile Gly Val Glu Phe Gly Gln Lys Ile
        35                  40                  45

Ile Asn Val Gly Gly Lys Tyr Val Lys Leu Gln Ile Trp Asp Thr Ala
    50                  55                  60

Gly Gln Glu Arg Phe Arg Val Thr Thr Ser Tyr Arg Gly Ala Ala Gly
65                  70                  75                  80

Ala Leu Leu Val Tyr Asp Ile Thr Ser Arg Glu Thr Tyr Asn Ala Leu
                85                  90                  95

Thr Asn Trp Leu Thr Asp Ala Arg Met Leu Ala Ser Gln Asn Ile Val
            100                 105                 110

Ile Cys Gly Asn Lys Lys Asp Leu Asp Ala Asp Arg Glu Val Thr Phe
        115                 120                 125

Leu Glu Ala Ser Arg Phe Ala Gln Glu Asn Glu Leu Met Phe Leu Glu
    130                 135                 140

Thr Ser Ala Leu Thr Gly Glu Asn Val Glu Glu Ala Phe Met Gln Cys
145                 150                 155                 160

Ala Arg Lys Ile Leu Asn Lys Ile Glu Ser Gly Glu Leu Asp Pro Glu
                165                 170                 175

Arg Met Gly Ser Gly Ile Gln Tyr Gly Asp Ala Ala Leu Arg Gln Leu
            180                 185                 190

Arg Ser Pro Arg Arg Thr Gln Ala Pro Ser Ala Gln Glu Cys Gly Cys
        195                 200                 205
```

( 2 ) INFORMATION FOR SEQ ID NO:21:

( i ) SEQUENCE CHARACTERISTICS:
        ( A ) LENGTH: 203 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Caenorhabditis elegans ( x i ) SEQUENCE DESCRIPTION: SEQ ID NO:21:

```
Met Ala Asp Phe Thr Asn Asn Ala Leu Lys Lys Phe Lys Leu Val Phe
1               5                   10                  15

Leu Gly Glu Gln Ser Val Gly Lys Thr Ser Ile Ile Thr Arg Phe Met
            20                  25                  30

Tyr Asp Ser Phe Asp Asn Thr Tyr Gln Ala Thr Ile Gly Ile Asp Phe
        35                  40                  45

Leu Ser Lys Thr Met Tyr Leu Glu Asp Arg Thr Ile Arg Leu Gln Leu
    50                  55                  60

Trp Asp Thr Ala Gly Gln Glu Arg Phe Arg Ser Leu Ile Pro Ser Tyr
65                  70                  75                  80
```

```
Ile  Arg  Asp  Ser  Ser  Val  Ala  Val  Val  Val  Tyr  Asp  Ile  Thr  Asn  Ala
                    85                       90                      95

Asn  Ser  Phe  His  Gln  Thr  Thr  Lys  Trp  Val  Asp  Asp  Val  Arg  Asn  Glu
                    100                      105                     110

Arg  Gly  Cys  Asp  Val  Ile  Ile  Val  Leu  Val  Gly  Asn  Lys  Thr  Asp  Leu
               115                      120                 125

Ala  Asp  Lys  Arg  Gln  Val  Ser  Thr  Glu  Asp  Gly  Glu  Lys  Lys  Ala  Arg
     130                      135                      140

Asp  Leu  Asn  Val  Met  Phe  Ile  Glu  Thr  Ser  Ala  Lys  Ala  Gly  Tyr  Asn
145                      150                      155                     160

Val  Lys  Gln  Leu  Phe  Arg  Lys  Ile  Ala  Leu  Pro  Gly  Ile  Val  Gln  Glu
                    165                      170                     175

Glu  Thr  Pro  Glu  Gln  Pro  Asn  Ile  Val  Ile  Met  Asn  Pro  Pro  Lys  Asp
               180                      185                 190

Ala  Glu  Glu  Ser  Gln  Gly  Arg  Gln  Cys  Pro  Cys
          195                      200
```

( 2 ) INFORMATION FOR SEQ ID NO:22:

( i ) SEQUENCE CHARACTERISTICS:
        ( A ) LENGTH: 207 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:22:

```
Met  Ser  Thr  Gly  Gly  Asp  Phe  Gly  Asn  Pro  Leu  Arg  Lys  Phe  Lys  Leu
1              5                    10                      15

Val  Phe  Leu  Gly  Glu  Gln  Ser  Val  Gly  Lys  Thr  Ser  Leu  Ile  Thr  Arg
               20                      25                      30

Phe  Met  Tyr  Asp  Ser  Phe  Asp  Asn  Thr  Tyr  Gln  Ala  Thr  Ile  Gly  Ile
          35                      40                      45

Asp  Phe  Leu  Ser  Lys  Thr  Met  Tyr  Leu  Glu  Asp  Arg  Thr  Val  Arg  Leu
     50                      55                      60

Gln  Leu  Trp  Asp  Thr  Ala  Gly  Gln  Glu  Arg  Phe  Arg  Ser  Leu  Ile  Pro
65                       70                      75                      80

Ser  Tyr  Ile  Arg  Asp  Ser  Thr  Val  Ala  Val  Val  Val  Tyr  Asp  Ile  Thr
                    85                       90                     95

Asn  Val  Asn  Ser  Phe  Gln  Gln  Thr  Thr  Lys  Trp  Ile  Asp  Asp  Val  Arg
                    100                      105                    110

Thr  Glu  Arg  Gly  Ser  Asp  Val  Ile  Ile  Met  Leu  Val  Gly  Asn  Lys  Thr
          115                      120                      125

Asp  Leu  Ala  Asp  Lys  Arg  Gln  Val  Ser  Ile  Glu  Glu  Gly  Glu  Arg  Lys
     130                      135                      140

Ala  Lys  Glu  Leu  Asn  Val  Met  Phe  Ile  Glu  Ser  Ala  Lys  Ala  Gly  Tyr
145                      150                      155                    160

Asn  Val  Lys  Gln  Leu  Phe  Arg  Arg  Val  Ala  Ala  Ala  Leu  Pro  Gly  Met
                    165                      170                     175

Glu  Ser  Thr  Gln  Asp  Arg  Ser  Arg  Glu  Asp  Met  Ile  Asp  Ile  Lys  Leu
               180                      185                     190

Glu  Lys  Pro  Gln  Glu  Gln  Pro  Val  Ser  Glu  Gly  Gly  Cys  Ser  Cys
          195                      200                      205
```

(2) INFORMATION FOR SEQ ID NO:23:

(i) SEQUENCE CHARACTERISTICS:
        (A) LENGTH: 203 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Canis familiaris (xi) SEQUENCE DESCRIPTION: SEQ ID NO:23:

```
Met Thr Ser Arg Lys Lys Val Leu Leu Lys Val Ile Ile Leu Gly Asp
 1               5                  10                  15
Ser Gly Val Gly Lys Thr Ser Leu Met Asn Gln Tyr Val Asn Lys Lys
             20                  25                  30
Phe Ser Asn Gln Tyr Lys Ala Thr Ile Gly Ala Asp Phe Leu Thr Lys
             35                  40                  45
Glu Val Met Val Asp Asp Arg Leu Val Thr Met Gln Ile Trp Asp Thr
         50                  55                  60
Ala Gly Gln Glu Arg Phe Gln Ser Leu Gly Val Phe Tyr Arg Gly Ala
 65                  70                  75                  80
Asp Cys Cys Val Leu Val Phe Asp Val Thr Ala Pro Asn Thr Phe Lys
                 85                  90                  95
Thr Leu Asp Ser Trp Arg Asp Glu Phe Leu Ile Gln Ala Ser Pro Arg
            100                 105                 110
Asp Pro Glu Asn Phe Pro Phe Val Val Leu Gly Asn Lys Ile Asp Leu
            115                 120                 125
Glu Asn Arg Gln Val Ala Thr Lys Arg Ala Gln Ala Trp Cys Tyr Ser
            130                 135                 140
Lys Asn Asn Ile Pro Tyr Phe Glu Thr Ser Ala Lys Glu Ala Ile Asn
145                 150                 155                 160
Val Glu Gln Ala Phe Gln Thr Ile Ala Arg Asn Ala Leu Lys Gln Glu
                165                 170                 175
Thr Glu Val Glu Leu Tyr Asn Glu Phe Pro Glu Pro Ile Lys Leu Asp
            180                 185                 190
Lys Asp Ala Lys Thr Ser Ala Glu Cys Ser Cys
            195                 200
```

(2) INFORMATION FOR SEQ ID NO:24:

(i) SEQUENCE CHARACTERISTICS:
        (A) LENGTH: 202 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Dictyostelium discoideum (xi) SEQUENCE DESCRIPTION: SEQ ID NO:24:

```
Met Thr Lys Lys Lys Val Leu Leu Lys Val Ile Ile Leu Gly Asp Ser
 1               5                  10                  15
Gly Val Gly Lys Thr Ser Leu Met Asn Gln Tyr Val Asn Lys Lys Phe
```

|    |     |     |     |     |     |     |     | 20  |     |     |     |     | 25  |     |     |     |     | 30  |     |
|----|-----|-----|-----|-----|-----|-----|-----|-----|-----|-----|-----|-----|-----|-----|-----|-----|-----|-----|-----|

Ser Asn Gln Tyr Lys Ala Thr Ile Gly Ala Asp Phe Leu Thr Lys Glu
        35                    40                  45

Leu Met Val Asp Asp Arg Val Val Thr Met Gln Ile Trp Asp Thr Ala
    50                  55                  60

Gly Gln Glu Arg Phe Gln Ser Leu Gly Val Ala Phe Tyr Arg Gly Ala
65                  70                  75                  80

Asp Cys Cys Val Leu Cys Tyr Asp Val Asn Val Ala Lys Thr Phe Glu
                85                  90                  95

Asn Leu Asp Ser Trp Arg Asp Glu Phe Leu Ile Gln Ala Gly Pro Arg
            100                 105                 110

Asp Pro Asp Asn Phe Pro Phe Val Val Leu Gly Asn Lys Ile Asp Leu
            115                 120                 125

Glu Asn Gln Arg Val Val Ser Gln Lys Arg Ala Ala Ser Trp Cys Gln
    130                 135                 140

Ser Lys Gly Asn Ile Pro Tyr Phe Glu Thr Ser Ala Lys Glu Ala Ile
145                 150                 155                 160

Asn Val Glu Gln Ala Phe Gln Thr Ile Ala Arg Asn Ala Ile Lys Leu
                165                 170                 175

Glu Asp Gly Leu Val Phe Pro Ile Pro Thr Asn Ile Gln Val Ile Pro
            180                 185                 190

Glu Pro Gln Pro Ala Lys Ser Gly Cys Cys
        195                 200

( 2 ) INFORMATION FOR SEQ ID NO:25:

( i ) SEQUENCE CHARACTERISTICS:
        ( A ) LENGTH: 205 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Canis familiaris ( x i ) SEQUENCE DESCRIPTION: SEQ ID NO:25:

Met Lys Thr Tyr Asp Tyr Leu Phe Lys Leu Leu Leu Ile Gly Asp Ser
1               5                   10                  15

Gly Val Gly Lys Thr Cys Val Leu Phe Arg Phe Ser Glu Asp Ala Phe
            20                  25                  30

Asn Ser Thr Phe Ile Ser Thr Ile Gly Ile Asp Phe Lys Ile Arg Thr
        35                  40                  45

Ile Glu Leu Asp Gly Lys Arg Ile Lys Leu Gln Ile Trp Asp Thr Ala
    50                  55                  60

Gly Gln Glu Arg Phe Arg Thr Ile Thr Thr Ala Tyr Tyr Arg Ala Met
65                  70                  75                  80

Gly Ile Met Leu Val Tyr Asp Ile Thr Asn Glu Lys Ser Phe Asp Asn
                85                  90                  95

Ile Arg Asn Trp Ile Arg Asn Ile Glu Glu His Ala Ser Ala Asp Val
            100                 105                 110

Glu Lys Met Ile Leu Gly Asn Lys Cys Asp Val Asn Asp Lys Arg Gln
        115                 120                 125

Val Ser Lys Glu Arg Gly Glu Lys Leu Ala Leu Asp Tyr Gly Ile Lys
    130                 135                 140

```
Phe  Met  Glu  Thr  Ser  Ala  Lys  Ala  Asn  Ile  Asn  Val  Glu  Asn  Ala  Phe
145                 150                      155                      160

Phe  Thr  Leu  Ala  Arg  Asp  Ile  Lys  Ala  Lys  Met  Asp  Lys  Lys  Leu  Glu
                    165                      170                      175

Gly  Asn  Ser  Pro  Gln  Gly  Ser  Asn  Gln  Gly  Val  Lys  Ile  Thr  Pro  Asp
                    180                      185                      190

Gln  Gln  Lys  Arg  Ser  Ser  Phe  Phe  Arg  Cys  Val  Leu  Leu
          195                      200                      205
```

(2) INFORMATION FOR SEQ ID NO:26:

(i) SEQUENCE CHARACTERISTICS:
        (A) LENGTH: 191 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Dictyostelium discoideum (xi) SEQUENCE DESCRIPTION: SEQ ID NO:26:

```
Met  Glu  Glu  Glu  Ile  Leu  Tyr  Lys  Ile  Ile  Leu  Val  Gly  Glu  Ser  Gly
1                   5                        10                      15

Val  Gly  Lys  Ser  Ser  Ile  Leu  Val  Arg  Phe  Thr  Asp  Asn  Thr  Phe  Ser
               20                  25                      30

Gln  His  Phe  Ala  Pro  Thr  Leu  Gly  Val  Phe  Val  Lys  Thr  Ile  Arg  Asn
               35                  40                      45

Lys  Glu  Thr  Gly  Gln  Thr  Val  Lys  Leu  Gln  Leu  Trp  Asp  Thr  Ala  Gly
          50                  55                      60

Gln  Glu  Arg  Phe  Lys  Ser  Ile  Thr  Gln  Phe  Tyr  Arg  Gly  Ser  His  Gly
65                       70                      75                      80

Val  Ile  Val  Val  Tyr  Asp  Val  Thr  Asp  Pro  Lys  Ser  Phe  Glu  Arg  Leu
                    85                       90                      95

Lys  Asn  Trp  Val  Glu  Asp  Ile  Asn  Gln  Tyr  Thr  Gln  Asp  Gly  Met  Ile
               100                 105                     110

Ile  Ile  Leu  Val  Gly  Asn  Lys  Ser  Asp  Met  Val  Ala  Gln  Arg  Lys  Val
               115                 120                     125

Thr  Phe  Glu  Gln  Gly  Gln  Glu  Met  Ala  Glu  Gln  Leu  Lys  Thr  Lys  Phe
          130                 135                     140

Leu  Glu  Val  Ser  Ala  Lys  Glu  Asn  Asn  Gly  Val  Thr  Gln  Val  Phe  Asp
145                 150                      155                     160

Leu  Leu  Val  Gln  Asp  Ile  Glu  Ala  Thr  Met  Lys  Asn  Ser  Lys  Val  Ala
                    165                      170                     175

Gln  Asn  Gln  Leu  Asn  Leu  Ser  Val  Gly  Gln  Glu  Arg  Gly  Cys  Cys
               180                 185                     190
```

(2) INFORMATION FOR SEQ ID NO:27:

(i) SEQUENCE CHARACTERISTICS:
        (A) LENGTH: 189 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:

(A) ORGANISM: Caenorhabditis elegans (xi) SEQUENCE DESCRIPTION: SEQ ID NO:27:

| Met | Gln | Ala | Ile | Lys | Cys | Val | Val | Val | Gly | Asp | Gly | Ala | Val | Gly | Lys |
|---|---|---|---|---|---|---|---|---|---|---|---|---|---|---|---|
| 1 | | | | 5 | | | | | 10 | | | | | 15 | |
| Thr | Cys | Leu | Leu | Ile | Ser | Tyr | Thr | Thr | Asn | Ala | Phe | Pro | Gly | Glu | Tyr |
| | | | 20 | | | | 25 | | | | | | 30 | | |
| Ile | Pro | Thr | Val | Phe | Asp | Asn | Tyr | Ser | Ala | Asn | Val | Met | Val | Asp | Gly |
| | | 35 | | | | | 40 | | | | | 45 | | | |
| Arg | Pro | Ile | Asn | Leu | Gly | Leu | Trp | Asp | Thr | Ala | Gly | Gln | Asp | Tyr | Asp |
| | 50 | | | | | 55 | | | | | 60 | | | | |
| Arg | Leu | Arg | Pro | Leu | Ser | Tyr | Pro | Gln | Thr | Asp | Val | Phe | Leu | Val | Cys |
| 65 | | | | | 70 | | | | 75 | | | | | | 80 |
| Phe | Ala | Leu | Asn | Asn | Pro | Ala | Ser | Phe | Glu | Asn | Val | Arg | Ala | Lys | Trp |
| | | | | 85 | | | | | 90 | | | | | 95 | |
| Tyr | Pro | Glu | Val | Ser | His | His | Cys | Pro | Asn | Thr | Pro | Ile | Ile | Leu | Val |
| | | | 100 | | | | | 105 | | | | | 110 | | |
| Gly | Thr | Lys | Ala | Asp | Leu | Arg | Glu | Asp | Asp | Thr | Val | Glu | Arg | Leu | Arg |
| | | 115 | | | | | 120 | | | | | 125 | | | |
| Glu | Arg | Arg | Leu | Gln | Pro | Val | Ser | Gln | Thr | Gln | Gly | Tyr | Val | Met | Ala |
| | 130 | | | | | 135 | | | | | 140 | | | | |
| Lys | Glu | Ile | Lys | Ala | Val | Lys | Tyr | Leu | Glu | Cys | Ser | Ala | Leu | Thr | Gln |
| 145 | | | | | 150 | | | | | 155 | | | | | 160 |
| Arg | Gly | Leu | Lys | Gln | Val | Phe | Asp | Glu | Ala | Ile | Arg | Ala | Val | Val | Thr |
| | | | | 165 | | | | | 170 | | | | | 175 | |
| Pro | Pro | Gln | Arg | Ala | Lys | Lys | Ser | Lys | Cys | Thr | Val | Leu | | | |
| | | | 180 | | | | | 185 | | | | | | | |

(2) INFORMATION FOR SEQ ID NO:28:

(i) SEQUENCE CHARACTERISTICS:
        (A) LENGTH: 191 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Dictyostelium discoideum (xi) SEQUENCE DESCRIPTION: SEQ ID NO:28:

| Met | Gln | Ala | Ile | Lys | Cys | Val | Val | Val | Gly | Asp | Gly | Ala | Val | Gly | Lys |
|---|---|---|---|---|---|---|---|---|---|---|---|---|---|---|---|
| 1 | | | | 5 | | | | | 10 | | | | | 15 | |
| Thr | Cys | Leu | Leu | Ile | Ser | Tyr | Thr | Thr | Asn | Ala | Phe | Pro | Gly | Glu | Tyr |
| | | | 20 | | | | 25 | | | | | | 30 | | |
| Ile | Pro | Thr | Val | Phe | Asp | Asn | Tyr | Ser | Ala | Asn | Val | Met | Val | Asp | Gly |
| | | 35 | | | | | 40 | | | | | 45 | | | |
| Lys | Pro | Ile | Asn | Leu | Gly | Leu | Trp | Asp | Thr | Ala | Gly | Gln | Glu | Asp | Tyr |
| | 50 | | | | | 55 | | | | | 60 | | | | |
| Asp | Arg | Leu | Arg | Pro | Leu | Ser | Tyr | Pro | Gln | Thr | Asp | Val | Phe | Leu | Ile |
| 65 | | | | | 70 | | | | 75 | | | | | | 80 |
| Cys | Phe | Ser | Ile | Ile | Ser | Pro | Ser | Ser | Phe | Glu | Asn | Val | Asn | Gly | Lys |
| | | | | 85 | | | | | 90 | | | | | 95 | |
| Trp | His | Pro | Glu | Ile | Cys | His | His | Pro | Asn | Val | Pro | Ile | Leu | Val | Gly |
| | | | 100 | | | | | 105 | | | | | 110 | | |
| Thr | Lys | Leu | Asp | Met | Arg | Asp | Lys | Glu | Thr | Gln | Asp | Arg | Leu | Lys | Glu |

|     |     |     |     | 115 |     |     |     |     | 120 |     |     |     |     | 125 |     |
| --- | --- | --- | --- | --- | --- | --- | --- | --- | --- | --- | --- | --- | --- | --- | --- |
| Lys | Lys<br>130 | Leu | Tyr | Pro | Ile | Ser<br>135 | Tyr | Glu | Gln | Gly | Leu<br>140 | Ala | Lys | Met | Lys |
| Glu<br>145 | Ile | Asn | Ala | Val | Lys<br>150 | Tyr | Leu | Glu | Cys | Ser<br>155 | Ala | Leu | Thr | Glu | Lys<br>160 |
| Gly | Leu | Lys | Thr | Val<br>165 | Phe | Asp | Glu | Ala | Ile<br>170 | Arg | Ala | Val | Ile | Asn<br>175 | Pro |
| Pro | Leu | Ser | Lys<br>180 | Lys | Lys | Ser | Ser<br>185 | Gly | Gly | Cys | Asn | Ile<br>190 | Leu |     |     |

( 2 ) INFORMATION FOR SEQ ID NO:29:

( i ) SEQUENCE CHARACTERISTICS:
        ( A ) LENGTH: 192 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Dictyostelium discoideum ( x i ) SEQUENCE DESCRIPTION: SEQ ID NO:29:

| Met<br>1 | Gln | Ser | Ile | Lys<br>5 | Leu | Val | Val | Val | Gly<br>10 | Asp | Gly | Ala | Val | Gly<br>15 | Lys |
| --- | --- | --- | --- | --- | --- | --- | --- | --- | --- | --- | --- | --- | --- | --- | --- |
| Thr | Cys | Leu | Leu<br>20 | Ile | Ser | Tyr | Thr | Ser<br>25 | Asn | Ser | Phe | Pro | Thr<br>30 | Glu | Tyr |
| Val | Pro | Thr<br>35 | Val | Phe | Asp | Asn | Tyr<br>40 | Ser | Ala | Asn | Val | Met<br>45 | Val | Asp | Asn |
| Lys<br>50 | Thr | Val | Ser | Leu | Gly<br>55 | Leu | Trp | Asp | Thr | Ala<br>60 | Gly | Gln | Glu | Asp | Tyr |
| Asp<br>65 | Arg | Leu | Arg | Pro | Leu<br>70 | Ser | Tyr | Pro | Gln | Thr<br>75 | Asp | Val | Phe | Leu | Ile<br>80 |
| Cys | Phe | Ala | Ile | Ile<br>85 | Ser | Gln | Ser | Tyr | Thr<br>90 | Asn | Val | Lys | Ser | Lys<br>95 | Trp |
| Trp | Pro | Glu | Val<br>100 | Thr | His | His | Cys | Pro<br>105 | Asn | Cys | Thr | Ile | Leu<br>110 | Val | Gly |
| Thr | Lys | Cys<br>115 | Asp | Leu | Arg | Asp | Lys<br>120 | Glu | Ser | Leu | Glu | Lys<br>125 | Leu | Arg | Glu |
| Lys | His<br>130 | Gln | Gln | Pro | Leu | Thr<br>135 | Phe | Gln | Gln | Gly | Glu<br>140 | Gln | Met | Ala | Lys |
| Glu<br>145 | Ile | Lys | Ala | Phe | Cys<br>150 | Tyr | Met | Glu | Cys | Ser<br>155 | Ala | Leu | Thr | Gln | Lys<br>160 |
| Gly | Leu | Lys | Gln | Val<br>165 | Phe | Asp | Glu | Ala | Ile<br>170 | Lys | Ala | Val | Ile | Phe<br>175 | Pro |
| Asp | Arg | Asp | Lys<br>180 | Ala | Thr | Asn | Lys | Lys<br>185 | Asn | Ser | Lys | Cys | Ser<br>190 | Ile | Leu |

( 2 ) INFORMATION FOR SEQ ID NO:30:

( i ) SEQUENCE CHARACTERISTICS:
        ( A ) LENGTH: 185 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO (v i) ORIGINAL SOURCE:
 (A) ORGANISM: Dictyostelium discoideum (x i) SEQUENCE DESCRIPTION: SEQ ID NO:30:

| Met | Ser | Ala | Ala | Glu | Val | Ile | Lys | Leu | Val | Val | Ile | Gly | Gly | Ala | Val |
|---|---|---|---|---|---|---|---|---|---|---|---|---|---|---|---|
| 1 | | | | 5 | | | | | 10 | | | | | 15 | |

| Gly | Lys | Thr | Cys | Leu | Leu | Ile | Tyr | Ala | Asn | Asn | Arg | Phe | Pro | Glu | Asp |
|---|---|---|---|---|---|---|---|---|---|---|---|---|---|---|---|
| | | | 20 | | | | 25 | | | | | | 30 | | |

| Tyr | Ile | Pro | Thr | Val | Phe | Asp | Asn | Tyr | Val | Val | Asn | Leu | Thr | Ala | Gly |
|---|---|---|---|---|---|---|---|---|---|---|---|---|---|---|---|
| | | 35 | | | | | 40 | | | | | 45 | | | |

| Asp | Arg | Asn | Ile | Glu | Leu | Gly | Leu | Trp | Asp | Thr | Ala | Gly | Glu | Tyr | Asp |
|---|---|---|---|---|---|---|---|---|---|---|---|---|---|---|---|
| | 50 | | | | | 55 | | | | | 60 | | | | |

| Lys | Leu | Arg | Pro | Leu | Ser | Tyr | Ala | Asn | Asn | Val | Phe | Leu | Ile | Cys | Phe |
|---|---|---|---|---|---|---|---|---|---|---|---|---|---|---|---|
| 65 | | | | | 70 | | | | | 75 | | | | | 80 |

| Ser | Ile | Asn | Pro | Val | Ser | Phe | Glu | Asn | Val | Tyr | Thr | Lys | Trp | Tyr | Pro |
|---|---|---|---|---|---|---|---|---|---|---|---|---|---|---|---|
| | | | | 85 | | | | | 90 | | | | | 95 | |

| Glu | Val | Met | His | Phe | Cys | Pro | Glu | Val | Gln | Ile | Leu | Val | Gly | Thr | Lys |
|---|---|---|---|---|---|---|---|---|---|---|---|---|---|---|---|
| | | | 100 | | | | | 105 | | | | | 110 | | |

| Leu | Asp | Thr | Arg | Asp | Asp | Arg | Gly | Val | Leu | Asp | Lys | Leu | Gln | Gln | Thr |
|---|---|---|---|---|---|---|---|---|---|---|---|---|---|---|---|
| | | 115 | | | | | 120 | | | | | 125 | | | |

| Gly | His | Lys | Pro | Ile | Thr | Thr | Glu | Gln | Gly | Asn | Asp | Leu | Ala | Arg | Arg |
|---|---|---|---|---|---|---|---|---|---|---|---|---|---|---|---|
| | 130 | | | | | 135 | | | | | 140 | | | | |

| Ile | Lys | Ala | Ile | Lys | Tyr | Met | Glu | Cys | Ser | Ala | Lys | Thr | Ser | Gln | Asn |
|---|---|---|---|---|---|---|---|---|---|---|---|---|---|---|---|
| 145 | | | | | 150 | | | | | 155 | | | | | 160 |

| Leu | Lys | Gln | Val | Phe | Asp | Glu | Ala | Ile | Lys | Ser | Val | Leu | Phe | Ile | Lys |
|---|---|---|---|---|---|---|---|---|---|---|---|---|---|---|---|
| | | | | 165 | | | | | 170 | | | | | 175 | |

| Lys | Lys | Lys | Ser | Lys | Cys | Ile | Val | Met |
|---|---|---|---|---|---|---|---|---|
| | | | 180 | | | | | 185 |

(2) INFORMATION FOR SEQ ID NO:31:

(i) SEQUENCE CHARACTERISTICS:
  (A) LENGTH: 205 amino acids
  (B) TYPE: amino acid
  (C) STRANDEDNESS: single
  (D) TOPOLOGY: linear (ii) MOLECULE TYPE: protein (iii) HYPOTHETICAL: NO (vi) ORIGINAL SOURCE:
  (A) ORGANISM: Homo sapiens (xi) SEQUENCE DESCRIPTION: SEQ ID NO:31:

| Met | Ala | Ala | Asn | Lys | Pro | Lys | Gly | Gln | Asn | Ser | Leu | Ala | Leu | His | Lys |
|---|---|---|---|---|---|---|---|---|---|---|---|---|---|---|---|
| 1 | | | | 5 | | | | | 10 | | | | | 15 | |

| Val | Ile | Met | Val | Gly | Ser | Gly | Gly | Val | Gly | Lys | Ser | Ala | Leu | Thr | Leu |
|---|---|---|---|---|---|---|---|---|---|---|---|---|---|---|---|
| | | | 20 | | | | | 25 | | | | | 30 | | |

| Gln | Phe | Met | Tyr | Asp | Glu | Phe | Val | Glu | Asp | Tyr | Glu | Pro | Thr | Lys | Ala |
|---|---|---|---|---|---|---|---|---|---|---|---|---|---|---|---|
| | | | 35 | | | | | 40 | | | | | 45 | | |

| Asp | Ser | Tyr | Arg | Lys | Lys | Val | Val | Leu | Asp | Gly | Glu | Glu | Val | Gln | Ile |
|---|---|---|---|---|---|---|---|---|---|---|---|---|---|---|---|
| | 50 | | | | | 55 | | | | | 60 | | | | |

| Asp | Ile | Leu | Asp | Thr | Ala | Gly | Gln | Glu | Asp | Tyr | Ala | Ala | Ile | Arg | Asp |
|---|---|---|---|---|---|---|---|---|---|---|---|---|---|---|---|
| 65 | | | | | 70 | | | | | 75 | | | | | 80 |

| Asn | Tyr | Phe | Arg | Ser | Gly | Glu | Gly | Phe | Leu | Cys | Val | Phe | Ser | Ile | Thr |
|---|---|---|---|---|---|---|---|---|---|---|---|---|---|---|---|
| | | | | 85 | | | | | 90 | | | | | 95 | |

| Glu | Met | Glu | Ser | Phe | Ala | Ala | Thr | Ala | Asp | Phe | Arg | Glu | Gln | Ile | Leu |
|---|---|---|---|---|---|---|---|---|---|---|---|---|---|---|---|
| | | | 100 | | | | | 105 | | | | | 110 | | |

|     |     |     |     |     |     |     |     |     |     |     |     |     |     |     |
|-----|-----|-----|-----|-----|-----|-----|-----|-----|-----|-----|-----|-----|-----|-----|
| Arg | Val | Lys | Glu | Asp | Glu | Asn | Val | Pro | Phe | Leu | Leu | Val | Gly | Asn | Lys |
|     |     | 115 |     |     |     |     | 120 |     |     |     |     | 125 |     |     |
| Ser | Asp | Leu | Glu | Asp | Lys | Arg | Gln | Val | Ser | Val | Glu | Glu | Ala | Lys | Asn |
|     |     | 130 |     |     |     | 135 |     |     |     |     | 140 |     |     |     |
| Arg | Ala | Glu | Gln | Trp | Asn | Val | Asn | Tyr | Val | Glu | Thr | Ser | Ala | Lys | Thr |
| 145 |     |     |     |     | 150 |     |     |     |     | 155 |     |     |     |     | 160 |
| Arg | Ala | Asn | Val | Asp | Lys | Val | Phe | Phe | Asp | Leu | Met | Arg | Glu | Ile | Arg |
|     |     |     |     | 165 |     |     |     |     | 170 |     |     |     |     | 175 |     |
| Ala | Arg | Lys | Met | Glu | Asp | Ser | Lys | Lys | Asn | Gly | Lys | Lys | Arg | Lys |
|     |     |     | 180 |     |     |     |     | 185 |     |     |     | 190 |     |     |
| Ser | Leu | Ala | Lys | Arg | Ile | Arg | Glu | Arg | Cys | Cys | Ile | Leu |
|     |     | 195 |     |     |     |     | 200 |     |     |     |     | 205 |

( 2 ) INFORMATION FOR SEQ ID NO:32:

( i ) SEQUENCE CHARACTERISTICS:
        ( A ) LENGTH: 204 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:32:

|     |     |     |     |     |     |     |     |     |     |     |     |     |     |     |     |
|-----|-----|-----|-----|-----|-----|-----|-----|-----|-----|-----|-----|-----|-----|-----|-----|
| Met | Ala | Ala | Asn | Lys | Ser | Lys | Gly | Gln | Ser | Ser | Leu | Ala | Leu | His | Lys |
| 1   |     |     |     | 5   |     |     |     |     | 10  |     |     |     |     | 15  |     |
| Val | Ile | Met | Val | Gly | Ser | Gly | Gly | Val | Gly | Lys | Ser | Ala | Leu | Thr | Leu |
|     |     |     | 20  |     |     |     |     | 25  |     |     |     |     | 30  |     |     |
| Gln | Phe | Met | Tyr | Asp | Glu | Phe | Val | Glu | Asp | Tyr | Glu | Pro | Thr | Lys | Ala |
|     |     |     | 35  |     |     |     |     | 40  |     |     |     |     | 45  |     |     |
| Asp | Ser | Tyr | Arg | Lys | Lys | Val | Val | Leu | Asp | Gly | Glu | Glu | Val | Ile | Asp |
|     |     | 50  |     |     |     |     | 55  |     |     |     |     | 60  |     |     |     |
| Ile | Leu | Asp | Thr | Ala | Gly | Gln | Glu | Asp | Tyr | Ala | Ile | Arg | Asp | Asn | Tyr |
| 65  |     |     |     |     | 70  |     |     |     |     | 75  |     |     |     |     | 80  |
| Phe | Arg | Ser | Gly | Glu | Gly | Phe | Leu | Leu | Val | Phe | Ser | Ile | Thr | Glu | His |
|     |     |     |     | 85  |     |     |     |     | 90  |     |     |     |     | 95  |     |
| Glu | Ser | Phe | Thr | Ala | Thr | Ala | Glu | Phe | Arg | Glu | Gln | Ile | Leu | Arg | Val |
|     |     |     | 100 |     |     |     |     | 105 |     |     |     |     | 110 |     |     |
| Lys | Ala | Glu | Glu | Asp | Lys | Ile | Pro | Leu | Leu | Val | Val | Gly | Asn | Lys | Ser |
|     |     |     | 115 |     |     |     |     | 120 |     |     |     |     | 125 |     |     |
| Asp | Leu | Glu | Glu | Arg | Arg | Gln | Val | Pro | Val | Glu | Glu | Ala | Arg | Ser | Lys |
|     |     | 130 |     |     |     |     | 135 |     |     |     |     | 140 |     |     |     |
| Ala | Glu | Glu | Trp | Gly | Val | Gln | Tyr | Val | Glu | Thr | Ser | Ala | Lys | Thr | Arg |
| 145 |     |     |     |     | 150 |     |     |     |     | 155 |     |     |     |     | 160 |
| Ala | Asn | Val | Asp | Lys | Val | Phe | Phe | Asp | Leu | Met | Arg | Glu | Ile | Arg | Thr |
|     |     |     |     | 165 |     |     |     |     | 170 |     |     |     |     | 175 |     |
| Lys | Lys | Met | Ser | Glu | Asn | Lys | Asp | Lys | Asn | Gly | Lys | Lys | Ser | Ser | Lys |
|     |     |     | 180 |     |     |     |     | 185 |     |     |     | 190 |     |     |     |
| Asn | Lys | Lys | Ser | Phe | Lys | Glu | Arg | Cys | Cys | Leu | Leu |
|     |     | 195 |     |     |     |     | 200 |     |     |     |

( 2 ) INFORMATION FOR SEQ ID NO:33:

( i ) SEQUENCE CHARACTERISTICS:

(A) LENGTH: 200 amino acids
(B) TYPE: amino acid
(C) STRANDEDNESS: single
(D) TOPOLOGY: linear (ii) MOLECULE TYPE: protein (iii) HYPOTHETICAL: NO (vi) ORIGINAL SOURCE:
(A) ORGANISM: Discopyge ommata (xi) SEQUENCE DESCRIPTION: SEQ ID NO:33:

| Met | Ala | Ala | Asn | Lys | Asn | Lys | Asn | Gln | Ser | Ser | Leu | Leu | Lys | Val | Ile |
|---|---|---|---|---|---|---|---|---|---|---|---|---|---|---|---|
| 1 | | | | 5 | | | | | 10 | | | | | 15 | |

| Met | Val | Gly | Ser | Gly | Gly | Val | Gly | Lys | Ser | Ala | Leu | Thr | Leu | Gln | Phe |
| | | | 20 | | | | | 25 | | | | | 30 | | |

| Met | Tyr | Asp | Glu | Phe | Val | Glu | Asp | Tyr | Glu | Pro | Thr | Lys | Ala | Asp | Ser |
| | | 35 | | | | | 40 | | | | | 45 | | | |

| Tyr | Arg | Lys | Lys | Val | Val | Leu | Asp | Gly | Glu | Val | Gln | Ile | Asp | Ile | Leu |
| | | 50 | | | | | 55 | | | | | 60 | | | |

| Asp | Thr | Ala | Gly | Gln | Glu | Asp | Tyr | Ala | Ile | Arg | Asp | Asn | Tyr | Phe | Arg |
| 65 | | | | | 70 | | | | | 75 | | | | | 80 |

| Ser | Gly | Glu | Gly | Phe | Leu | Cys | Val | Phe | Ser | Ile | Glu | Gln | Glu | Ser | Phe |
| | | | | 85 | | | | | 90 | | | | | 95 | |

| Thr | Ala | Thr | Val | Glu | Phe | Arg | Glu | Gln | Ile | Leu | Arg | Val | Lys | Glu | Glu |
| | | | 100 | | | | | 105 | | | | | 110 | | |

| Asp | Lys | Ile | Pro | Leu | Leu | Leu | Val | Gly | Asn | Lys | Ser | Asp | Leu | Glu | Asp |
| | | | 115 | | | | | 120 | | | | | 125 | | |

| Arg | Arg | Gln | Val | Ser | Ile | Glu | Glu | Ala | Arg | Ser | Lys | Ala | Glu | Glu | Trp |
| | | 130 | | | | | 135 | | | | | 140 | | | |

| Gly | Val | Gln | Tyr | Val | Glu | Thr | Ser | Ala | Lys | Thr | Arg | Ala | Asn | Val | Asp |
| 145 | | | | | 150 | | | | | 155 | | | | | 160 |

| Lys | Val | Phe | Phe | Asp | Leu | Met | Arg | Glu | Val | Arg | Ala | Lys | Lys | Met | Ser |
| | | | | 165 | | | | | 170 | | | | | 175 | |

| Glu | Asn | Lys | Asp | Lys | Asn | Gly | Lys | Lys | Ser | Ser | Arg | Asn | Lys | Lys | Ser |
| | | | 180 | | | | | 185 | | | | | 190 | | |

| Leu | Arg | Glu | Arg | Cys | Cys | Ile | Leu |
| | | | 195 | | | | 200 |

(2) INFORMATION FOR SEQ ID NO:34:

(i) SEQUENCE CHARACTERISTICS:
(A) LENGTH: 194 amino acids
(B) TYPE: amino acid
(C) STRANDEDNESS: single
(D) TOPOLOGY: linear (ii) MOLECULE TYPE: protein (iii) HYPOTHETICAL: NO (vi) ORIGINAL SOURCE:
(A) ORGANISM: Discopyge ommata (xi) SEQUENCE DESCRIPTION: SEQ ID NO:34:

| Met | Ala | Lys | Lys | Thr | Tyr | Asp | Leu | Leu | Phe | Lys | Leu | Leu | Leu | Ile | Gly |
|---|---|---|---|---|---|---|---|---|---|---|---|---|---|---|---|
| 1 | | | | 5 | | | | | 10 | | | | | 15 | |

| Asp | Ser | Gly | Val | Gly | Lys | Thr | Cys | Val | Leu | Phe | Arg | Phe | Ser | Asp | Asp |
| | | | 20 | | | | | 25 | | | | | 30 | | |

| Ala | Phe | Asn | Thr | Thr | Phe | Ile | Ser | Thr | Ile | Gly | Ile | Asp | Phe | Lys | Ile |
| | | | | 35 | | | | | 40 | | | | | 45 | |

-continued

```
Lys  Thr  Val  Glu  Leu  His  Gly  Lys  Lys  Ile  Lys  Leu  Gln  Ile  Trp  Asp
     50                  55                       60

Thr  Ala  Gly  Gln  Glu  Arg  Phe  His  Thr  Ile  Thr  Ser  Tyr  Tyr  Arg  Gly
65                       70                  75                            80

Ala  Met  Gly  Ile  Met  Leu  Val  Tyr  Asp  Ile  Thr  Asn  Ala  Lys  Ser  Phe
               85                       90                            95

Glu  Asn  Ile  Ser  Lys  Trp  Leu  Arg  Asn  Ile  Asp  Glu  His  Ala  Asn  Glu
               100                      105                      110

Asp  Val  Glu  Arg  Met  Leu  Leu  Gly  Asn  Lys  Asp  Met  Glu  Asp  Lys  Arg
               115                      120                      125

Val  Val  Leu  Lys  Ser  Lys  Gly  Gln  Ile  Ala  Glu  His  Ala  Ile  Arg  Phe
     130                      135                      140

Phe  Glu  Thr  Ser  Ala  Lys  Ala  Asn  Ile  Asn  Ile  Glu  Lys  Ala  Phe  Leu
145                      150                      155                           160

Thr  Leu  Ala  Glu  Asp  Ile  Leu  Gln  Lys  Thr  Pro  Val  Lys  Glu  Pro  Asp
               165                      170                      175

Arg  Glu  Asn  Val  Asp  Ile  Ser  Thr  Gly  Gly  Gly  Leu  Lys  Lys  Cys
               180                      185                      190

Cys  Ser
```

( 2 ) INFORMATION FOR SEQ ID NO:35:

( i ) SEQUENCE CHARACTERISTICS:
( A ) LENGTH: 207 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( v i ) ORIGINAL SOURCE:
( A ) ORGANISM: Discopyge ommata ( x i ) SEQUENCE DESCRIPTION: SEQ ID NO:35:

```
Met  Lys  Thr  Tyr  Asp  Tyr  Leu  Phe  Lys  Leu  Leu  Leu  Ile  Gly  Asp  Ser
1                   5                        10                      15

Gly  Val  Gly  Lys  Thr  Cys  Leu  Leu  Phe  Arg  Phe  Ser  Glu  Asp  Ala  Phe
               20                       25                      30

Asn  Thr  Thr  Phe  Ile  Ser  Thr  Ile  Gly  Ile  Asp  Phe  Lys  Ile  Arg  Thr
          35                       40                      45

Val  Glu  Leu  Asp  Gly  Lys  Lys  Ile  Lys  Leu  Gln  Ile  Trp  Asp  Thr  Ala
     50                       55                      60

Gly  Gln  Glu  Arg  Phe  Arg  Thr  Ile  Thr  Ala  Tyr  Tyr  Arg  Gly  Ala  Met
65                  70                       75                            80

Gly  Ile  Met  Lys  Val  Asp  Ile  Thr  Asn  Glu  Lys  Ser  Phe  Asp  Asn  Ile
               85                       90                      95

Lys  Asn  Trp  Ile  Arg  Asn  Ile  Glu  Glu  His  Ala  Ser  Ser  Asp  Val  Glu
               100                      105                      110

Arg  Met  Ile  Leu  Gly  Asn  Lys  Cys  Asp  Met  Asn  Glu  Lys  Arg  Gln  Val
               115                      120                      125

Ser  Lys  Glu  Arg  Gly  Glu  Lys  Leu  Ala  Ile  Asp  Tyr  Gly  Ile  Lys  Phe
     130                      135                      140

Leu  Glu  Thr  Ser  Ala  Lys  Ser  Ser  Ile  Asn  Val  Glu  Glu  Ala  Phe  Ile
145                      150                      155                           160

Thr  Leu  Ala  Arg  Asp  Ile  Met  Thr  Lys  Leu  Asn  Lys  Lys  Met  Asn  Glu
               165                      170                      175
```

|     |     |     |     |     |     |     |     |     |     |     |     |     |     |     |
| --- | --- | --- | --- | --- | --- | --- | --- | --- | --- | --- | --- | --- | --- | --- |
| Asn | Ser | Leu | Gln | Glu | Ala | Val | Asp | Lys | Leu | Lys | Ser | Pro | Pro | Lys | Lys |
|     |     |     |     | 180 |     |     |     | 185 |     |     |     | 190 |     |     |
| Pro | Ser | Gln | Lys | Lys | Lys | Gln | Leu | Ser | Phe | Arg | Cys | Ser | Leu | Leu |
|     |     | 195 |     |     |     |     | 200 |     |     |     |     | 205 |     |     |

( 2 ) INFORMATION FOR SEQ ID NO:36:

( i ) SEQUENCE CHARACTERISTICS:
        ( A ) LENGTH: 213 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Discopyge ommata ( x i ) SEQUENCE DESCRIPTION: SEQ ID NO:36:

|     |     |     |     |     |     |     |     |     |     |     |     |     |     |     |     |
| --- | --- | --- | --- | --- | --- | --- | --- | --- | --- | --- | --- | --- | --- | --- | --- |
| Met | Gly | Thr | Arg | Asp | Asp | Glu | Tyr | Asp | Tyr | Leu | Phe | Lys | Val | Val | Leu |
| 1   |     |     |     | 5   |     |     |     |     | 10  |     |     |     |     | 15  |     |
| Ile | Gly | Asp | Ser | Gly | Val | Gly | Lys | Ser | Asn | Leu | Leu | Ser | Arg | Phe | Thr |
|     |     |     | 20  |     |     |     |     | 25  |     |     |     |     | 30  |     |     |
| Arg | Glu | Phe | Asn | Leu | Glu | Ser | Lys | Ser | Thr | Ile | Gly | Val | Glu | Phe | Ala |
|     |     | 35  |     |     |     |     | 40  |     |     |     |     | 45  |     |     |     |
| Thr | Arg | Ser | Ile | Gln | Val | Asp | Gly | Lys | Thr | Ile | Lys | Gln | Ile | Trp | Asp |
|     | 50  |     |     |     |     | 55  |     |     |     |     | 60  |     |     |     |     |
| Thr | Gly | Gln | Glu | Arg | Tyr | Arg | Ala | Ile | Thr | Ser | Ala | Tyr | Tyr | Arg | Gly |
| 65  |     |     |     |     | 70  |     |     |     |     | 75  |     |     |     |     | 80  |
| Ala | Val | Gly | Ala | Leu | Leu | Val | Tyr | Asp | Ile | Ala | Lys | His | Leu | Thr | Tyr |
|     |     |     |     | 85  |     |     |     |     | 90  |     |     |     |     | 95  |     |
| Glu | Asn | Val | Glu | Arg | Trp | Leu | Lys | Glu | Leu | Arg | Asp | His | Ala | Asp | Asn |
|     |     |     | 100 |     |     |     |     | 105 |     |     |     |     | 110 |     |     |
| Asn | Ile | Val | Ile | Met | Leu | Val | Gly | Asn | Lys | Ser | Asp | Leu | Arg | His | Leu |
|     |     | 115 |     |     |     |     | 120 |     |     |     |     | 125 |     |     |     |
| Arg | Val | Pro | Thr | Asp | Ala | Arg | Ala | Phe | Ala | Glu | Lys | Asn | Asn | Leu | Ser |
|     | 130 |     |     |     |     | 135 |     |     |     |     | 140 |     |     |     |     |
| Phe | Ile | Glu | Thr | Ser | Ala | Leu | Asp | Ser | Thr | Asn | Val | Glu | Glu | Ala | Phe |
| 145 |     |     |     |     | 150 |     |     |     |     | 155 |     |     |     |     | 160 |
| Lys | Asn | Ile | Leu | Thr | Glu | Ile | Tyr | Arg | Ile | Val | Ser | Gln | Lys | Gln | Ile |
|     |     |     |     | 165 |     |     |     |     | 170 |     |     |     |     | 175 |     |
| Ser | Asp | Arg | Ser | Ala | His | Asp | Glu | Ser | Pro | Gly | Asn | Asn | Val | Val | Asp |
|     |     |     | 180 |     |     |     |     | 185 |     |     |     |     | 190 |     |     |
| Ile | Ser | Val | Pro | Pro | Thr | Thr | Asp | Gly | Gln | Lys | Ser | Asn | Lys | Leu | Gln |
|     |     | 195 |     |     |     |     | 200 |     |     |     |     | 205 |     |     |     |
| Cys | Cys | Gln | Asn | Met |
|     | 210 |     |     |     |

( 2 ) INFORMATION FOR SEQ ID NO:37:

( i ) SEQUENCE CHARACTERISTICS:
        ( A ) LENGTH: 184 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v i ) ORIGINAL SOURCE:

(A) ORGANISM: Dictyostelium discoideum (xi) SEQUENCE DESCRIPTION: SEQ ID NO:37:

| Met | Pro | Leu | Arg | Phe | Lys | Ile | Val | Val | Leu | Gly | Ser | Gly | Gly | Val | Gly |
|---|---|---|---|---|---|---|---|---|---|---|---|---|---|---|---|
| 1 | | | | 5 | | | | | 10 | | | | | 15 | |
| Lys | Ser | Ala | Leu | Thr | Val | Gln | Phe | Val | Gln | Gly | Ile | Phe | Val | Glu | Lys |
| | | | 20 | | | | 25 | | | | | 30 | | | |
| Tyr | Asp | Pro | Thr | Ile | Glu | Asp | Ser | Tyr | Arg | Lys | Gln | Val | Glu | Val | Asp |
| | | 35 | | | | | 40 | | | | | 45 | | | |
| Ser | Asn | Gln | Cys | Met | Leu | Glu | Ile | Leu | Asp | Thr | Ala | Gly | Thr | Glu | Gln |
| | 50 | | | | | 55 | | | | | 60 | | | | |
| Phe | Thr | Met | Arg | Asp | Leu | Tyr | Met | Lys | Asn | Gly | Gln | Gly | Phe | Val | Leu |
| 65 | | | | | 70 | | | | | 75 | | | | | 80 |
| Val | Tyr | Ser | Ile | Ile | Ser | Asn | Ser | Thr | Phe | Asn | Glu | Leu | Pro | Asp | Leu |
| | | | | 85 | | | | | 90 | | | | | 95 | |
| Arg | Glu | Gln | Ile | Leu | Arg | Val | Lys | Asp | Cys | Glu | Asp | Val | Pro | Met | Val |
| | | | 100 | | | | | 105 | | | | | 110 | | |
| Leu | Val | Gly | Asn | Lys | Cys | Asp | Leu | His | Asp | Gln | Arg | Val | Ile | Ser | Thr |
| | | 115 | | | | | 120 | | | | | 125 | | | |
| Glu | Gln | Gly | Glu | Glu | Leu | Ala | Arg | Lys | Phe | Gly | Asp | Cys | Tyr | Phe | Leu |
| | 130 | | | | | 135 | | | | | 140 | | | | |
| Glu | Ala | Ser | Ala | Lys | Asn | Lys | Val | Asn | Val | Glu | Gln | Ile | Phe | Tyr | Asn |
| 145 | | | | | 150 | | | | | 155 | | | | | 160 |
| Leu | Ile | Arg | Gln | Ile | Asn | Arg | Lys | Asn | Pro | Val | Gly | Pro | Pro | Ser | Lys |
| | | | | 165 | | | | | 170 | | | | | 175 | |
| Ala | Lys | Ser | Lys | Cys | Ala | Leu | Leu | | | | | | | | |
| | | | 180 | | | | | | | | | | | | |

(2) INFORMATION FOR SEQ ID NO:38:

(i) SEQUENCE CHARACTERISTICS:
        (A) LENGTH: 179 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Homo sapiens (xi) SEQUENCE DESCRIPTION: SEQ ID NO:38:

| Met | Arg | Glu | Tyr | Lys | Val | Val | Val | Leu | Gly | Ser | Gly | Gly | Val | Gly | Lys |
|---|---|---|---|---|---|---|---|---|---|---|---|---|---|---|---|
| 1 | | | | 5 | | | | | 10 | | | | | 15 | |
| Ser | Ala | Leu | Thr | Val | Gln | Phe | Val | Thr | Gly | Thr | Phe | Ile | Glu | Lys | Tyr |
| | | | 20 | | | | 25 | | | | | 30 | | | |
| Asp | Pro | Thr | Ile | Glu | Asp | Phe | Tyr | Arg | Lys | Glu | Ile | Glu | Val | Asp | Ser |
| | | 35 | | | | | 40 | | | | | 45 | | | |
| Ser | Pro | Ser | Val | Leu | Glu | Ile | Leu | Asp | Thr | Ala | Gly | Thr | Glu | Gln | Phe |
| | 50 | | | | | 55 | | | | | 60 | | | | |
| Ala | Ser | Arg | Asp | Leu | Tyr | Ile | Lys | Asn | Gly | Gln | Gly | Phe | Ile | Leu | Val |
| 65 | | | | | 70 | | | | | 75 | | | | | 80 |
| Tyr | Ser | Leu | Val | Asn | Gln | Gln | Phe | Gln | Asp | Ile | Lys | Pro | Met | Arg | Asp |
| | | | | 85 | | | | | 90 | | | | | 95 | |
| Gln | Ile | Ile | Arg | Val | Lys | Tyr | Glu | Lys | Val | Pro | Val | Ile | Leu | Val | Gly |
| | | | 100 | | | | | 105 | | | | | 110 | | |
| Asn | Lys | Val | Asp | Leu | Glu | Ser | Glu | Arg | Glu | Val | Ser | Ser | Ser | Glu | Gly |

| | | | | 115 | | | | | 120 | | | | | 125 | |
|---|---|---|---|---|---|---|---|---|---|---|---|---|---|---|---|
| Arg | Ala | Leu | Ala | Glu | Glu | Trp | Gly | Cys | Pro | Phe | Met | Glu | Thr | Ser | Ala |
| | | 130 | | | | 135 | | | | | 140 | | | | |
| Lys | Ser | Lys | Thr | Met | Val | Asp | Glu | Leu | Phe | Ala | Glu | Ile | Val | Arg | Gln |
| 145 | | | | | 150 | | | | | 155 | | | | | 160 |
| Met | Asn | Tyr | Ala | Ala | Gln | Pro | Asp | Lys | Asp | Pro | Cys | Cys | Ser | Ala | |
| | | | | 165 | | | | | 170 | | | | | 175 | |
| Cys | Asn | Gln | | | | | | | | | | | | | |

( 2 ) INFORMATION FOR SEQ ID NO:39:

( i ) SEQUENCE CHARACTERISTICS:
        ( A ) LENGTH: 183 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:39:

| Met | Arg | Glu | Tyr | Lys | Val | Val | Val | Leu | Gly | Ser | Gly | Gly | Val | Gly | Lys |
|---|---|---|---|---|---|---|---|---|---|---|---|---|---|---|---|
| 1 | | | | 5 | | | | | 10 | | | | | 15 | |
| Ser | Ala | Leu | Thr | Val | Gln | Phe | Val | Thr | Gly | Ser | Phe | Ile | Glu | Lys | Tyr |
| | | | 20 | | | | | 25 | | | | | 30 | | |
| Asp | Pro | Thr | Ile | Glu | Asp | Phe | Tyr | Arg | Lys | Glu | Ile | Glu | Val | Asp | Ser |
| | | 35 | | | | | 40 | | | | | 45 | | | |
| Ser | Pro | Ser | Val | Leu | Glu | Ile | Leu | Asp | Thr | Ala | Gly | Thr | Glu | Gln | Phe |
| | 50 | | | | | 55 | | | | | 60 | | | | |
| Ala | Ser | Met | Arg | Asp | Leu | Tyr | Ile | Lys | Asn | Gly | Gln | Gly | Phe | Ile | Leu |
| 65 | | | | | 70 | | | | | 75 | | | | | 80 |
| Val | Tyr | Ser | Leu | Val | Asn | Gln | Gln | Ser | Phe | Gln | Asp | Ile | Lys | Pro | Met |
| | | | | 85 | | | | | 90 | | | | | 95 | |
| Arg | Asp | Gln | Ile | Ile | Arg | Val | Lys | Arg | Tyr | Glu | Arg | Val | Pro | Met | Ile |
| | | | 100 | | | | | 105 | | | | | 110 | | |
| Leu | Val | Gly | Asn | Lys | Val | Asp | Leu | Glu | Gly | Glu | Arg | Glu | Val | Ser | Tyr |
| | | | 115 | | | | | 120 | | | | | 125 | | |
| Gly | Glu | Gly | Lys | Ala | Leu | Ala | Glu | Glu | Trp | Ser | Cys | Pro | Phe | Met | Glu |
| | | 130 | | | | 135 | | | | | 140 | | | | |
| Thr | Ser | Ala | Lys | Asn | Lys | Ala | Ser | Val | Asp | Glu | Leu | Phe | Ala | Glu | Ile |
| 145 | | | | | 150 | | | | | 155 | | | | | 160 |
| Val | Arg | Gln | Met | Asn | Tyr | Ala | Ala | Gln | Ser | Asn | Gly | Asp | Glu | Gly | Cys |
| | | | | 165 | | | | | 170 | | | | | 175 | |
| Cys | Ser | Ala | Cys | Val | Ile | Leu | | | | | | | | | |
| | | | 180 | | | | | | | | | | | | |

( 2 ) INFORMATION FOR SEQ ID NO:40:

( i ) SEQUENCE CHARACTERISTICS:
        ( A ) LENGTH: 184 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO (vi) ORIGINAL SOURCE:
    (A) ORGANISM: Discopyge ommata (xi) SEQUENCE DESCRIPTION: SEQ ID NO:40:

| Met | Arg | Glu | Tyr | Lys | Leu | Val | Val | Leu | Gly | Ser | Gly | Gly | Val | Gly | Lys |
|---|---|---|---|---|---|---|---|---|---|---|---|---|---|---|---|
| 1 | | | | 5 | | | | | 10 | | | | | 15 | |
| Ser | Ala | Leu | Thr | Val | Gln | Phe | Val | Gln | Gly | Ile | Phe | Val | Glu | Lys | Tyr |
| | | | 20 | | | | | 25 | | | | | 30 | | |
| Asp | Pro | Thr | Ile | Glu | Asp | Ser | Tyr | Arg | Lys | Gln | Val | Glu | Val | Asp | Cys |
| | | 35 | | | | | 40 | | | | | 45 | | | |
| Gln | Pro | Cys | Met | Leu | Glu | Ile | Leu | Asp | Thr | Ala | Gly | Thr | Glu | Gln | Phe |
| | 50 | | | | | 55 | | | | | 60 | | | | |
| Thr | Ala | Met | Arg | Asp | Leu | Tyr | Met | Lys | Asn | Gly | Gln | Gly | Phe | Ala | Leu |
| 65 | | | | | 70 | | | | | 75 | | | | | 80 |
| Val | Tyr | Ser | Ile | Thr | Ala | Gln | Ser | Thr | Phe | Asn | Asp | Leu | Gln | Asp | Leu |
| | | | | 85 | | | | | 90 | | | | | 95 | |
| Arg | Glu | Gln | Ile | Leu | Arg | Val | Lys | Asp | Thr | Glu | Asp | Val | Pro | Met | Ile |
| | | | | 100 | | | | | 105 | | | | | 110 | |
| Leu | Val | Gly | Asn | Lys | Cys | Asp | Leu | Glu | Asp | Glu | Arg | Val | Val | Gly | Lys |
| | | | 115 | | | | | 120 | | | | | 125 | | |
| Glu | Gln | Gly | Gln | Asn | Leu | Ala | Arg | Gln | Trp | Asn | Asn | Cys | Ala | Phe | Leu |
| | | 130 | | | | | 135 | | | | | 140 | | | |
| Glu | Ser | Ser | Ala | Lys | Ser | Lys | Ile | Asn | Val | Asn | Glu | Ile | Phe | Tyr | Asp |
| 145 | | | | | 150 | | | | | 155 | | | | | 160 |
| Leu | Val | Arg | Gln | Ile | Asn | Arg | Lys | Ala | Pro | Val | Glu | Lys | Cys | Lys | Lys |
| | | | | 165 | | | | | 170 | | | | | 175 | |
| Lys | Lys | Ser | Gln | Cys | Thr | Leu | Leu | | | | | | | | |
| | | | 180 | | | | | | | | | | | | |

(2) INFORMATION FOR SEQ ID NO:41:

(i) SEQUENCE CHARACTERISTICS:
      (A) LENGTH: 180 amino acids
      (B) TYPE: amino acid
      (C) STRANDEDNESS: single
      (D) TOPOLOGY: linear (ii) MOLECULE TYPE: protein (iii) HYPOTHETICAL: NO (vi) ORIGINAL SOURCE:
      (A) ORGANISM: Homo sapiens (xi) SEQUENCE DESCRIPTION: SEQ ID NO:41:

| Met | Arg | Glu | Tyr | Lys | Leu | Val | Val | Gly | Ser | Gly | Gly | Val | Gly | Lys | Ser |
|---|---|---|---|---|---|---|---|---|---|---|---|---|---|---|---|
| 1 | | | | 5 | | | | | 10 | | | | | 15 | |
| Ala | Leu | Thr | Val | Gln | Phe | Val | Gln | Gly | Phe | Val | Glu | Lys | Tyr | Asp | Pro |
| | | | 20 | | | | | 25 | | | | | 30 | | |
| Thr | Ile | Glu | Asp | Ser | Tyr | Arg | Lys | Gln | Val | Glu | Val | Asp | Cys | Gln | Gln |
| | | 35 | | | | | 40 | | | | | 45 | | | |
| Cys | Met | Leu | Glu | Asp | Thr | Ala | Gly | Thr | Glu | Gln | Phe | Thr | Ala | Met | Arg |
| | 50 | | | | | 55 | | | | | 60 | | | | |
| Asp | Leu | Tyr | Met | Lys | Asn | Gly | Gln | Gly | Phe | Ala | Leu | Val | Tyr | Ser | Ile |
| 65 | | | | | 70 | | | | | 75 | | | | | 80 |
| Thr | Ala | Gln | Ser | Thr | Phe | Asn | Asp | Leu | Gln | Asp | Leu | Arg | Glu | Gln | Ile |
| | | | | 85 | | | | | 90 | | | | | 95 | |
| Leu | Arg | Val | Lys | Asp | Thr | Glu | Asp | Val | Pro | Met | Ile | Leu | Val | Gly | Asn |
| | | | | 100 | | | | | 105 | | | | | 110 | |

```
     Lys  Cys  Asp  Leu  Glu  Asp  Glu  Arg  Val  Val  Gly  Lys  Glu  Gln  Gly  Gln
               115                      120                      125

Asn  Leu  Ala  Arg  Gln  Trp  Cys  Asn  Cys  Ala  Phe  Leu  Glu  Ser  Ser  Ala
               130                 135                      140

Lys  Ser  Lys  Ile  Asn  Val  Asn  Glu  Ile  Phe  Tyr  Asp  Leu  Val  Arg  Gln
     145                      150                      155                           160

Ile  Asn  Arg  Lys  Thr  Pro  Val  Glu  Lys  Lys  Pro  Lys  Lys  Lys  Ser
                         165                      170                      175

Cys  Leu  Leu  Leu
                    180
```

(2) INFORMATION FOR SEQ ID NO:42:

(i) SEQUENCE CHARACTERISTICS:
        (A) LENGTH: 179 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Homo sapiens (xi) SEQUENCE DESCRIPTION: SEQ ID NO:42:

```
     Met  Arg  Glu  Tyr  Lys  Leu  Val  Val  Leu  Gly  Ser  Gly  Gly  Val  Gly  Lys
     1                   5                        10                       15

Ser  Ala  Leu  Thr  Val  Gln  Phe  Val  Gln  Gly  Ile  Phe  Val  Glu  Lys  Tyr
                    20                  25                       30

Asp  Pro  Thr  Ile  Glu  Asp  Ser  Tyr  Arg  Lys  Gln  Val  Glu  Val  Asp  Ala
                    35                  40                       45

Gln  Gln  Cys  Met  Leu  Glu  Ile  Leu  Asp  Thr  Ala  Gly  Thr  Glu  Gln  Phe
               50                  55                       60

Thr  Ala  Met  Arg  Asp  Leu  Tyr  Met  Lys  Asn  Gly  Gln  Gly  Phe  Ala  Leu
     65                       70                       75                            80

Val  Tyr  Ser  Ile  Thr  Ala  Gln  Ser  Thr  Phe  Asn  Asp  Leu  Gln  Asp  Leu
                         85                       90                           95

Arg  Glu  Gln  Ile  Leu  Arg  Val  Lys  Asp  Thr  Asp  Asp  Val  Pro  Met  Ile
                    100                     105                      110

Leu  Val  Gly  Asn  Lys  Cys  Asp  Leu  Glu  Asp  Glu  Arg  Val  Val  Gly  Lys
                    115                     120                      125

Glu  Gln  Gly  Gln  Asn  Leu  Ala  Arg  Gln  Trp  Asn  Asn  Cys  Ala  Phe  Leu
               130                     135                      140

Glu  Ser  Ser  Ala  Lys  Ser  Lys  Ile  Asn  Val  Glu  Ile  Phe  Tyr  Asp  Leu
     145                      150                      155                           160

Val  Arg  Gln  Ile  Asn  Arg  Lys  Thr  Pro  Val  Pro  Gly  Lys  Ala  Arg  Lys
                         165                      170                      175

Lys  Ser  Ser
```

(2) INFORMATION FOR SEQ ID NO:43:

(i) SEQUENCE CHARACTERISTICS:
        (A) LENGTH: 184 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
  (A) ORGANISM: Drosophila melanogaster (xi) SEQUENCE DESCRIPTION: SEQ ID NO:43:

| Met | Arg | Glu | Tyr | Lys | Ile | Val | Val | Leu | Gly | Ser | Gly | Gly | Val | Gly | Lys |
|---|---|---|---|---|---|---|---|---|---|---|---|---|---|---|---|
| 1 | | | | 5 | | | | | 10 | | | | | | 15 |
| Ser | Ala | Leu | Thr | Val | Gln | Phe | Val | Gln | Cys | Ile | Phe | Val | Glu | Lys | Tyr |
| | | | 20 | | | | | 25 | | | | | 30 | | |
| Asp | Pro | Thr | Ile | Glu | Asp | Ser | Tyr | Arg | Lys | Gln | Val | Glu | Val | Asp | Gly |
| | | 35 | | | | | 40 | | | | | 45 | | | |
| Gln | Gln | Cys | Met | Leu | Glu | Ile | Leu | Asp | Thr | Ala | Gly | Thr | Glu | Gln | Phe |
| | 50 | | | | | 55 | | | | | 60 | | | | |
| Thr | Ala | Met | Arg | Asp | Leu | Tyr | Met | Lys | Asn | Gly | Gln | Gly | Phe | Val | Leu |
| 65 | | | | | 70 | | | | | 75 | | | | | 80 |
| Val | Tyr | Ser | Ile | Thr | Ala | Gln | Ser | Thr | Phe | Asn | Asp | Leu | Gln | Asp | Leu |
| | | | | 85 | | | | | 90 | | | | | 95 | |
| Arg | Glu | Gln | Ile | Leu | Arg | Val | Lys | Asp | Thr | Asp | Asp | Val | Pro | Met | Val |
| | | | 100 | | | | | 105 | | | | | 110 | | |
| Leu | Val | Gly | Asn | Lys | Cys | Asp | Leu | Glu | Glu | Glu | Arg | Val | Val | Gly | Lys |
| | | | 115 | | | | | 120 | | | | | 125 | | |
| Glu | Leu | Gly | Lys | Asn | Leu | Ala | Thr | Gln | Phe | Asn | Cys | Ala | Phe | Met | Glu |
| | | 130 | | | | | 135 | | | | | 140 | | | |
| Thr | Ser | Ala | Lys | Ala | Lys | Val | Asn | Val | Asn | Asp | Ile | Phe | Tyr | Asp | Leu |
| 145 | | | | | 150 | | | | | 155 | | | | | 160 |
| Val | Arg | Gln | Ile | Asn | Lys | Lys | Ser | Pro | Glu | Lys | Lys | Gln | Lys | Lys | Pro |
| | | | | 165 | | | | | 170 | | | | | 175 | |
| Lys | Lys | Ser | Leu | Cys | Val | Leu | Leu | | | | | | | | |
| | | | 180 | | | | | | | | | | | | |

(2) INFORMATION FOR SEQ ID NO:44:

(i) SEQUENCE CHARACTERISTICS:
    (A) LENGTH: 182 amino acids
    (B) TYPE: amino acid
    (C) STRANDEDNESS: single
    (D) TOPOLOGY: linear (ii) MOLECULE TYPE: protein (iii) HYPOTHETICAL: NO (vi) ORIGINAL SOURCE:
    (A) ORGANISM: Dictyostelium discoideum (xi) SEQUENCE DESCRIPTION: SEQ ID NO:44:

| Met | Thr | Glu | Tyr | Lys | Leu | Val | Ile | Val | Gly | Gly | Gly | Gly | Val | Gly | Lys |
|---|---|---|---|---|---|---|---|---|---|---|---|---|---|---|---|
| 1 | | | | 5 | | | | | 10 | | | | | | 15 |
| Ser | Leu | Thr | Ile | Gln | Leu | Ile | Gln | Asn | His | Phe | Asp | Glu | Tyr | Asp | Pro |
| | | | 20 | | | | | 25 | | | | | 30 | | |
| Thr | Ile | Glu | Asp | Ser | Tyr | Arg | Lys | Gln | Val | Ser | Ile | Asp | Asp | Glu | Thr |
| | | 35 | | | | | 40 | | | | | 45 | | | |
| Cys | Leu | Leu | Ile | Leu | Asp | Thr | Ala | Gly | Gln | Glu | Glu | Ser | Ala | Met | Arg |
| | 50 | | | | | 55 | | | | | 60 | | | | |
| Asp | Gln | Tyr | Met | Arg | Thr | Gly | Gln | Gly | Phe | Leu | Cys | Val | Tyr | Ser | Ile |
| 65 | | | | | 70 | | | | | 75 | | | | | 80 |
| Thr | Ser | Arg | Ser | Ser | Tyr | Asp | Glu | Ile | Ala | Ser | Phe | Arg | Glu | Gln | Ile |
| | | | | 85 | | | | | 90 | | | | | 95 | |
| Leu | Arg | Val | Lys | Asp | Lys | Asp | Arg | Val | Pro | Leu | Ile | Leu | Val | Gly | Asn |
| | | | 100 | | | | | 105 | | | | | 110 | | |

5,840,683

```
Lys Ala Asp Leu Asp His Glu Arg Gln Val Ser Val Asn Glu Gly Gln
        115                 120                 125

Glu Leu Ala Lys Asp Ser Leu Ser Phe His Glu Ser Ser Ala Lys Ser
    130                 135                 140

Arg Ile Asn Val Glu Glu Ala Phe Tyr Ser Leu Val Arg Glu Ile Arg
145                 150                 155                 160

Lys Glu Leu Lys Gly Asp Gln Ser Ser Gly Lys Ala Gln Lys Lys Lys
                165                 170                 175

Lys Gln Cys Leu Ile Leu
            180
```

( 2 ) INFORMATION FOR SEQ ID NO:45:

( i ) SEQUENCE CHARACTERISTICS:
        ( A ) LENGTH: 190 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Dictyostelium discoideum ( x i ) SEQUENCE DESCRIPTION: SEQ ID NO:45:

```
Met Ser Val Ser Asn Glu Tyr Lys Leu Val Val Gly Gly Gly Gly Val
1               5                   10                  15

Gly Lys Ser Ala Leu Thr Ile Gln Phe Gln Asn His Phe Ile Glu Glu
                20                  25                  30

Tyr Asp Pro Thr Ile Glu Asp Ser Tyr Arg Arg Gln Cys Gln Val Asp
            35                  40                  45

Glu Asp Thr Cys Leu Leu Asp Ile Leu Asp Thr Ala Gly Gln Asp Asp
        50                  55                  60

Tyr Ser Met Arg Asp Gln Tyr Met Arg Thr Gly Gln Gly Phe Leu Val
65                  70                  75                  80

Tyr Asp Val Ser Arg Thr Ser Phe Glu Glu Ile Asn Val Val Glu Gln
                85                  90                  95

Ile Arg Val Lys Asp Asn Asp Lys Val Pro Ile Val Leu Val Gly Asn
            100                 105                 110

Lys Cys Asp Leu Glu Asn Leu Arg Glu Val Thr Glu Gly Glu Gly Ser
        115                 120                 125

Glu Leu Ala Lys Ser Phe Ser Val Pro Phe Leu Glu Thr Ser Ala Lys
    130                 135                 140

Lys Arg Leu Asn Val Asp Glu Cys Phe Phe Glu Val Val Arg Glu Ile
145                 150                 155                 160

Lys Lys Ser Leu Lys Glu Pro Gly Arg Ser Lys Lys Asp Lys Lys Gly
                165                 170                 175

Gly Ile Leu Lys Lys Phe Lys Gly Gly Asp Cys Leu Ile Leu
            180                 185                 190
```

( 2 ) INFORMATION FOR SEQ ID NO:46:

( i ) SEQUENCE CHARACTERISTICS:
        ( A ) LENGTH: 188 amino acids
        ( B ) TYPE: amino acid
        ( C ) STRANDEDNESS: single
        ( D ) TOPOLOGY: linear ( i i ) MOLECULE TYPE: protein (iii) HYPOTHETICAL: NO (vi) ORIGINAL SOURCE:
   (A) ORGANISM: Dictyostelium discoideum (xi) SEQUENCE DESCRIPTION: SEQ ID NO:46:

| Met | Ser | Lys | Leu | Leu | Lys | Leu | Val | Ile | Val | Gly | Asp | Gly | Gly | Val | Gly |
|---|---|---|---|---|---|---|---|---|---|---|---|---|---|---|---|
| 1 | | | | 5 | | | | | 10 | | | | | 15 | |
| Lys | Ser | Ala | Leu | Thr | Ile | Gln | Leu | Thr | Gln | Asn | Gln | Phe | Ile | Ala | Glu |
| | | | 20 | | | | 25 | | | | | | 30 | | |
| Tyr | Asp | Pro | Thr | Ile | Glu | Asn | Ser | Tyr | Arg | Lys | Gln | Val | Asn | Ile | Asp |
| | | 35 | | | | | 40 | | | | | 45 | | | |
| Glu | Glu | Val | Tyr | Met | Leu | Asp | Ile | Leu | Asp | Thr | Ala | Gly | Gln | Glu | Glu |
| | 50 | | | | | 55 | | | | | 60 | | | | |
| Tyr | Ser | Ala | Met | Arg | Asp | Gln | Tyr | Ile | Arg | Ser | Gly | Arg | Gly | Phe | Leu |
| 65 | | | | | 70 | | | | | 75 | | | | | 80 |
| Ile | Val | Tyr | Ser | Ile | Ile | Ser | Arg | Ala | Ser | Phe | Glu | Ala | Val | Thr | Thr |
| | | | | 85 | | | | | 90 | | | | | 95 | |
| Phe | Arg | Glu | Gln | Ile | Leu | Arg | Val | Lys | Asp | Leu | Ser | Thr | Tyr | Pro | Ile |
| | | | 100 | | | | | 105 | | | | | 110 | | |
| Val | Ile | Ile | Gly | Asn | Lys | Ala | Asp | Leu | Pro | Asp | Lys | Asp | Arg | Lys | Val |
| | | 115 | | | | | 120 | | | | | 125 | | | |
| Pro | Pro | Met | Glu | Gly | Lys | Glu | Leu | Ala | Lys | Phe | Gly | Ala | Pro | Phe | Leu |
| | 130 | | | | | 135 | | | | | 140 | | | | |
| Glu | Thr | Ser | Ala | Lys | Ser | Arg | Val | Asn | Val | Glu | Glu | Ala | Phe | Phe | Thr |
| 145 | | | | | 150 | | | | | 155 | | | | | 160 |
| Leu | Val | Arg | Glu | Ile | Lys | Arg | Trp | Asn | Gln | Asn | Pro | Gln | Asn | Glu | Glu |
| | | | | 165 | | | | | 170 | | | | | 175 | |
| Met | Leu | Pro | Pro | Lys | Lys | Arg | Gly | Cys | Ile | Ile | Leu | | | | |
| | | | 180 | | | | | 185 | | | | | | | |

(2) INFORMATION FOR SEQ ID NO:47:

(i) SEQUENCE CHARACTERISTICS:
      (A) LENGTH: 188 amino acids
      (B) TYPE: amino acid
      (C) STRANDEDNESS: single
      (D) TOPOLOGY: linear (ii) MOLECULE TYPE: protein (iii) HYPOTHETICAL: NO (vi) ORIGINAL SOURCE:
      (A) ORGANISM: Dictyostelium discoideum (xi) SEQUENCE DESCRIPTION: SEQ ID NO:47:

| Met | Glu | Tyr | Lys | Leu | Val | Ile | Val | Gly | Gly | Gly | Gly | Val | Gly | Lys | Ser |
|---|---|---|---|---|---|---|---|---|---|---|---|---|---|---|---|
| 1 | | | | 5 | | | | | 10 | | | | | 15 | |
| Ala | Leu | Thr | Ile | Gln | Leu | Ile | Gln | Asn | His | Phe | Ile | Asp | Glu | Tyr | Asp |
| | | | 20 | | | | 25 | | | | | 30 | | | |
| Pro | Thr | Ile | Glu | Asp | Ser | Tyr | Arg | Lys | Gln | Val | Thr | Ile | Asp | Glu | Glu |
| | | 35 | | | | | 40 | | | | | 45 | | | |
| Thr | Cys | Leu | Leu | Asp | Ile | Leu | Asp | Thr | Ala | Gly | Gln | Glu | Glu | Tyr | Ser |
| | 50 | | | | | 55 | | | | | 60 | | | | |
| Ala | Met | Arg | Asp | Gln | Tyr | Met | Arg | Thr | Gly | Gln | Gly | Phe | Leu | Cys | Val |
| 65 | | | | | 70 | | | | | 75 | | | | | 80 |
| Tyr | Ser | Ile | Thr | Ser | Arg | Ser | Ser | Phe | Asp | Glu | Ile | Ala | Ser | Phe | Arg |
| | | | | 85 | | | | | 90 | | | | | 95 | |

Glu  Gln  Ile  Leu  Arg  Val  Lys  Asp  Lys  Asp  Arg  Val  Pro  Met  Ile  Val
                        100                 105                      110

Val  Gly  Asn  Lys  Cys  Asp  Leu  Glu  Ser  Asp  Arg  Gln  Val  Thr  Thr  Gly
                        115                 120                      125

Glu  Gly  Gln  Asp  Leu  Ala  Lys  Ser  Phe  Gly  Ser  Pro  Phe  Leu  Glu  Thr
                        130                 135                      140

Ser  Ala  Lys  Ile  Arg  Val  Asn  Val  Glu  Glu  Ala  Phe  Tyr  Ser  Leu  Val
         145                           150                 155                      160

Arg  Glu  Ile  Arg  Lys  Asp  Leu  Lys  Gly  Asp  Ser  Lys  Pro  Glu  Lys  Gly
                             165                 170                      175

Lys  Lys  Lys  Arg  Pro  Leu  Lys  Ala  Cys  Thr  Leu  Leu
                             180                 185

( 2 ) INFORMATION FOR SEQ ID NO:48:

( i ) SEQUENCE CHARACTERISTICS:
            ( A ) LENGTH: 204 amino acids
            ( B ) TYPE: amino acid
            ( C ) STRANDEDNESS: single
            ( D ) TOPOLOGY: linear ( i i ) MOLECULE TYPE: protein ( i i i ) HYPOTHETICAL: NO ( v i ) ORIGINAL SOURCE:
            ( A ) ORGANISM: Caenorhabditis elegans ( x i ) SEQUENCE DESCRIPTION: SEQ ID NO:48:

Met  Ser  Ser  Ser  Leu  Gln  Ser  Asn  Arg  Gln  Ser  Leu  Asn  Arg  Lys  Val
         1                   5                   10                      15

Ala  Val  Met  Gly  Tyr  Pro  His  Val  Gly  Lys  Ser  Ala  Leu  Val  Leu  Arg
                        20                  25                       30

Phe  Thr  Gln  Asn  Ile  Phe  Pro  Glu  Arg  Tyr  Glu  Ser  Thr  Ile  Glu  Asp
                        35                  40                       45

Gln  His  Ser  Lys  His  Ile  Ala  Ala  Phe  His  Arg  Asp  Tyr  His  Leu  Arg
              50                       55                  60

Val  Thr  Asp  Thr  Ala  Gly  Gln  Gln  Glu  Tyr  Thr  Val  Phe  Pro  Arg  Ser
         65                           70                  75                       80

Cys  Ser  Leu  Asp  Ile  Asn  Gly  Phe  Ile  Leu  Val  Tyr  Ala  Ile  Asp  Asp
                        85                                90                       95

Arg  Lys  Ser  Phe  Glu  Met  Cys  Ser  Asn  Ile  Tyr  Glu  Lys  Ile  Val  Arg
                        100                 105                      110

Thr  Tyr  Gly  Asp  Thr  Ser  Ile  Pro  Ile  Val  Ile  Val  Gly  Lys  Thr  Asp
                        115                 120                      125

Leu  Ser  Thr  Gln  Val  Val  Arg  Ala  Glu  Glu  Gly  Glu  Glu  Leu  Ala  Arg
              130                      135                 140

Gln  Trp  Asp  Ala  Lys  Phe  Val  Glu  Ile  Thr  Ala  Arg  Glu  Ser  Asn  Arg
         145                           150                 155                      160

Val  His  Glu  Val  Phe  Glu  Leu  Leu  Leu  Arg  Glu  Ile  Glu  Ile  Ser  Arg
                             165                 170                      175

Gly  Asn  Leu  Ser  Pro  Thr  Glu  Arg  Pro  Asn  Gly  Asn  Ser  Pro  Lys  Arg
                        180                 185                      190

Pro  Phe  Lys  Asp  Asp  Gly  Lys  Pro  Cys  Ser  Ile  Ser
                        195                 200

( 2 ) INFORMATION FOR SEQ ID NO:49:

( i ) SEQUENCE CHARACTERISTICS:
            ( A ) LENGTH: 215 amino acids (B) TYPE: amino acid
(C) STRANDEDNESS: single
(D) TOPOLOGY: linear (ii) MOLECULE TYPE: protein (iii) HYPOTHETICAL: NO (vi) ORIGINAL SOURCE:
(A) ORGANISM: Coprinus cinereus (xi) SEQUENCE DESCRIPTION: SEQ ID NO:49:

| Met | Ala | Ala | Arg | Ala | Gln | Phe | Leu | Arg | Glu | Tyr | Lys | Leu | Val | Val | Val |
|---|---|---|---|---|---|---|---|---|---|---|---|---|---|---|---|
| 1 | | | | 5 | | | | | 10 | | | | | 15 | |
| Gly | Gly | Gly | Gly | Val | Gly | Lys | Ser | Ala | Leu | Thr | Ile | Gln | Phe | Ile | Gln |
| | | | 20 | | | | | 25 | | | | | 30 | | |
| Ser | His | Phe | Val | Asp | Glu | Tyr | Asp | Pro | Thr | Ile | Glu | Asp | Ser | Tyr | Arg |
| | | 35 | | | | | 40 | | | | | 45 | | | |
| Lys | Gln | Cys | Ile | Ile | Asp | Asp | Glu | Val | Ala | Leu | Leu | Asp | Val | Leu | Asp |
| | 50 | | | | | 55 | | | | | 60 | | | | |
| Thr | Ala | Gly | Gln | Glu | Glu | Tyr | Gly | Ala | Met | Arg | Glu | Gln | Tyr | Met | Arg |
| 65 | | | | | 70 | | | | | 75 | | | | | 80 |
| Thr | Gly | Glu | Gly | Phe | Leu | Leu | Val | Tyr | Ser | Ile | Thr | Ser | Arg | Asn | Ser |
| | | | | 85 | | | | | 90 | | | | | 95 | |
| Phe | Glu | Glu | Ile | Ser | Ile | Phe | His | Gln | Ile | Leu | Arg | Val | Lys | Asp | |
| | | | 100 | | | | | 105 | | | | | 110 | | |
| Gln | Asp | Ser | Phe | Pro | Val | Ile | Val | Val | Ala | Asn | Lys | Cys | Asp | Leu | Glu |
| | | | 115 | | | | | 120 | | | | | 125 | | |
| Tyr | Glu | Arg | Gln | Val | Gly | Met | Asn | Glu | Gly | Arg | Asp | Leu | Ala | Lys | His |
| | 130 | | | | | 135 | | | | | 140 | | | | |
| Phe | Gly | Cys | Lys | Phe | Ile | Glu | Thr | Ser | Ala | Lys | Gln | Arg | Ile | Asn | Val |
| 145 | | | | | 150 | | | | | 155 | | | | | 160 |
| Asp | Glu | Ala | Phe | Ser | Asn | Leu | Val | Arg | Glu | Ile | Arg | Lys | Tyr | Asn | Arg |
| | | | | 165 | | | | | 170 | | | | | 175 | |
| Glu | Gln | Gln | Thr | Gly | Arg | Pro | Ala | Ile | Ala | Ala | Gly | Gly | Gly | Gly | Pro |
| | | | 180 | | | | | 185 | | | | | 190 | | |
| Ala | Gly | Ser | Tyr | Thr | Gln | Asp | Arg | His | His | Asp | Glu | Ala | Pro | Gly | Cys |
| | | 195 | | | | | 200 | | | | | 205 | | | |
| Cys | Ala | Gly | Cys | Val | Ile | Ala | | | | | | | | | |
| | 210 | | | | | 215 | | | | | | | | | |

(2) INFORMATION FOR SEQ ID NO:50:

(i) SEQUENCE CHARACTERISTICS:
(A) LENGTH: 206 amino acids
(B) TYPE: amino acid
(C) STRANDEDNESS: single
(D) TOPOLOGY: linear (ii) MOLECULE TYPE: protein (iii) HYPOTHETICAL: NO (vi) ORIGINAL SOURCE:
(A) ORGANISM: Geodia cydonium (xi) SEQUENCE DESCRIPTION: SEQ ID NO:50:

| Met | Thr | Glu | Tyr | Lys | Ile | Val | Val | Gly | Gly | Gly | Leu | Val | Gly | Lys | Ser |
|---|---|---|---|---|---|---|---|---|---|---|---|---|---|---|---|
| 1 | | | | 5 | | | | | 10 | | | | | 15 | |
| Ala | Leu | Thr | Leu | Gln | Leu | Val | Gln | Val | Cys | Ile | Lys | Asp | Gln | Tyr | Tyr |
| | | | 20 | | | | | 25 | | | | | 30 | | |
| Leu | Ile | Glu | Phe | Gln | Asn | Asn | Gln | Phe | Gln | Phe | Glu | Asn | Leu | Gln | Asn |

|  | 35 |  |  |  | 40 |  |  |  | 45 |  |  |
|---|---|---|---|---|---|---|---|---|---|---|---|

His Tyr Ile Asp Tyr Asp Pro Thr Val Glu Asp Ser Arg Arg Glu Val
50 55 60

Ser Ile Asp Asp Gln Thr Cys Leu Asn Ile Leu Asp Thr Ala Gly Gln
65 70 75 80

Gln His Ser Asn Ala Gln Ser Met Asp Ala His Trp Ser Thr Val Phe
85 90 95

Val Cys Leu Phe Asn Tyr Phe Asn Ile Thr Ser Met Tyr Asp Glu Ile
100 105 110

Ala Ser Phe Arg Glu Gln Ile Leu Arg Val Lys Asp Gly Ala Lys Asp
115 120 125

Leu Val Pro Leu Ile Leu Ile Asn Lys Ala Asp Leu Asp His Glu
130 135 140

Ser Gln Gly Ser Gly Asn Glu Gly Gln Leu Ala Lys Asp Ser Leu Ser
145 150 155 160

Phe His Gln Ser Ser Ala Lys Ser Arg Ile Asn Leu Glu Glu Ile Pro
165 170 175

Tyr Ser Leu Val Arg Glu Leu Arg Lys Glu Leu Lys Leu Asp Gln Ser
180 185 190

Ser Gly Lys Ala Gln Lys Lys Lys Gln Cys Leu Ile Ile
195 200 205

( 2 ) INFORMATION FOR SEQ ID NO:51:

( i ) SEQUENCE CHARACTERISTICS:
      ( A ) LENGTH: 198 amino acids
      ( B ) TYPE: amino acid
      ( C ) STRANDEDNESS: single
      ( D ) TOPOLOGY: linear ( i i ) MOLECULE TYPE: protein ( i i i ) HYPOTHETICAL: NO ( v i ) ORIGINAL SOURCE:
      ( A ) ORGANISM: Canis familiaris ( x i ) SEQUENCE DESCRIPTION: SEQ ID NO:51:

Met Lys Lys Thr Tyr Asp Leu Leu Phe Lys Leu Leu Leu Ile Gly Asp
1 5 10 15

Ser Gly Val Gly Lys Thr Cys Val Leu Phe Arg Phe Ser Asp Asp Ala
20 25 30

Phe Asn Thr Thr Phe Ile Ser Ile Gly Ile Asp Phe Lys Ile Lys Thr
35 40 45

Val Glu Leu Gln Gly Lys Lys Ile Lys Leu Gln Ile Trp Asp Thr Ala
50 55 60

Gly Gln Glu Arg Phe His Thr Ile Thr Thr Ser Tyr Tyr Arg Gly Ala
65 70 75 80

Met Gly Ile Met Leu Val Tyr Asp Ile Thr Asn Gly Lys Ser Phe Glu
85 90 95

Asn Ile Ser Lys Trp Leu Arg Asn Ile Asp Glu His Ala Asn Glu Asp
100 105 110

Val Glu Arg Met Leu Leu Gly Asn Lys Cys Asp Met Asp Asp Lys Arg
115 120 125

Val Val Pro Lys Gly Lys Gly Glu Gln Ile Ala Arg Glu His Gly Ile
130 135 140

Arg Phe Phe Glu Thr Ser Ala Lys Val Asn Ile Asn Ile Glu Lys Ala
145 150 155 160

```
            Phe    Leu    Thr    Leu    Ala    Glu    Asp    Ile    Leu    Arg    Lys    Thr    Pro    Val    Lys    Glu
                                        165                           170                            175

Pro    Asn    Ser    Glu    Asn    Val    Asp    Ile    Ser    Ser    Gly    Gly    Gly    Val    Thr    Gly
                                 180                           185                            190

Trp    Lys    Ser    Lys    Cys    Cys
                                 195
```

( 2 ) INFORMATION FOR SEQ ID NO:52:

( i ) SEQUENCE CHARACTERISTICS:
       ( A ) LENGTH: 214 amino acids
       ( B ) TYPE: amino acid
       ( C ) STRANDEDNESS: single
       ( D ) TOPOLOGY: linear ( i i ) MOLECULE TYPE: protein ( i i i ) HYPOTHETICAL: NO ( v i ) ORIGINAL SOURCE:
       ( A ) ORGANISM: Homo sapiens ( x i ) SEQUENCE DESCRIPTION: SEQ ID NO:52:

```
            Met    Gly    Thr    Arg    Asp    Asp    Glu    Tyr    Asp    Tyr    Leu    Phe    Lys    Val    Val    Leu
            1                           5                                  10                                  15

Ile    Gly    Asp    Ser    Gly    Val    Gly    Lys    Ser    Asn    Leu    Leu    Ser    Arg    Phe    Thr
                                 20                           25                                  30

Arg    Asn    Glu    Phe    Asn    Leu    Glu    Ser    Lys    Ser    Thr    Ile    Gly    Val    Glu    Phe
                          35                           40                                  45

Ala    Thr    Arg    Ser    Ile    Gln    Val    Asp    Gly    Lys    Thr    Ile    Lys    Ala    Gln    Ile
                   50                                  55                                  60

Trp    Asp    Thr    Ala    Gly    Gln    Glu    Arg    Tyr    Arg    Ala    Ile    Thr    Ser    Ala    Tyr
            65                                         70                           75                                  80

Tyr    Arg    Gly    Ala    Val    Gly    Ala    Leu    Leu    Val    Tyr    Asp    Ile    Ala    Lys    His
                                        85                           90                                  95

Leu    Thr    Tyr    Glu    Asn    Val    Glu    Arg    Trp    Leu    Lys    Glu    Leu    Arg    Asp    His
                                 100                          105                                 110

Ala    Asp    Ser    Asn    Ile    Val    Ile    Met    Leu    Val    Gly    Asn    Lys    Ser    Asp    Leu
                                 115                          120                          125

Arg    His    Leu    Arg    Ala    Val    Pro    Thr    Asp    Glu    Ala    Arg    Ala    Phe    Ala    Glu
                   130                          135                          140

Lys    Asn    Gly    Leu    Ser    Phe    Ile    Glu    Thr    Ser    Ala    Leu    Asp    Ser    Thr    Asn
            145                          150                          155                                 160

Val    Glu    Ala    Ala    Phe    Gln    Thr    Ile    Leu    Thr    Glu    Ile    Tyr    Arg    Ile    Val
                                        165                          170                          175

Ser    Gln    Lys    Gln    Met    Ser    Asp    Arg    Glu    Asn    Asp    Met    Ser    Pro    Ser    Asn
                                 180                          185                          190

Asn    Val    Val    Pro    Ile    His    Val    Pro    Pro    Thr    Thr    Glu    Lys    Pro    Lys    Val
                          195                          200                          205

Gln    Cys    Cys    Gln    Asn    Ile
                   210
```

PEPTIDES INHIBITING THE ONCOGENIC ACTION OF P21 RAS

FIELD OF THE INVENTION

This invention relates to peptides effective in inhibiting oncogenesis, particularly as related to inhibition of p21 ras and adenocarcinomas of the colon, pancreatic carcinomas, neuroblastomas, and other cancers which express the transformed sequence of the ras gene product.

BACKGROUND OF THE INVENTION ras protooncogenes are activated by characteristic point mutations in a wide variety of malignancies. The expressed p21 ras proteins are oncogenic by virtue of single substituted amino acids, usually at position 12 or 61 of the 189-residue p21 ras gene product. ras proteins act as membrane-associated molecular switches that bind GTP and GDP and slowly hydrolyze GTP to GDP.

Mutations in ras are associated with the vast majority of adenocarcinomas of the colon. Cancer of the colon is a highly treatable and often curable disease when it remains localized to the bowel. It is the second most frequently diagnosed malignancy in the United States as well as the second most common cause of cancer death. Surgery is the primary treatment and results in cure in approximately 50% of patients. Adenocarcinoma is the primary lesion in the majority of cases. Recurrence following surgery is a major problem and often is the ultimate cause of death. The prognosis for colon cancer patients is clearly related to the degree of penetration of the tumor through the bowel wall and the presence or absence of nodal involvement. For locally advanced disease, the role of radiation therapy in colon cancer is under clinical evaluation. There is no standard therapy for advanced colon cancer and no evidence that chemotherapy improves survival, although short-term palliation may be achieved in approximately 10–20% of patients.

Pancreatic carcinoma has a high incidence of K-ras mutations. Mutated K-ras sequences which can be identified by polymerase chain reaction utilizing allele-specific primers can even be found in the plasma or serum from patients with pancreatic carcinoma. The c-Ki-ras oncogene is activated by point mutations involving codon 12 in 72%–100% of primary pancreatic adenocarcinomas, but the gene is not activated in nonneoplastic tissues. Cancer of the exocrine pancreas is rarely curable. The highest cure rate (4%–12%) occurs if the tumor is truly localized to the pancreas. Unfortunately, this stage of disease accounts for fewer than 20% of cases and, even with surgical resection, results in little more than a 5% 5-year survival rate. For small cancers (less than 2 cm) in the head of the pancreas with no lymph node metastases and no extension beyond the "capsule" of the pancreas, the survival rate following resection of the head of the pancreas approaches 20%. Overall survival rate of all stages is less than 2% at 5 years with most patients dying within one year. Worldwide, very few patients with cancers of the pancreatic tail or uncinate process have been cured.

Lung cancers also frequently involve ras mutations. Point mutations in codon 12 of the K-ras protooncogene occur more frequently in lung adenocarcinomas from smokers (30%) than they do in lung adenocarcinomas from nonsmokers (7%), suggesting that smoking is an important factor in the induction of these mutations. The ras oncogene may thus be a specific target of the mutagenic activity of tobacco smoke, and suggest that DNA alterations at this site can occur early and irreversibly during the development of adenocarcinomas of the lung.

Mutations in the ras protooncogenes are the most frequently observed molecular alteration in acute myeloid leukemia (AML). Whether ras mutations occur as late or relatively early events in the multistep process of myeloid transformation, remains an open question. There is significant evidence that the ras oncogene plays a role in experimental mammary carcinogenesis; the evidence in human breast cancer, however, is more limited.

Similarly, there is significant evidence that the ras oncogene plays a role in nitrosoamine-induced esophageal tumors in rats, but in human esophageal cancers ras gene mutations are more rarely found. However, it is probable that there is a significant role of mutated ras genes in both cell proliferation and malignant transformation of human esophageal cells.

Certain human neuroblastomas also show a high incidence of oncogenic ras mutations. Indeed, one study suggested that expressions of the oncogene N-myc and p21 together as detected by immunohistochemical staining could be among the most reliable prognostic indicators in neuroblastoma patients.

The ras proteins are key regulators of the growth of eukaryotic cells. Some of the direct targets are unknown. These target proteins include raf-1, gap, phosphatidylinositol-3-hydroxykinase and, very recently, two nuclear proteins, C-JUN and its kinase (JNK). The three-dimensional x-ray crystal structure for a ras-related protein bound to a domain of raf-1 has been elucidated. The ras-related protein (rak-1-a) binds to raf directly, utilizing residues contained in a sequence involving amino acids 35–37. All of the contact residues in the ras-related protein are homologous to those in the corresponding segment of ras-p-21. One of the inventors has shown that the p-21 ras protein (35–47 segment) selectively inhibits the mitogenic effects of oncogenic ras-p-21.

In addition to its role as an oncogene, the activation of ras proteins is a key step in the signal transduction pathways triggered by ligand-bound cell surface receptors, such as the insulin receptor.

The classical target of the ras protein is the GTPase activating protein GAP. This target protein is thought to play an essential role in the regulation of ras activity by increasing the GTPase activity of wild type, but not transformed ras. On the other hand, there is a considerable superfamily of these GAP-related proteins, which includes p120-GAP. Other target proteins besides mammalian gap itself include (1) IRA1 and IRA2, the functional equivalents of GAP in yeast. They regulate the ras-cyclic AMP pathway, controlling cell growth; (2) sari, the fission yeast protein that regulates ras1 in that organism; (3) BUD2, a yeast protein that activates BUD1/RSR1 which participates in the regulation of bud-site selection; (4) Human neurofibromitosis (gene NF1). NF1 is associated with type 1 neurofibromatosis, one of the most frequently inherited genetic diseases characterized, in part, by multiple neural tumors. NF1 has been shown genetically and biochemically to interact with and stimulate the GTPase activity of ras; (5) Drosophila Gap1, which acts as a negative regulator of signalling by the Sevenless (SOS) receptor tyrosine kinase involved in eye development. Human SOS1 and SOS2 genes have also been recently identified which encode proteins that control GDP→GTP exchange on ras proteins and are involved in signal transduction by tyrosine kinase receptors. In situ hybridization shows that SOS1 maps to 2p22→p16 and SOS2 to 14q21→q22 in the human genome.

Another important target of ras is raf. The protein encoded by the c-raf-1 protooncogene is thought to function downstream of p21 ras because disruption of raf blocks signalling by ras in a number of systems. A highly-conserved 81 residue region of the N-terminus of raf protein has been to be shown to be critical as the ras protein interaction region. Importantly, the raf gene product interacts with both wild-type and activated ras protein. In one study, approximately 50% of the clones identified as interacting with ras were encoded portions of the c-raf and A-raf serine/threonine kinases. Thus, ras and the N-terminal region of raf protein associate directly in vitro and this interaction is dependent on GTP bound to ras.

Within the superfamily of ras-related GTP-binding proteins, only the ras protein itself has been shown to act as an oncogenic protein. Many other proteins, however, have substantial amino acid homology to ras. This ras superfamily of GTP-binding proteins (>50 members) regulates a diverse spectrum of intracellular processes. These include cellular proliferation and differentiation, intracellular vesicular trafficking, cytoskeletal control, NADPH oxidase function, as well as others. Some of these homologs may have biological activities which are related to ras. For example, rhoA encodes a ras-related GTP-binding protein that was thought principally to play a role in cytoskeletal organization. Recent evidence, however, has suggested both that rhoA could act either as a dominant oncogene, since transfection of both normal and activated rho genes confer a transformed phenotype on fibroblast cells in culture, or as a recessive tumor suppressor gene, by virtue, in part, of its chromosomal location at 3p21, a site deleted in many human malignancies. Thus, it is important to consider these ras homologs as potentially involved in cell growth and transformation.

Azatyrosine strongly inhibits oncogenic ras-p-21. This small molecule induces the rrg gene, which encodes a proteinase sequence showing 90% amino acid sequence identity to lysyl oxidase.

To acquire transforming potential, the precursor of the ras oncoprotein must undergo farnesylation or similar modification of the cysteine residue located in a carboxyl-terminal tetrapeptide. These C-terminal lipid modifications are essential for the interaction of ras-related proteins with membranes. While all ras proteins are farnesylated and some palmitoylated, the majority of other ras-related proteins are geranylgeranylated. Thus selective peptide and peptidomimetic inhibitors of ras lipidation have found potential utility as anti-oncogenic agents.

In view of the foregoing, there is there a longfelt need in the art for agents which inhibit the transforming ability of ras. As described above, selective peptide and peptidomimetic inhibitors or ras lipidation have found potential utility as anti-oncogenic agents (Kohl et al. (1993) Science 260:1934–1937; James et al. (1993) Science 260:1937–1942). Similarly, FR patents 2694296 and 2690162 teach that peptides derived from the GAP protein may serve to inhibit ras. However, neither '694296 nor '690162 describes peptides derived from the ras protein itself. EP 203587 describes new ras oncogene polypeptides which are used for producing antibodies for immunogenic assays. However, these sequences are derived from ras and its homologs in the carboxyl terminal domain (residues 170–189 in SEQ ID NO:5) and are thus physically distant from and completely unrelated to any sequences claimed herein. Furthermore, these sequences were claimed for the production of antibodies, preferably by linking to an immunogenic carrier, and a claim for direct therapeutic application was not made.

Thus, peptides constructed from ras and its homologs for therapeutic application, namely by interfering with downstream or upstream actions of ras itself, are useful. Furthermore, the method of identification of said peptides utilizing calculational approaches is believed novel and has unexpectedly led us to these cyclic peptides and peptidomimetics disclosed herein.

SUMMARY OF THE INVENTION

The present invention provides cyclized peptides and peptidomimetics capable of inhibiting the oncogenic action of p21 ras. The oncogenic ras-inhibiting cyclized peptides correspond to domains of the oncogenic ras protein which are most flexible and important in interacting with target proteins upstream and downstream from ras. The peptidomimetics are obtained by molecular modeling, including the structural minimization techniques of molecular dynamics. The peptides are designated by the formulas: Val-Val Ile, Lys-Arg-Val, Ile-Lys-Arg-Val-Lys-Asp (SEQ ID NO:1), Lys-Cys-Asp-Leu-Ala (SEQ ID NO:2), Cys-Asp-Leu-Ala-Ala-Arg-Thr (SEQ ID NO:3), Asp-Leu-Ala-Ala (SEQ ID NO:4) or physiologically acceptable salts of the foregoing peptides.

Also provided in the present invention are cyclic analogues of the above peptides and certain others, namely:

cyclo [-R(1) R(2) Thr Ile Glu Asp Ser Tyr Arg Lys Gln Val Val Ile Asp R(3) R(4)-] (I);

cyclo [-R(1) R(2) Val Val Ile R(3) R(4)-] (II);

cyclo [-R(1) R(2) Tyr Arg Glu Gln Ile Lys Arg Val Lys Asp Ser Asp Val Pro R(3) R(4)-] (III);

cyclo [-R(1) R(2) Lys Arg Val R(3) R(4)-] (IV);

cyclo [-R(1) R(2) Ile Lys Arg Val Lys Asp R(3) R(4)-] (V);

cyclo [-R(1) R(2) Gly Asn Lys Cys Asp Leu Ala Ala Arg Thr Val Glu R(3) R(4)-] (VI);

cyclo [-R(1) R(2) Lys Cys Asp Leu Ala R(3) R(4)-] (VII);

cyclo [-R(1) R(2) Cys Asp Leu Ala Ala Arg Thr R(3) R(4)] (VIII);

cyclo [-R(1) R(2) Asp Leu Ala Ala R(3) R(4)-] (IX); and

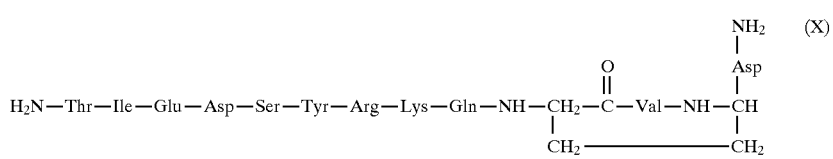

or physiologically acceptable salts thereof.

In cyclized peptide formulas (I)–(IX), R(1) R(2), R(3) and R(4) represent, in the most general case, any amino acid which can serve as an amino acid residue linker. Amino acid residue linkers are usually at least one residue and can be most often two to four residues, more often 1 to 10 residues, both ranges being inclusive. Typical amino acid residues useful for linking are tyrosine, cysteine, lysine, and glutamic and aspartic acid. Most preferably [R(1), R(2)] and [R(3), R(4)] are each independently selected from either the group consisting of Glu, Gln, Asp, Asn or from the group consisting of Lys, Arg, Orn.

The symbol — represents a bond between the carboxyl and amino termini by which R(1) and R(4) can be interconnected to each other via an lower alkenyl or lower alkynyl group, but most preferably by a branched or unbranched methylene bridge of type —(CH$_2$)$_m$— or —(CH$_2$)$_m$—M—(CH$_2$)$_{m'}$—. In such an moiety, m and m' are integers from 1 to 6, inclusive, and preferably from 1 to 3, inclusive; and M is NH, N[R(5)], O, S or CH—R(5), wherein R(5) is lower alkyl, cycloalkyl or aryl and is preferably methyl, ethyl, propyl, phenyl, X-phenyl, or heterocyclic, wherein X is Cl—, CF$_3$—, F—, substituted at the o-, m-, or p-positions on the phenyl group M can contain a part of another diamino acid within the same peptide, e.g., the omega amino group of the one residue can be so linked to such an unnatural amino acid residue in a terminal residue.

Furthermore, any amino acid in the sequences provided hereinabove may be replaced with its D-analogue, with the proviso that not more than 50% of the total amino acids are so replaced. Similarly, a homologous conservative substitution for any amino acid is within the bounds of the present invention provided that substitution does not eliminate the oncogenic ras p21-inhibiting activity. Thus, depending on the applications for which the peptides according to the invention are intended, it is also possible to envisage intercalating between several amino acids, or even between all the amino acids, of the peptides defined above, dextrorotatory amino acids, and in particular dextrorotatory phenylalanine or dextrorotatory tryptophan, capable of preventing the action of the degradative enzymes in the cell environment and thus of increasing their activity. Another modification in this sense consists in replacing certain amino acids, for example of the isoleucine type, by leucine.

In addition, a subject polypeptide can differ, unless otherwise specified, from the natural sequences shown above by the sequence being modified by terminal —NH$_2$ acylation, e.g., acetylation, or by terminal-carboxylamidation, e.g., with ammonia, alkylamines, and the like.

This invention further relates to peptidomimetics which model the critical semi-extended conformation, exemplified by the compounds of Structure 1:

Structure 1

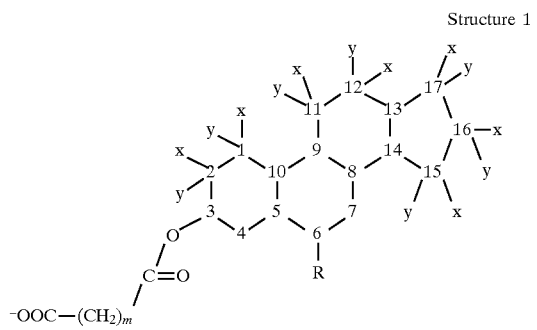

wherein the sidechain R attached at the carbon atom numbered 6 on the sterol nucleus can be NH—CH$_2$—CH$_2$NH$_{3+}$, alkyl amino, arylamino, or aralkylamino group, and wherein the sidechain attached at the carbon number 3 can be replaced with —O—C(=O)—(CH$_2$)$_m$—COOH, where m is an integer from 1 to 6, inclusive, preferably from 1 to 3, inclusive, and more preferably 2, and one of x and y at each position independently, can be one H, a small alkyl group of C$_1$ to C$_3$, preferably C$_1$; a halogen, preferably F, or an amino group where the other of one of x and y is H. Preferably, each of x and y is H.

Structure 2

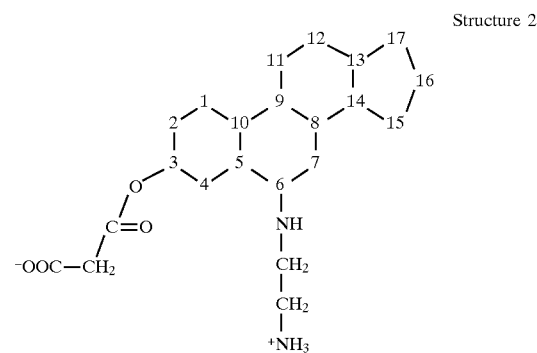

An exemplary compound falling within Structure 1 is 3 malonoxy-6-(2-aminoethyl) aminocyclopentanoperhydrophenanthrene (Structure 2).

DETAILED DESCRIPTION OF THE INVENTION

The natural sequence of the human oncogenic ras p21 is given in SEQ ID NO:5. The crystal X-ray structure has been determined at high resolution for that portion of the human ras protein corresponding to residues 1 to 166 of SEQ ID NO:5.

The regions of the p21 protein that are the most likely to change their conformations upon activation of the protein, e.g. by oncogenic amino acid substitutions have been computed using two different methods. Both methods are based on the principle that the linear sequence of amino acids in a protein determines its unique three-dimensional structure. Given an amino acid sequence of a polypeptide or protein, therefore, it should be possible to predict its three-dimensional structure. This task can be accomplished by using the principle that the observed three-dimensional structure of a protein is the one of lowest free energy. There are a vast number of possible structures a given polypeptide chain can adopt, but essentially only one of these is observed. To allow folding to occur, therefore, the interatomic interactions in the protein chain must greatly stabilize its final folded form, i.e., lower its conformational energy substantially with respect to that of any other competing structure. Thus, to compute the lowest energy form of a protein, it is necessary to be able first to compute the conformational energy of a given conformation of the protein and then, second, to generate its low energy conformations, or a representative sampling of them. The structure of lowest conformational energy so computed is then predicted to be the observed structure of the protein. This structure may be the one determined by x-ray crystallography or by 2- or 3-dimensional nuclear magnetic resonance (NMR) techniques.

A set of potential energy functions, in the computer program ECEPP (Empirical Conformational Energies of Peptides Program), have been developed that accurately compute the conformational energies of given conformations of proteins. The conformational energy of a peptide can be expressed in Equation 1.

$$E_{tot} = \sum_{i \neq j} \frac{Q_i Q_j}{DR_{ij}} + \sum_{i \neq j} \epsilon_{ij} \left( \left[ \frac{\rho_{ij}}{R_{ij}} \right]^{12} - \right.$$

-continued $$2\left[\frac{\rho_{ij}}{R_{ij}}\right]^6\right) + \sum_k \left(\frac{A_k}{2}\right)(1 \pm \cos(n\Theta_k))$$

where $E_{tot}$ is the total conformational energy of the protein, the Q's are the charges on the $i^{th}$ and $j^{th}$ atoms; $R_{ij}$ is the distance between the $i^{th}$ and $j^{th}$ atoms, D is the dielectric constant, $\in_{ij}$ and $\rho_{ij}$ are the lowest non-bonded (Lennard-Jones) energy and the distance at this lowest energy between atoms i and j in the protein; $A_k$ is the torsional barrier to rotation around specific bonds; $\theta_k$ is the $k^{th}$ dihedral angle in the protein; n is a degeneracy factor, i.e., 3 for single bonds and 2 for double bonds; and the sign in the last summation term is positive for single bonds and negative for double bonds such as occur in the peptide bond units.

This equation shows the total conformational energy as the sum of three terms: the pairwise electrostatic interactions between the individual atoms of a protein, each of which has a partial charge, (first sum); a non-bonded energy term (second term) that consists of an attractive term that varies as the inverse sixth power (tenth power for hydrogen-bonding atoms) of the distance between the atoms (from an induced dipole-induced dipole interaction term) and a repulsive term, from the overlap of electron shells, that varies as the inverse twelfth power of the interatomic distance; and finally a torsional term (third sum) that depends upon the bonds about which rotation takes place. All of the constants in these terms have been determined from experimental crystal packing data and reproduce the lattice constants of all of the crystal structures of small molecules to which they have been applied and, where measured, the sublimation energies of these crystals These potential functions have been used to compute the low energy minima for single terminally blocked amino acid residues, simple peptides, oligopeptides, polypeptides, and proteins with excellent agreement between the lowest energy predicted structures and the structures determined experimentally. These potentials have therefore been well-tested, are based on experimental data, and have proved to be reliable in prediction of structure from sequence.

These potential functions have been used to compute the average structure for the ras-p-21 protein in its normal and in its oncogenic form using the perturbation method called the electrostatically-driven Monte Carlo method (EDMC). Specific regions of the oncogenic p21 protein undergo large conformational changes compared with the structure of the normal, inactive protein. One of these regions has been found to be residues 35–47. All of the segments that change conformation in the oncogenic protein were found to be the most flexible in the normal, inactive protein.

Of considerable significance has been the finding that a completely different method, viz. molecular dynamics, based upon a completely different set of potential functions, i.e. the program DISCOVER, yields identical results for the p21 protein.

Molecular dynamics is based on the principle that the positions of the atoms of a molecule can be predicted as a function of time by solving Newton's equations of motion for the molecule. The force on the molecule is the negative of the first derivative of the potential function with respect to the coordinates of each of the atoms. Newton's equations of motion are then integrated, using the Verlet algorithm, over a trajectory such that the low energy regions around the starting structure are computed. The trajectories are computed over time intervals such that the total energy converges to a low, constant value. The structures whose energies have converged are then used to compute an average structure. Comparison of the coordinates of the atoms of this average structure with those of the starting structure reveals regions of the protein whose conformations may change significantly. Furthermore, if the variance of the coordinates of regions of the low energy structures from the corresponding coordinates of the average structure are high, these regions can be identified as being flexible, i.e., are the ones most likely to be parts of effector domains. Within this algorithm, for the p21 protein, up to 2000 water molecules have been generated around the protein in the molecular dynamics simulations performed thus far.

Using these novel calculational approaches, the present inventors have identified important peptide regions of the protein that are involved in the signal transduction process, and these peptides can be used to design anti-cancer agents, as taught herein. We have found that most particularly the 35–47, 96–110 and 115–126 peptides have strong and specific anti-oncogenic p21 activity. Even more particularly, we found that these domains contain unique extended structures and/or short beta-bend structures which are hypothesized to account in large part for their biological uniqueness. This suggested that cyclization of the peptide structures to force the beta-bend conformation in place would serve to enhance therapeutic activity.

The results of these studies indicate that a domain of particular interest is the domain from residues 35 through 47 of SEQ ID NO:5, i.e., Thr-Ile-Glu-Asp-Ser-Tyr-Arg-Lys-Gln-Val-Val-Ile-Asp (SEQ ID NO:6), of even more particular interest the peptide corresponding to residues 44 to 46 in SEQ ID NO:5, i.e., Val-Val-Ile, of still more interest is the sequence from residues 96 to 110 of SEQ ID NO:5, i.e., Tyr-Arg-Glu-Gln-Ile-Lys-Arg-Val-Lys-Asp-Ser-Asp-Asp-Val-Pro (SEQ ID NO:7), of even more particular interest is the sequence from residues 101–103 in SEQ ID NO:5, i.e., Lys-Arg-Val; and the sequence corresponding to residues 100 to 105 in SEQ ID NO:5, i.e., Ile-Lys-Arg-Val-Lys-Asp (SEQ ID NO:1); the sequence corresponding to residues 115 to 126 of SEQ ID NO:5, i.e., Gly-Asn-Lys-Cys-Asp-Leu-Ala-Ala-Arg-Thr-Val-Glu (SEQ ID NO:8); and most particularly the sequence corresponding to residues 117 to 121 of SEQ ID NO:5, i.e, Lys-Cys-Asp-Leu-Ala (SEQ ID NO:2) and the sequence corresponding to residues 118 to 124 of SEQ ID NO:5, i.e., Cys-Asp-Leu-Ala-Ala-Arg-Thr (SEQ ID NO:9); and the sequence corresponding to residues 119 to 122 of SEQ ID NO:5, i.e., Asp-Leu-Ala-Ala (SEQ ID NO:4).

Additional sequences homologous to the various preferred sequences recited hereinabove can be derived by one skilled in the art from the sequences of closely related ras proteins. Such sequences may possess enhanced therapeutic activity. Nonlimiting examples of such proteins closely related to the ras gene product which represent the parent sequences having identical or nearly identical three dimensional structures and from which homologs of the sequences given in the preceding paragraph can be derived by one normally skilled in the art are:

ras-related protein Ara-3 [*Arabidopsis thaliana* (mouse ear cress)] (SEQ ID NO:10);
ras-related protein Ara-2 [*A. thaliana*] SEQ ID NO:11;
ras-related protein Ara-1 [*A. thaliana*] SEQ ID NO:12;
ras-related protein OraB-1 [*Discopyge ommata* (electric ray)] SEQ ID NO:13;
ras-related protein Rab-1A [*Lymnea stagnalis* (great pond snail)] SEQ ID NO:14;
ras-related protein Rab-2 [*Homo sapiens* (human)] SEQ ID NO:15;
ras-related protein Rab-2 [*L. stagnalis*] SEQ ID NO:16;
ras-related protein Rab-2 [*Oryctolagus cuniculus* (rabbit)] SEQ ID NO:17;

ras-related protein Rab-2 [*Rattus norvegicus* (rat)] SEQ ID NO:18;
ras-related protein Rab-3 [*Drosophila melanogaster* (fruitfly)] SEQ ID NO:19;
ras-related protein Rab-4 [*R. norvegicus*] SEQ ID NO:20;
ras-related protein Rab-6 [*Caenorhabditis elegans*] SEQ ID NO:21;
ras-related protein Rab-6 [*H. sapiens*] SEQ ID NO:22;

cyclo [-R(1) R(2) GLY ASN LYS CYS ASP LEU ALA ALA ARG THR VAL GLU R(3) R(4)-] (VI)
cyclo [-R(1) R(2) LYS CYS ASP LEU ALA R(3) R(4)-] (VII)
cyclo [-R(1) R(2) CYS ASP LEU ALA ALA ARG THR R(3) R(4)-] (VIII)
cyclo [-R(1) R(2) ASP LEU ALA ALA R(3) R(4)-] (IX); and

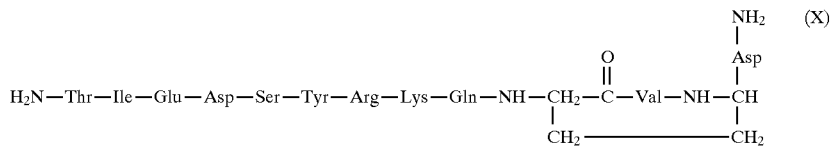

ras-related protein Rab-7 [*Canis familiaris* (dog)] SEQ ID NO:23;
ras-related protein Rab-7 [*Dictyostelium discoideum* (slime mold)] SEQ ID NO:24;
ras-related protein Rab-8 [*C. familiaris*] SEQ ID NO:25;
ras-related protein RabC [*D. discoideum*] SEQ ID NO:26;
ras-related protein Rac-1 [*C. elegans*] SEQ ID NO:27;
ras-related protein Rac-1A [*D. discoideum*] SEQ ID NO:28;
ras-related protein RacB [*D. discoideum*] SEQ ID NO:29;
ras-related protein RacC [*D. discoideum*] SEQ ID NO:30;
ras-related protein Ral-A [*H. sapiens*] SEQ ID NO:31;
ras-related protein Ral-B [*H. sapiens*] SEQ ID NO:32;
ras-related protein O-Ral [*D. ommata*] SEQ ID NO:33;
ras-related protein Ora-1 [*D. ommata*] SEQ ID NO:34;
ras-related protein Ora-2 [*D. ommata*] SEQ ID NO:35;
ras-related protein Ora-3 [*D. ommata*] SEQ ID NO:36;
ras-related protein Rap-1 [*D. discoideum*] SEQ ID NO:37;
ras-related protein Rap-2A [*H. sapiens*] SEQ ID NO:38;
ras-related protein Rap-2B [*H. sapiens*] SEQ ID NO:39;
ras-related protein O-KREV [*D. ommata*] SEQ ID NO:40;
ras-related protein Rap-1A [*H. sapiens*] SEQ ID NO:41;
ras-related protein Rap-1B [*H. sapiens*] SEQ ID NO:42;
ras-like protein GNROR3 [*D. melanogaster*] SEQ ID NO:43;
ras-like protein rasA [*D. discoideum*] SEQ ID NO:44;
ras-like protein rasB [*D. discoideum*] SEQ ID NO:45;
ras-like protein rasC [*D. discoideum*] SEQ ID NO:46;
ras-like protein rasG [*D. discoideum*] SEQ ID NO:47;
ras-like protein F54C8.5 [*C. elegans*] SEQ ID NO:48;
ras-like protein CC-ras [*Coprinus cinereus* (inky cap fungus)] SEQ ID NO:49;
ras-like protein [*Geodia cydonium* (sponge)] SEQ ID NO:50;
ras-related protein Rab-10 [*C. familiaris*] SEQ ID NO:51;
ras-related protein Rab-11 [*H. sapiens*] SEQ ID NO:52.

In addition, as described hereinabove, the therapeutic activity of these sequences is enhanced by cyclization. Cyclization forces and maintains the conformations of these peptides in unique structures like beta-bends. The following are representative, nonlimiting examples of cyclized peptides useful for inhibiting the oncogenic activity of the ras protein, said peptides having formulas as given below:

cyclo [-R(1) R(2) THR ILE GLU ASP SER TYR ARG LYS GLN VAL VAL ILE ASP R(3) R(4)-] (I)
cyclo [-R(1) R(2) VAL VAL ILE R(3) R(4)-] (II)
cyclo [-R(1) R(2) TYR ARG GLU GLN ILE LYS ARG VAL LYS ASP SER ASP ASP VAL PRO R(3) R(4)-] (III)
cyclo [-R(1) R(2) LYS ARG VAL R(3) R(4)-] (IV)
cyclo [-R(1) R(2) ILE LYS ARG VAL LYS ASP R(3) R(4)-] (V)

or a physiologically acceptable salt thereof.

In the aforementioned cyclized peptide formulas I–IX, R(1) R(2), R(3) and R(4) represent, in the most general case, any amino acid, such that they serve as amino acid residue linkers. Amino acid residue linkers are usually at least one residue and can be most often two to four residues, more often 1 to 10 residues. Typical amino acid residues used for linking are tyrosine, cysteine, lysine, glutamic and aspartic acid. Most preferably [R(1), R(2)] and [R(3), R(4)] independently are selected from either the groups [Glu, Gln, Asp, Asn] or [Lys, Arg, Orn].

The term — represents a bond between the carboxyl and amino termini by which R(1) and R(4) can be interconnected to each other via an lower alkyl, alkenyl or lower alkynyl group, but most preferably by a branched or unbranched methylene bridge of type $-(CH_2)_m-$ or $-(CH_2)_m-M-(CH_2)_{m'}-$. In such a moiety, m and m' are integers from 1 to 6, inclusive, and preferably from 1 to 3, inclusive; and M is NH, N[R(5)], O, S or CH—R(5), wherein R(5) is lower alkyl, cycloalkyl or aryl and is preferably methyl, ethyl, propyl, phenyl, X-phenyl, or heterocyclic, wherein X is Cl—, $CF_3$, F—, substituted at the o-, m-, or p- positions on the phenyl group. M can contain a part of another diamino acid within the same peptide, e.g., the omega amino group of the one residue can be so linked to such an unnatural amino acid residue in a terminal residue.

Furthermore, any amino acid in the cyclized peptide sequences (I)–(X) recited herein may be replaced with its D-analogue, insofar as not more than 50% of the total amino acids are so replaced. Similarly, a homologous conservative substitution for any amino acid is within the bounds of the present invention. Conservative substitutions include Glu for Asp, Gln for Asn and Val for Ile, among others, as well-known to the art. Depending on the applications for which the peptides according to the invention are intended, it is also possible to intercalate between several amino acids, or even between all the amino acids, of the peptides defined above, dextrorotatory amino acids, and in particular dextrorotatory phenylalanine or dextrorotatory tryptophan, capable of preventing the action of the degradative enzymes in the cell environment and thus of increasing their activity. Another modification in this sense consists in replacing certain amino acids, for example of the proline type, by D-tryptophan.

In addition, a subject polypeptide can differ, unless otherwise specified, from any of the natural sequences shown herein above by the sequence being modified by terminal $-NH_2$ acylation, e.g., acetylation, or by terminal-carboxylamidation, e.g., with ammonia, alkylamines, and the like.

The placement of hydrophobic amino acid residues is highly dependent on the peptide sequence. For example, for the 35–47 peptide sequence, corresponding to amino acids 35–47 of SEQ ID NO:5, there is a distinct hydrophobic region for the amino acid residues corresponding to amino acids 44–46 of SEQ ID NO:5. The bridge in Compound (X) occurs at what corresponds in structure to amino acids 44–46 in SEQ ID NO:5. It is possible to extend this hydrophobic segment without sacrificing activity. For example, the carboxyl terminal Asp residue can be replaced with one or more hydrophobic residues such as Val or Ile, and the result is greater efficiency in crossing cell membranes.

Short half-lives of peptides, a major problem, can be at least partially extended by the addition of D-amino acids to either or both of the amino and carboxyl terminal ends of the peptide. These D-amino acid residues block the action of exo-proteases that degrade peptides from their amino or carboxyl ends. In addition, the cyclization of the peptide further renders the peptide less susceptible to proteolysis.

Recent advances in the field of peptides have been directed towards the stabilization of these peptides against enzymatic or hydrolytic degradation. It would be extremely valuable to stabilize these peptides from degradation by proteolytic enzymes in order to improve their pharmacokinetic properties. Enhanced resistance to enzymatic degradation would increase the usefulness of these peptides as therapeutic agents. However, since they only exhibit short half lives in vivo, large amounts of such peptides must typically be administered to a subject in order to achieve the desired effect. Alternatively, smaller quantities may be prescribed to an individual, but more frequent dosages would be required to achieve the same level of potency.

It is further well-known to those normally skilled in the art that it is possible to replace peptides with peptidomimetics. Peptidomimetics are generally preferable as therapeutic agents to peptides owing to their enhanced bioavailability and relative lack of attack from proteolytic enzymes. The present inventors have used the techniques of molecular modeling supra to design a peptidomimetic which mimics the critical beta-bend aspects of the peptide corresponding in sequence to amino acids 96–110 of SEQ ID NO:5 (p21 ras). The bend structure occurs at amino acids 102–103 in the p21 ras protein. These residues have been implicated in the binding of ras p21 to SOS.

Peptidomimetric compounds which inhibit the oncogenic or transforming activity of the p21 ras protein are provided by the compounds of Structure I:

Structure 1

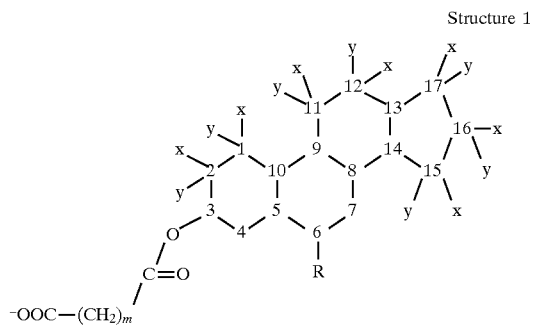

wherein the sidechain R attached at the carbon atom numbered 6 on the sterol nucleus can be NH—$CH_2$—$CH_2NH_3^+$, alkyl amino, arylamino, or aralkylamino group, and wherein the sidechain attached at the carbon number 3 can be replaced with —O—C(=O)—$(CH_2)_m$—COOH, where m is an integer from 1 to 6, inclusive, preferably from 1 to 3, inclusive, and more preferably 2, and one of x and y at each position independently, can be one H, a small alkyl group of $C_1$ to $C_3$, preferably $C_1$; a halogen, preferably F, or an amino group where the other of one of x and y is H. Preferably, each of x and y is H.

Without wishing to be bound by any particular theory, the structure believed to be the optimally designed ras-inhibiting peptidomimetic is illustrated below in Structure II:

Structure 2

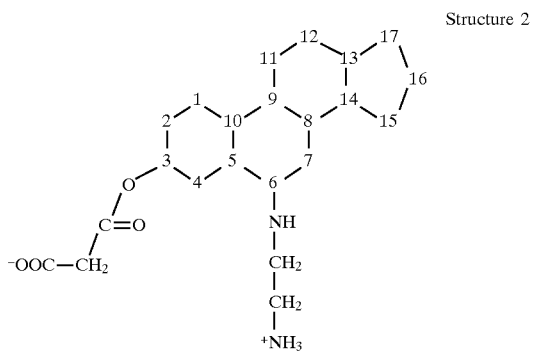

The instant invention comprises novel peptides of medicinal importance most particularly for the treatment of adenocarcinomas of the colon, pancreatic carcinomas, neuroblastomas, and other cancers of undefined germ cell origin which express the transformed sequence of the ras protein. These peptide sequences were unexpectedly obtained by the use of molecular dynamic simulations on ras p21 to define which domains of the protein were most flexible and were thus most important in interacting with target proteins upstream and downstream from ras. These peptides are identified by the following amino acid sequences: Thr-Ile-Glu-Asp-Ser-Tyr-Arg-Lys-Gln-Val-Val-Ile-Asp (SEQ ID NO:6), Val-Val-Ile, Tyr-Arg-Glu-Gln-Ile-Lys-Arg-Val-Lys-Asp-Ser-Asp-Asp-Val-Pro (SEQ ID NO:7), Lys-Arg-Val, Ile-Lys-Arg-Val-Lys-Asp (SEQ ID NO:1), Gly-Asn-Lys-Cys-Asp-Leu-Ala-Ala-Arg-Thr-Val-Glu (SEQ ID NO:8), Lys-Cys-Asp-Leu-Ala (SEQ ID NO:2), Cys-Asp-Leu-Ala-Ala-Arg-Thr (SEQ ID NO:9), and Asp-Leu-Ala-Ala (SEQ ID NO:4).

Including the cyclic analogues of the above peptides, namely:

cyclo [-R(1) R(2) Thr-Ile-Glu-Asp-Ser-Tyr-Arg-Lys-Gln-Val-Val-Ile- Asp-R(3) R(4)-] (I);

cyclo [-R(1) R(2) Val-Val-Ile-R(3) R(4)-] (II);

cyclo [-R(1) R(2) Tyr-Arg-Glu-Gln-Ile-Lys-Arg-Val-Lys-Asp-Ser-Asp-Asp-Val-Pro-R(3) R(4)-] (III);

cyclo [-R(1) R(2) Lys-Arg-Val R(3) R(4)-] (IV);

cyclo [-R(1) R(2) Ile-Lys-Arg-Val-Lys-Asp R(3) R(4)-] (V);

cyclo [-R(1) R(2) Gly-Asn-Lys-Cys-Asp-Leu-Ala-Ala-Arg-Thr-Val-Glu R(3) R(4)-] (VI);

cyclo [-R(1) R(2) Lys-Cys-Asp-Leu-Ala R(3) R(4)-] (VII);

cyclo [-R(1) R(2) Cys-Asp-Leu-Ala-Ala-Arg-Thr R(3) R(4) -] (VIII);

cyclo [-R(1) R(2) Asp-Leu-Ala-Ala R(3) R(4)-] Z (IX); and

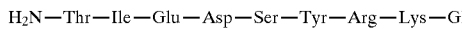
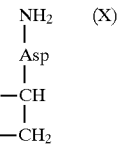

or a physiologically acceptable salt thereof.

Wherein for cyclized peptide formulas designated by (I)–(IX) hereinabove, R(1) R(2), R(3) and R(4) represent, in the most general case, any amino acid, such that they serve as amino acid residue linkers. Amino acid residue linkers are usually at least one residue and can be most often two to four residues, more often 1 to 10 residues. Typical amino acid residues used for linking are tyrosine, cysteine, lysine, glutamic and aspartic acid, or the like. Most preferably [R(1), R(2)] and [R(3), R(4)] independently are selected from either the groups [Glu, Gln, Asp, Asn] or [Lys, Arg, Orn].

The symbol — represents a bond between the carboxyl and amino termini by which R(1) and R(4) can be interconnected to each other via an lower alkenyl or lower alkynyl group, but most preferably by a branched or unbranched methylene bridge of type —$(CH_2)_m$— or —$(CH_2)_m$—M—$(CH_2)_{m'}$—. In such an moiety, m and m' are integers from 1 to 6 and preferably from 1 to 3; and M is NH, N[R(5)], O, S CH—R(5) or does not exist, wherein R(5) is lower alkyl, cycloalkyl or aryl and is preferably methyl, ethyl, propyl, phenyl, X-phenyl, or heterocyclic, wherein X is Cl—, $CF_3$—, F—, substituted at the o-, m-, or p- positions on the phenyl. M can contain a part of another diamino acid within the same peptide, e.g., the omega amino group of the one residue can be so linked to such an unnatural amino acid residue in a terminal residue.

Furthermore, any amino acid in the sequences provided may be replaced with its D-analogue, insofar as not more than 50% of the total amino acids are so replaced. Conservative substitutions include Glu for Asp, Gln for Asn and Val for Ile, among others, as is well known to those of ordinary skill in the art. Similarly, a homologous conservative substitution for any amino acid is within the bounds of the present invention. Depending on the applications for which the peptides according to the invention are intended, it is also possible to envisage intercalating between several amino acids, or even between all the amino acids, of the peptides defined above, dextrorotatory amino acids, and in particular dextrorotatory phenylalanine or dextrorotatory tryptophan, capable of preventing the action of the degradative enzymes in the cell environment and thus of increasing their activity. Another modification in this sense consists in replacing certain amino acids, for example of the proline type, by D-tryptophan.

In addition, a subject polypeptide can differ, unless otherwise specified, from the natural sequences shown above by the sequence being modified by terminal —$NH_2$ acylation, e.g., acetylation, or by terminal-carboxylamidation, e.g., with ammonia, alkylamines, and the like.

The instant invention also comprises a method of use of the peptides supra for the treatment of adenocarcinomas of the colon, pancreatic carcinomas, neuroblastomas, and other cancers of undefined germ cell origin which express the transformed sequence of the ras protein.

It is also an object of the present invention to provide peptides and cyclized peptide homologs from the sequences listed in SEQ ID NOS:10–52.

The amino acid residues described herein are preferred to be in the "L" isomeric form. However, residues in the "D"isomeric form can be substituted for any L-amino acid residue, as long as the desired functional property is retained by the polypeptide. $NH_2$ refers to the free amino group present at the amino terminus of a polypeptide. COOH refers to the free carboxyl group present at the carboxy terminus of a polypeptide. In keeping with standard polypeptide nomenclature described in J. Biol. Chem. 243:3552–3559 (1969) and adopted at 37 C.F.R. 1.822(b) (2)), The list of variable amino acids, capable of participating in the composition of this peptide is as follows: Y, Tyr, tyrosine; G, Gly, glycine; F, Phe, phenylalanine; M, Met, methionine; A, Ala, alanine; S, Ser, serine; I, Ile, isoleucine; L, Leu, leucine; T, Thr, threonine; V, Val, valine; P, Pro, proline; K, Lys, lysine; H, His, histidine; Q, Gln, glutamine; E, Glu, glutamic acid; W, Trp, tryptophan; R, Arg, arginine; D, Asp, aspartic acid; N, Asn, asparagine; C, Cys, cysteine.

Amino acid residue sequences are presented herein in the conventional left-to-right direction of amino-terminus to carboxy-terminus. In addition, the phrase "amino acid residue" is broadly defined to include the amino acids listed hereinabove, and modified and unusual amino acids, such as those listed in 37 C.F.R. 1.822(b) (4), incorporated herein by reference. Furthermore, it should be noted that a dash at the beginning or end of an amino acid residue sequence indicates either a peptide bond to a further sequence of one or more amino acid residues or a covalent bond to an amino or hydroxyl end group.

Polypeptide and peptide are terms used interchangeably herein to designate a linear series of amino acid residues connected one to the other by peptide bonds between the alpha-amino and carboxy groups of adjacent residues.

Protein is a term used herein to designate a linear series of greater than about 20 amino acid residues connected one to the other as in a polypeptide.

The term synthetic peptide refers to a chemically produced chain of amino acid residues linked together by peptide bonds that is free of naturally occurring proteins and fragments thereof. The term peptide encompasses linear and cyclic peptides.

(D,L), (D), or (L) preceding the amino acid designation means that this amino acids exists in that specific isomeric form, i.e. (D,L) Phe means that the amino acid phenylalanine exists as a racemic mixture; (D) Phe or D-Phe means that the amino acid phenylalanine exists as the D-stereoisomer or implied R configuration; (L) Phe means that the amino acid phenylalanine exists as the L stereoisomer or implied S configuration.

Alkyl as used herein means methyl, ethyl, n-propyl, isopropyl, n-butyl, sec-butyl, isobutyl, tert-butyl, n-pentyl, neopentyl, 2-methylbutyl, 1-methylbutyl, 1-ethylpropyl, 1,1-dimethylpropyl, n-hexyl, 1-methylpentyl, 2-methylpentyl, 3-methylpentyl, 4-methylpentyl, 3,3-dimethylbutyl, 2,2-dimethylbutyl, 1,1-dimethylbutyl, 2-ethylbutyl, 1-ethylbutyl, 1,3-dimethylbutyl, n-heptyl, 5-methylhexyl, 4-methylhexyl, 3-methylhexyl, 2-methylhexyl, 1-methylhexyl, 3-ethylpentyl, 2-ethylpentyl, 1-ethylpentyl, 4,4-dimethylpentyl, 3,3-dimethylpentyl, 2,2-dimethylpentyl, 1,1-dimethylpentyl, n-octyl, 6-methylheptyl, 5-methylheptyl, 4-methylheptyl, 3-methylheptyl, 2-methylheptyl, 1-methylheptyl, 1-ethylhexyl, 1-propylpentyl, 3-ethylhexyl, 5,5-dimethylhexyl, 4,4-dimethylhexyl, 2,2-diethylbutyl, 3,3-diethylbutyl, 1-methyl-1-propylbutyl.

Cycloalkyl refers to a hydrocarbon ring having from 3 to 7 carbon atoms, inclusive. Examples of cycloalkyl groups are cyclopropyl, cyclopentyl, cycloheptyl, cyclooctyl, cyclononyl, and the like.

The term aryl refers to aromatic groups which have at least one ring having a conjugated pi electron system and includes carbocyclic aryl, heterocyclic aryl aralkyl, and biaryl groups, all of which may be optionally substituted.

Heterocyclic groups means groups having from 1 to 3 heteroatoms as ring atoms in the aromatic ring and the remainder of the ring atoms carbon atoms. Suitable heteroatoms include oxygen, sulfur, and nitrogen, and their heterocyclic compounds can include furanyl, thienyl, pyridyl, pyrrolyl, N-lower alkyl pyrrolo, pyrimidyl, pyrazinyl, imidazolyl, and the like, all optionally substituted.

Substituted heterocyclic refers to any heterocyclic aryl group substituted by a alkyl, aryl, cycloalkyl, halo, sulfonate, or trifluoromethyl group.

The term alkyl amino refers to the groups —NRR' wherein respectively, (a) R is alkyl and R' is hydrogen or alkyl; (b) R is aryl and R' is hydrogen or aryl, (c) R is cycloalkyl and R' is hydrogen or alkyl, (d) R is hydrogen and R' is itself linear aminoalkyl, (e) R is alkyl and R' is itself linear aminoalkyl.

The term aminoalkyl refers to the groups —(CH$_2$)$_m$—NRR', wherein m is an integer from 1 to 6, inclusive and —NRR' is alkyl amino, as defined supra.

Halo encompasses fluoro, chloro, bromo and iodo.

The phrase protecting group, as used herein, means substituents which protect the reactive functional group from undesirable chemical reactions. Examples of such protecting groups include esters of carboxylic acids, ethers of alcohols and acetals and ketals of aldehydes and ketones.

The phrase N-protecting group or N-protected as used herein means those groups intended to protect the N-terminus of an amino acid or peptide, to protect an amino group against undesirable reactions during synthetic procedures and includes, but is not limited to, sulfonyl, acetyl, pivaloyl, t-butyloxycarbonyl (Boc), carbonylbenzyloxy (Cbz), benzoyl and an L- or D-aminoacyl residue, which may itself be N-protected similarly. The deprotection conditions for the above protecting groups necessarily vary with the choice of protecting group. Thus, for example, an acyl group such as an alkanoyl, alkoxycarbonyl or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid such as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-charcoal.

The phrase COOH-protecting group or carboxyl-protecting group is, an esterifying group, for example an alkyl group (especially methyl or ethyl) or an arylmethyl group (especially benzyl). The deprotection conditions for the above protecting groups necessarily vary with the choice of protecting group. Thus, for example, an esterifying group such as an alkyl or arylmethyl group may be removed, for example, by hydrolysis with a suitable base such as an alkali metal hydroxide, for example lithium or sodium hydroxide. Alternatively an esterifying group such as an arylmethyl group may be removed, for example, by hydrogenation over a catalyst such as palladium-on-charcoal using either hydrogen or ammonium formate as a hydrogen source by methods well-known to those skilled in the art.

Electrolyte means a solution that has sufficient acid strength to render a basic starting material essentially protonated.

Chemical derivative refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-imidazolyl-benzylhistidine. Also included as chemical derivatives are those peptides which contain one or more naturally occurring amino acid derivatives of the twenty standard amino acids. For examples, 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions or residues relative to the sequence of a polypeptide whose sequence is shown herein, so long as the requisite activity is maintained.

As used herein, fragment means any subject peptide or polypeptide having an amino acid residue sequence shorter than that of a peptide or polypeptide whose full length amino acid residue sequence is shown herein.

A pharmaceutically acceptable salt is one which is prepared by contacting a compound of formulas (I)–(X) according to the specifications therein with an acid whose anion is generally considered suitable for human consumption. Examples of pharmacologically acceptable acid addition salts include the hydrochloride, hydrobromide, hydroiodide, sulfate, phosphate, acetate, propionate, lactate, maleate, malate, succinate, and tartrate salts. All of these salts may be prepared by conventional means by reacting, for example, the appropriate acid with the corresponding compound of structure of Formulas (I)–(X).

Unless otherwise indicated, the preparation methods disclosed herein result in product distributions which include all possible structural isomers. It is understood that physiological response may vary according to stereochemical structure. The isomers may be separated by conventional means such as fractional crystallization or High Pressure Liquid Chromatography (HPLC). Briefly, the absolute configuration of a compound relates to how its substituents are oriented in space about a central atom. This notion becomes significant when coupled with the rigors of chirality. Chirality involves the identity of the substituents about that central atom. Thus, in general, a compound is said to be chiral when four distinctly different groups are bound to a central carbon atom. These groups may be spatially aligned in more than one manner without repeating their individual orientations. That is, a chiral compound may exhibit a mirror image which is also chiral. These mirror images are termed meso configurations, and are each absolute configurations of a chiral compound.

Pharmaceutical compositions according to the present invention comprise a peptides and peptidomimetics of the invention in association with a pharmaceutically acceptable carrier or excipient, adapted for use in human or veterinary medicine. The compositions may contain from 0.001–99% of the active material. Such compositions may be presented for use in conventional manner in admixture with one or more physiologically acceptable carriers of excipients. The pharmaceutical compositions according to the invention may also contain other active ingredients such as antimicrobial agents, or preservatives. The compositions may optionally further contain one or more other therapeutic agents which may, if desired, be a chemotherapeutic antiviral agent.

Pharmaceutically acceptable salts of the peptides of this invention may be formed conventionally by reaction with an appropriate acid. The addition salts so formed from addition by acid may be identified by hydrochloric, hydrobromic, phosphoric, acetic, fumaric, salicylic, citric, lactic, mandelic, tartaric, oxalic, methanesulfonic, and the like.

Thus, the peptides and peptidomimetics according to the present invention may be formulated for oral, buccal, parenteral, topical or rectal administration. In particular, these peptides and peptidomimetics may be formulated for injection or for infusion and may be presented in unit dose form in ampoules or in multidose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form for constitution with a suitable vehicle, e.g. sterile, pyrogen-free water, before use.

The present invention further provides a process for preparing a pharmaceutical composition which comprises bringing a peptide or peptidomimetic of the invention into association with a pharmaceutically acceptable excipient or carrier.

For administration by injection or infusion, the daily dosage as employed for treatment of an adult human of approximately 70 kg body weight will range from 0.01 mg to 10 mg, preferably 0.1 to 5 mg, which may be administered in 1 to 4 doses, for example, depending on the route of administration and the condition of the patient. The dosage of the peptide used in the treatment will vary, depending on the seriousness of the disorder, the weight of the patient, the relative efficacy of the peptide and the judgment of the treating physician. However, suitable unit dosages in humans may be between about 0.05 mg to about 100 mg. For example, a unit dosage may be from between about 0.2 mg to about 50 mg. Such a unit dosage, described hereinabove, may be administered more than once a day, e g., two or three times a day. Thus, the total daily dosage is in the range of about 0.01 mg to 10 mg/kg. Such therapy may extend for several weeks, in an intermittent or uninterrupted manner, until the patient's symptoms are eliminated.

The present invention also provides pharmaceutical compositions which comprise a pharmaceutically effective amount of the peptides of this invention, or pharmaceutically acceptable salts thereof, and, preferably, a pharmaceutically acceptable carrier or adjuvant. Therapeutic methods of this invention comprise the step of treating patients in a pharmaceutically acceptable manner with those peptides or compositions. Such compositions may be in the form of tablets, capsules, caplets, powders, granules, lozenges, suppositories, reconstitutable powders, or liquid preparations, such as oral or sterile parenteral solutions or suspensions.

In order to obtain consistency of administration, it is preferred that a composition of the invention is in the form of a unit dose. The unit dose presentation forms for oral administration may be tablets and capsules and may contain conventional expedients. For example binding agents, such as acacia, gelatin, sorbitol, or polyvinylpyrrolidone; fillers, such as lactose, sugar, maize-starch, calcium phosphate, sorbitol or glycine; tabletting lubricants such as magnesium stearate; disintegrants, such as starch, polyvinylpyrrolidone, sodium starch glycolate or microcrystalline cellulose; or pharmaceutically acceptable wetting agents such as sodium lauryl sulfate.

The solid oral compositions may be prepared by conventional methods of blending, filling, tabletting, or the like. Repeated blending operations may be used to distribute the active agent throughout those compositions employing large quantities of fillers. Such operations are, of course, conventional in the art. The tablets may be coated according to methods well-known in normal pharmaceutical practice, in particular with an enteric coating.

Oral liquid preparations may be in the form of emulsions, syrups, or elixirs, or may be presented as a dry product for reconstitution with water or other suitable vehicle before use. Such liquid preparations may or may not contain conventional additives. For example suspending agents, such as sorbitol, syrup, methyl cellulose, gelatin, hydroxyethylcellulose, carboxymethylcellulose, aluminum stearate gel, or hydrogenated edible fats; emulsifying agents, such as sorbitan monooleate or acacia; non-aqueous vehicles (which may include edible oils), such as almond oil, fractionated coconut oil, oily esters selected from the group consisting of glycerine, propylene glycol, ethylene glycol, and ethyl alcohol; preservatives, for instance methyl para-hydroxybenzoate, ethyl para-hydroxybenzoate, n-propyl parahydroxybenzoate, or n-butyl parahydroxybenzoate or sorbic acid; and, if desired, conventional flavoring or coloring agents.

For parenteral administration, fluid unit dosage forms may be prepared by utilizing the peptide and a sterile vehicle, and, depending on the concentration employed, may be either suspended or dissolved in the vehicle. In preparing solutions, the peptides of this invention may be dissolved in water, whereas opiates used heretofore showed only marginal solubility in aqueous media or physiological fluids. Once in solution, the peptide may be injected and filter sterilized before filling a suitable vial or ampoule and subsequently sealing the carrier or storage package. Adjuvants, such as a local anaesthetic, a preservative or a buffering agent, may be dissolved in the vehicle prior to use. Stability of the pharmaceutical composition may be enhanced by freezing the composition after filling the vial and removing the water under vacuum, e.g., freeze drying the composition. Parenteral suspensions may be prepared in substantially the same manner, except that the peptide should be suspended in the vehicle rather than being dissolved. A surfactant or wetting solution may be advantageously included in the composition to facilitate uniform distribution of the peptide.

The stability of the peptides of the present invention exceeds that of naturally occurring peptides if substitution is made with D-amino acids in at least 20%, but not more than 50%, of those residues which are naturally present in the (L) configuration. Without being bound by theory, we believe that the increased resistance to enzymatic degradation over of the peptides of the present invention as compared to natural peptides is due to the presence of D-amino acids in the peptides. This switch from L to D amino acids neutralizes the digestion capabilities of many of the ubiquitous peptidases found in the digestive tract. Alternatively, the enhanced stability of the peptides of this invention may also be the result of the introduction of modifications of traditional peptide linkages. For example, the introduction of a cyclic ring within the peptide backbone may confer enhanced stability in order to circumvent the effect of many proteolytic enzymes known to digest small peptides in the stomach or other digestive organs and in serum.

The compounds of the present invention are initially synthesized by either solution or by solid phase techniques. Specific exemplary syntheses are described in the examples hereinbelow. The peptides of this invention may be prepared by initially reacting a first appropriately protected amino acid with a second appropriately protected amino acid in an organic solvent inert to the reactants, in the presence of a suitable peptide coupling agent according to the following scheme:

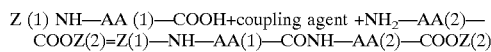

wherein Z(1) is a suitable nitrogen protecting group and Z(2) is a suitable carboxyl protecting group and AA represents any natural or unnatural amino acid residue. The desired peptides may be prepared by utilizing the appropriate amino acids and repeating this reaction sequence as required until a peptide with three to ten amino acid residues has been prepared. A suitable deprotection method is then employed to remove specified or all of the remaining protecting groups or the peptide from the resin.

The first appropriately protected amino acid and, for instance, an appropriately protected tyrosine may be reacted together in the presence of a suitable peptide coupling agent in a suitably inert organic solvent with stirring, shaking, or agitation to form a protected tyrosine containing dipeptide. Introducing this dipeptide to appropriate protecting group removal conditions affords a selectively deprotected dipeptide which is well-suited for continued peptide synthesis. Contacting this mono-deprotected tyrosine containing dipeptide with an appropriately protected amino acid having a side chain represented as above, in the presence of a suitable peptide coupling agent in a suitably inert organic solvent with stirring, shaking, or agitation forms a protected tyrosine containing tripeptide. This method may be repeated as many times as necessary to achieve the desired peptide.

The method of preparation for peptide synthesis requires specific functional groups to react with other substituents to link amino acid residues in a desired manner to form a peptide possessing a known and desired sequence of amino acid residues. Since amino acids possess at least two reactive functional groups, suitable protection, blocking, or masking of these groups is required to ensure that reaction will occur only at specifically desired sites.

These protecting groups should be introduced to the moiety efficaciously while their removal should be performed under conditions which do not affect other portions of the molecule. In this manner, certain reactions and modifications may be performed on the amino acid, peptide, or other compound, with assurance that the protected functionality will not interfere with the desired reaction. Further, by choosing a protecting group that is sensitive and labile to certain reactive conditions, a reaction scheme may be outlined to advantageously utilize these characteristics to effectively remove the protecting group once the synthesis is complete.

Both N-protecting groups and COOH-protecting groups (see definitions) may be used within the scope of this invention. A variety of protecting groups known in the field of peptide synthesis and recognized by conventional abbreviations therein, may be found in T. Greene, *Protective Groups In Organic Synthesis*, Academic Press (1981). Among the preferred protecting groups that may be utilized for suitable protection of reactive nucleophilic substituents include, for example, benzyl (Bz), carbobenzyloxy (Cbz), t-butoxycarbonyl (Boc), or 9-fluorenylmethyloxy-carbonyl (Fmoc).

Coupling of amino acids, which may be the same or different as those described above, to yield small peptides in route to peptides comprised of greater numbers of amino acid residues may be accomplished by employing established techniques in the field of peptide chemistry. A broad range of suitable reactions are described in E. Gross and J. Meinhofer, *The Peptides: Analysis, Synthesis, Biology; Modern Techniques of Peptide and Amino Acid Analysis*, John Wiley & Sons, (1981) and M. Bodanszky, *Principles Of Peptide Synthesis*, Springer-Verlag (1984). The peptide coupling agents which may be used to assist condensation of amino and carboxylic acid moieties include N,N'-dicyclohexylcarbodiimide (DCC), N,N'-carbonyl diimidazole (CDI), 1-hydroxy benzotriazole (HOBt), ethyl chloroformate, benzyl chloroformate, 1-(ethoxycarbonyl)-2-ethoxy-1,2-dihydroquinoline (EEDQ), benzotriazoyl-oxytris-(dimethyl)amino-phosphonium hexafluoro phosphate (BOP) and the like. A preferred technique uses DCC as the coupling reagent. The DCC method may be used with or without catalytic additives such as 4-dimethylaminopyridine (DMAP), copper (II) chloride or HOBt to hasten the reaction and suppress the racemization of the desired compound.

The DCC reaction is often performed at room temperature but may be carried out from about −78° C. to gentle reflux in a variety of solvents that are inert with respect to the reactants. The solvents are normally organic solvents which are polar and aprotic. Preferred solvents include, for example, dichloromethane, chloroform, diethyl ether, tetrahydrofuran (THF), N,N'-dimethylformamide (DMF), and the like. Particularly preferred solvents are dichloromethane and DMF. In general, the coupling reaction may be carried out at atmospheric pressure a temperature of −78° C. to reflux for a period of between 1 and 48 hours. Preferably, the reaction is carried out at about −10° C. to 25° C. with stirring, shaking or agitation, over a period of between 4 and 6 hours.

Alternatively, synthesis may be achieved prepared using solid phase synthesis, such as that described by Merrifield, J Am. Chem. Soc., 85, p 2149 (1964), although other equivalent chemical syntheses known in the art can also be used. Solid-phase synthesis is commenced from the C-terminus of the peptide by coupling a protected alpha-amino acid to a suitable resin as generally set forth in U.S. Pat. No. 4,244,946.

As an example, Ile protected by BOC is coupled to the a BHA resin using methylene chloride and dimethylformamide. Following the coupling of BOC-Ile to the resin support, the alpha-amino protecting group is removed, as by using trifluoroacetic acid (TFA) in methylene chloride, TFA alone or with HCl in dioxane. Preferably 50 volume % TFA in methylene chloride is used with 0–5 weight % 1,2 ethanedithiol. The deprotection is carried out at a temperature between about 0° C. and room temperature. Other standard cleaving reagents and conditions for removal of specific alpha-amino protecting groups may be used as described in Schroder & Lubke, *The Peptides*, pp 72–75 (Academic Press 1965).

After removal of the alpha-amino protecting group of Ile, the remaining alpha-amino- and side chain-protected amino acids are coupled step-wise in the desired order to obtain the intermediate compound defined hereinbefore. As an alternative to adding each amino acid separately in the synthesis, some of them may be coupled to one another prior to addition to the solid phase reactor. The selection of an appropriate coupling reagent is within the skill of the art. Particularly suitable as coupling reagents are N,N'-dicyclohexyl carbodiimide (DCC) and N,N'-diisopropyl carbodiimide (DICI), or N-ethyl-N'-(3-dimethylaminopropyl) carbodiimide. Other activating reagents and their use in peptide coupling are described by Schroder & Lubke, supra, in Chapter III and by Kapoor (1970) J. Phar. Sci. 59:127.

Each protected amino acid or amino acid sequence is introduced into the solid phase reactor in about a fourfold excess, and the coupling is carried out in a medium of dimethylformamide: dichloromethane (1:1) or in DMF or dichloromethane alone. In instances where the coupling is carried out manually, the success of the coupling reaction at each stage of the synthesis is monitored by the ninhydrin reaction, as described by E. Kaiser et al. (1970) Anal. Biochem. 34:595. In cases where incomplete coupling occurs, the coupling procedure is repeated before removal of the alpha-amino protecting group prior to the coupling of the next amino acid. The coupling reactions can be performed automatically, as on a Applied Biosystems automatic synthesizer.

After the desired amino acid sequence has been completed, the intermediate peptide is removed from the resin support by treatment with a reagent, such as liquid hydrogen fluoride, which not only cleaves the peptide from the resin but also cleaves all remaining side chain protecting groups and the alpha-amino protecting group (unless it is an acyl group which is intended to be present in the final peptide) to obtain the peptide. When using hydrogen fluoride for cleaving, anisole or cresol and methylethyl sulfide are included in the reaction vessel as scavengers. When Met is present in the sequence, the BOC protecting group may be cleaved with trifluoroacetic acid (TFA)/ethanedithiol prior to cleaving the peptide from the resin to eliminate potential S-alkylation.

All patents and publications referred to in the examples, and throughout the specification, are incorporated herein by reference, without admission that such is prior art.

The following nonlimiting examples are provided to illustrate the invention. The skilled artisan will recognize that there may be substitutions and variations of the exemplified methods which are apparent and can be practiced without departing from the essence of the invention.

EXAMPLES

Example 1

Peptide Synthesis

The synthesis of the peptide of SEQ ID NO:1 (Thr-Ile-Glu-Asp-Ser-Tyr-Arg-Lys-Gln-Val-Val-Ile-Asp) is conducted in a stepwise manner on a MBHA hydrochloride resin, such as available from Bachem, Inc. (Torrance, Calif.) having a substitution range of about 0.1 to 0.5 mmoles/gm. resin.

All equipment employed in the examples is commercially available. Unless otherwise indicated, all starting materials employed in the examples are commercially available. Sources for these materials include Sigma Chemical Co. (St. Louis, Mo.), Aldrich Chemical Co. (Milwaukee, Wis.), Lancaster Synthesis (Windham, N.H.), Fisher Scientific (Pittsburgh, Pa.), Boehringer Mannheim Biochemicals (Indianapolis, Ind.), Fluka Chemical Corp. (Ronkonkoma, N.Y.) and Chemical Dynamics Corp. (South Plainfield, N.J.). Most of the starting materials were obtained from Aldrich Chemical Co. (Milwaukee, Wis.).

All solvents used in the peptide preparations described herein, e.g. methylene chloride dichloromethane, 2-propanol, dimethylformamide (DMF), and methanol, were Burdick and Jackson "distilled in glass" grade and used without additional distillation. Trifluoroacetic acid (TFA), diisopropylethylamine (DIPEA), piperidine (PIP), dicyclohexylcarbodiimide (DCC), 1-hydroxybenzotriazole (HOBt), and [benzotriazole-1-yl-oxy-tris (dimethyl) phosphonium hexafluorophosphate] (BOP) were purchased from Chemical Dynamics Corp. and were "sequenal" grade purity. 1,2-ethanedithiol (EDT) was purchased from Sigma Chemical Co. and used without further purification. All protected amino acids were of the L-configuration unless otherwise indicated and were obtained from Bachem (Torrance, Calif.).

The synthesis is performed on an Applied Biosystems peptide synthesizer (Foster City, Calif.) using a suitable program, preferably as follows:

| STEP | REAGENTS AND OPERATIONS | MIX TIMES |
|---|---|---|
| 1 | Dichloromethane-80 ml. | 2 |
| 2 | Methanol(MeOH) wash-30 ml. | 2 |
| 3 | Dichloromethane-80 ml. | 3 |
| 4 | 50 percent TFA plus 5 percent 1,2-ethane- dithiol in dichloromethane-70 ml. | 2 |
| 5 | Isopropanol wash-80 ml. | 2 |
| 6 | TEA 12.5 percent in dichloromethane-70 ml. | 2 |
| 7 | MeOH wash-40 ml. | 2 |
| 8 | Dichloromethane wash-80 ml. | 3 |
| 9 | Boc-amino acid (10 mmoles) in 30 ml. of either DMF or dichloromethane, depending upon the solubility of the particular protected amino acid, (1 time) plus DCC (10 mmoles) in dichloromethane (reaction time 20–200 min) | |

Note: All wash and mix times three minutes except where noted.

Coupling of BOC-ASP(OBz) results in the substitution of about 0.35 mmol ASP per gram of resin. All solvents that are used are carefully degassed, preferably by sparging with an inert gas, e.g., helium or nitrogen, to insure the absence of oxygen.

After deprotection and neutralization, the peptide chain is built stepwise on the resin. Generally, one to two mmol. of BOC-protected amino acid in methylene chloride is used per gram of resin, plus one equivalent of 2M DCC in methylene chloride, for two hours. When BOC-Arg(Tos) is being coupled, a mixture of 50% DMF and methylene chloride is used. Bzl is used as the hydroxyl side-chain protecting group for Ser and Thr. p-nitrophenyl ester(ONp) can be used to activate the carboxyl end of Asn or Gln; for example, BOC-Asn(ONp) can be coupled overnight using one equivalent of HOBt in a 50% mixture of DMF and methylene chloride. The amido group of Asn or Gln is protected by Xan when DCC coupling is used instead of the active ester method. 2-Cl-CBZ is used as the protecting group for the Lys side chain. Tos is used to protect the guanidine group of Arg and the imidazole group of His, and the side-chain carboxyl group of Glu or Asp is protected by OBzl.

To cleave and deprotect the resulting protected peptide-resin, it is treated with 1.5 ml anisole, 0.5 ml of methylethylsulfide and 15 ml liquid hydrogen fluoride (HF) per gram of peptide-resin, first at −20° C. for 20 min and then at 0° C. for 30 min. This reaction must be performed with great care owing to the highly toxic and corrosive nature of hydrogen fluoride. This reaction is performed in a commercially available teflon apparatus (Peninsula Research, Inc., Richmond, Calif). After complete elimination of HF under high vacuum using a KOH trap, the resin-peptide is washed alternately with dry diethyl ether and chloroform, and the peptides are then extracted with degassed 2N aqueous acetic acid and separated from the resin by filtration on a Hirsch funnel.

The peptide is purified by gel permeation followed by preparative HPLC as described in Marki et al.(1981) J. Am. Chem. Soc. 103:3178; Rivier, et al. (1984) J. Chromatography 288:303–328; and Hoeger, et al. (1987) BioChromatography 2:134–142. The chromatographic fractions are carefully monitored by HPLC (see below), and only the fractions showing substantial purity are pooled.

To confirm that the desired sequence is achieved, the peptide is hydrolyzed in sealed evacuated tubes containing constant boiling HCl, 3 μl of thioglycol/ml and 1 nmol of Nle (as an internal standard) for 9 hours at 140° C. Amino acid analysis of the hydrolysates using a Beckman 121 amino acid analyzer to determine amino acid ratios allows confirmation that the desired peptide structure has been obtained.

Example 2

Cyclization of Active Peptides

Cyclization "traps" the bioactive conformation of the peptide by making the active conformation part of a ring system that allows it much less conformational flexibility. In this procedure, aspartate or glutamate residues are introduced into the sequence either in place of non-essential amino acid residues or as added residues in the chain. The new peptide is then subjected to electro-oxidation in which the two residues are decarboxylated, in an intramolecular Kolbe electro-oxidative coupling reaction, resulting in the joining of their respective —CH$_2$ groups, forming a ring as shown in FIG. 1. This method has been used to make a cyclized β-bend of the dipeptide, Pro-Gly, by placing a glutamic acid residue on the amino and carboxyl ends of this dipeptide and then performing the Kolbe electro-oxidation to form the tetra-(CH$_2$)-bridge. The Pro-Gly peptide, which has a variety of conformations in solution, when cyclized, was found to adopt the β-bend structure uniquely (Joran, A., "Conformationally restricted biologically active peptides, methods for their production and uses thereof," U.S. Pat. No. 5,364,851.) This method has been used quite recently to synthesize cyclized forms of the peptide vasopressin; these forms have been tested in an in vitro adenylate cyclase system and have been found to have prolonged half-lives and greater activity than the native peptide. Therefore, this cyclization procedure may result in enhanced peptide inhibition and in increased half-life. Introduction of the cyclizing rigidifying agent reduces the flexibility of the peptide and concurrently introduces non-polar aliphatic groups into the peptide (such as the tetra-methylene bridge shown in Scheme I) that help promote transport of the peptide through the cell membrane.

SCHEME I

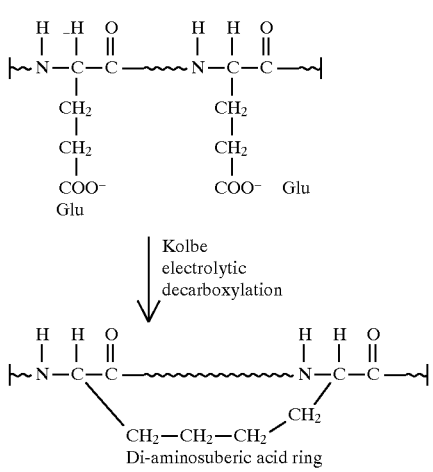

Scheme I illustrates an exemplary result of using electrolytic decarboxylation to cyclize peptides to trap them in their active conformations. Either two glutamate, two aspartate, or one glutamate and one aspartate residues are introduced in the chain represented by the wavy line. Under electro-oxidation shown here for two glutamate residues, a tetramethylene bridge forms cyclizing the region of the peptide that is to be held fixed in its bioactive conformation. The two connected residues shown constitute the diamino suberic acid moiety.

It should be noted that, in the synthesis of this new peptide, there are possibly other aspartate and glutamate amino acid residues that can undergo the oxidative decarboxylation. To prevent these reactions from occurring, these Asp and Glu residues are protected as esters during the solid phase synthesis of the peptide. The free Glu residues at positions 44 and 46 are then allowed to undergo the cyclization reaction, after which the protected acid groups are then deprotected.

This cyclization procedure can be performed on other regions of this peptide and on the other two active peptides.

The electrooxidative coupling reaction used to prepare the cyclic peptides of the invention can be performed in a divided or an undivided cell such as a standard glass H-cell, as described in Organic Electrochemistry (2nd Ed.), M. Baizer and H. Lund, eds., Marcel Dekker, New York, 1983, Chap. 5, p 168. For large scale runs, the reaction can be carried out in a plate and frame flow cell as described in Technique of Electroorganic Synthesis, Part III, N. Weinberg and B. Tilak, ed., John Wiley & Sons, New York, 1982, Chap. III, p 179.

Cathode materials useful for the preparation of the compounds of the invention include, but are not limited to, high hydrogen overvoltage materials such as mercury, lead or cadmium. Anode materials include, but are not limited to, materials such as mercury, lead, graphite, or graphite paste, which are stable under electrolysis conditions.

The electrooxidative coupling can occur in aqueous, or aqueous organic electrolytes, comprising solutions of Bronsted acids, such as sulfuric, fluoroboric, and trifluoroacetic acids. Any electrolyte may be selected that has sufficient acid strength to render a basic starting material protonated. A dilute solution of trifluoroacetic acid is most preferred.

Although the preferred method of electrolysis to obtain the compounds of this invention takes place under constant current conditions, the oxidative coupling could also be performed using controlled potential electrolysis, as understood by those skilled in the art. Typical current densities are between 1 and 5000 milliamps(mA)/cm$^2$, preferably between 10 and 100 mA/cm$^2$. The reaction is preferably carried out at a temperature in the range of about 0° C. to 37° C., more preferably about 10° C.

A standard glass H-cell (200 ml volume, glass frit separator) was equipped with a mercury pool cathode 12 cm$^2$ area), a magnetic stirrer, and a platinum foil anode. The cell reservoir was filled with 40 mM trifluoroacetic acid (110 ml) and placed in a water bath maintained at 10° C. The catholyte was purged with nitrogen. The starting peptide (20 mg) was added to the catholyte and constant current electrolysis was initiated at 0.1 A. The reaction progress was followed by HPLC and after passage of 1,060 coulombs, all the substrate had been consumed and the electrolysis was terminated. The catholyte was recovered and adjusted to pH 8 with NaOH. The pH-adjusted catholyte was extracted with chloroform (2 times 70 ml). The extract was freeze dried and the resultant powdery material extracted with acetonitrile (HPLC grade). This was filtered through a sintered-glass filter (fine porosity) and was reduced in volume on a rotary evaporator using a mechanical vacuum pump to a volume of 2 ml. This material was purified by reversed-phase high pressure liquid chromatography using a Waters HPLC system with a 0.46×0.25 cm column packed with 5 μm C$_{18}$ silica, 300 A pore size. Buffer A is an aqueous 0.1% (vol/vol) trifluoroacetic acid solution (1.0 ml of TFA per 1000 Ml solution); Buffer B is 100% acetonitrile. The determination is run at room temperature with a gradient from 15.5% Buffer B to 75%. Buffer B over a 30 min. The flow rate is 2.2 ml per minute, and the retention time is 25.0 min.

The structure was confirmed by 300 MHz $^1$H NMR, $^{13}$C NMR, and electrospray mass spectroscopy.

The amounts of the reactants and the conditions required to facilitate reaction and encourage efficient completion of the aforementioned Examples may vary widely. However, in general, the amounts of material employed to induce reaction in the processes discussed above will be substantially stoichiometric, unless otherwise specified. In the following examples, reaction concentrations are generally held at 0.1M for the reactants, unless a higher concentration or dilution would be particularly useful for influencing the direction of a specific reaction. In practice, the amounts used will depend upon variations in reaction conditions and the nature of the reactants as readily apparent to one of ordinary skill in the art.

In any of the methods described hereinabove, the desired products may be isolated from the reaction mixture by crystallization. Alternatively, chromatographic techniques including, but not limited to, normal phase, reverse phase, ion-exchange, affinity, or gel permeation, may be employed, as well as electrophoresis or extraction or other means.

Example 3

Oocyte Maturation Assay

Using the method described in Chung et al. (1991) Anticancer Res. 11:1373–1378, test peptides, cyclized peptides and/or peptidomimetics are injected into immature oocytes at various doses. The oocytes are co-injected with recombinant transforming ras p21 obtained from the National Cancer Institute of Japan. Alternatively, the oncogenic ras p21 can be prepared by the ordinary skilled artisan without the expense of undue experimentation as described in Chung et al. (1991) supra and in Chung et al. (1992) *Exp. Cell. Res. 203:329–335* The maturation of the oocytes is evaluated microscopically at low power (20×), using a Nikon Diaphot microscope, for example. Percent inhibition is calculated based on comparisons with oocytes which are injected with 0.05 mg/ml oncogenic ras p21.

The following results were obtained using a dose of each peptide equivalent to an internal oocyte concentration of 50 nM:

| Peptide OR | Sequence ID Number | Present Inhibition of ras-Induced Maturation |
|---|---|---|
|  | 6 | 28 |
| Val—Val—Ile |  | 34 |
|  | 7 | 56 |
| Lys—Arg—Val |  | 22 |
|  | 1 | 76 |
|  | 8 | 92 |
|  | 2 | 38 |
|  | 9 | 65 |
|  | 4 | 22 |

The peptidomimetics and cyclic peptides of the present invention will be similarly effective in inhibiting oocyte maturation in response to the oncogenic ras p21 protein, and in inhibiting oncogenesis.

Example 4

Synthesis of Peptidomimetic p21 ras Inhibitor

A 3β-O-carboxyalkyl-6α-N-(aminoethyl)amino steroid can be synthesized according to Scheme II. For reference to 6-ketosteroid oximes and their Na/EthOH reduction to 6α-amines (conversion of Structure I to Structure II), see Defaye and Fetizon (1969), *Bull. Soc. Chem. Fr.*, pp. 1632; Shoppee et al. (1957) *J. Chem. Soc.* 103; and Barnett et al. (1946) *J. Chem. Soc.* 524–530. The conversion of the 6α-amines to the 1,4-dialkylamines, see Coleman and Cullen (1946) J. Am. Chem. Soc. 68:2006, and alternate methods reviewed therein. For the conversion of Structure III to Structure IV (1,4- dialkylethylenediamine), see Coleman and Cullen (1946) *J. Am. Chem. Soc.* 68:2206; alternate methods are reviewed therein.

Alternative aminations and aminoethylations can be carried out as shown in Scheme III. The borohydride reduction of cholesterol is described in Wolfe et al. (1959) J. Org. Chem. 24:1034, and the second reaction is described in Tamura et al. (1974) *Synthesis*, pp. 196. The palladium-catalyzed reduction is as described in Freifelder, M., *Practical Catalytic Hydrogenation*.

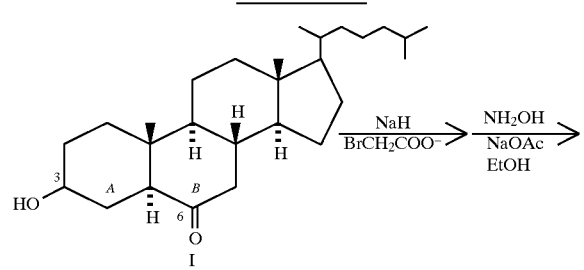

SCHEME II

SCHEME II -continued
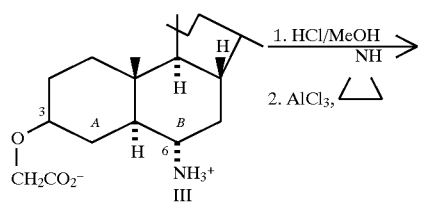
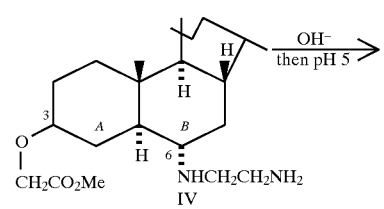
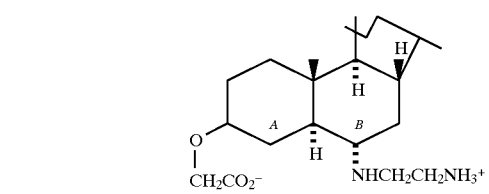
SCHEME III
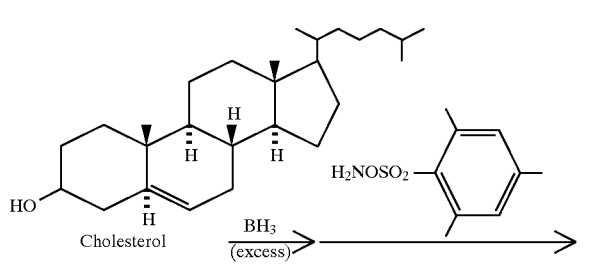
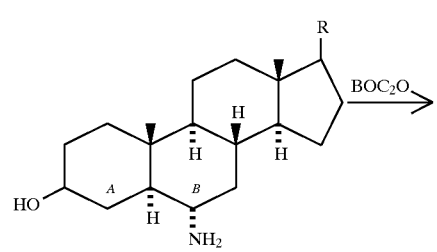
SCHEME III -continued
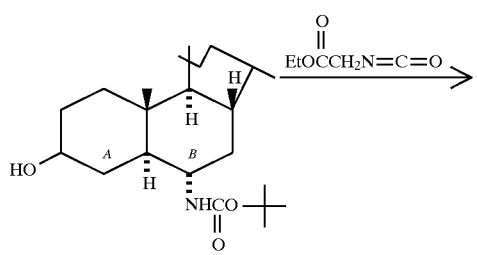
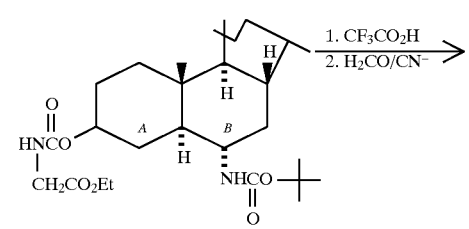
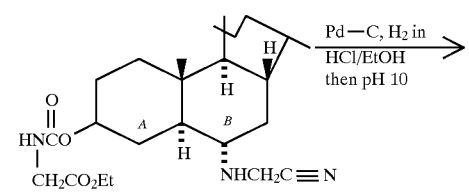
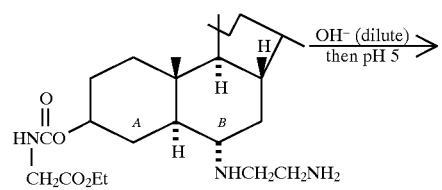
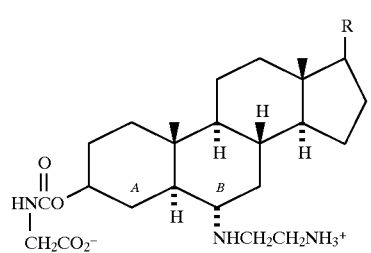

We claim:

1. A peptide having an amino acid sequence Val-Val-Ile or a physiologically acceptable salt thereof.

2. A cyclic peptide having a formula selected from the group consisting of cyclo {-R(1) R(2) Thr-Ile-Glu-Asp-Ser-Tyr-Arg-Lys-Gln-Val-Val-Ile-Asp R(3) R(4)-}, cyclo {-R(1) R(2) Val-Val-Ile R(3) R(4)-}, cyclo {-R(1) R(2) Tyr-Arg-Glu-Gln-Ile-Lys-Arg-Val-Lys-Asp-Ser-Asp-Asp-Val-Pro R(3) R(4)-}, cyclo {-R(1) R(2) Lys-Arg-Val R(3) R(4)-}, cyclo {-R(1) R(2) Ile-Lys-Arg-Val-Lys-Asp R(3) R(4)-}, cyclo {-R(1) R(2) Gly-Asn-Lys-Cys-Asp-Leu-Ala-Ala-Arg-Thr-Val-Glu R(3) R(4)-}, cyclo {-R(1) R(2) Lys-Cys-Asp-Leu-Ala R(3) R(4)-],} cyclo {-R(1) R(2) Cys-Asp-Leu-Ala-Ala-Arg-Thr R(3) R(4)-}, cyclo {-R(1) R(2) Asp-Leu-Ala-Ala R(3) R(4)-}, cyclo {-R(1) R(2) D-Thr-Ile-Glu-Asp-Ser-Tyr-Arg-Lys-Gln-Val-D-Val-Ile-Asp R(3) R(4)-}, cyclo {-R(1) R(2) D-Val-D-Val-D-Ile R(3) R(4)-}, cyclo {-R(1) R(2) D-Tyr-Arg-Glu-Gln-Ile-Lys-Arg-Val-Lys-Asp-D-Ser-Asp-D-Asp-Val Pro R(3) R(4)-}, cyclo {-R(1) R(2) D-Lys-D-Arg-D-Val-R(3) R(4)-}, cyclo {-R(1) R(2) D-Ile-Lys-Arg-Val-Lys-D-Asp-R(3) R(4)-}, cyclo {-R(1) R(2) Gly-D-Asn-Lys-Cys-Asp-Leu-D-Ala-Ala-Arg-Thr-D-Val-Glu R(3) R(4)-}, cyclo {-R(1) R(2) D-Lys-Cys-Asp-Leu-D-Ala R(3) R(4)-}, cyclo {-R(1) R(2) Cys-Asp-Leu-Ala-Ala-Arg-D-Thr R(3) R(4)-}, cyclo {-R(1) R(2) Asp-D-Leu-D-Ala-D-Ala R(3) R(4)-}, and wherein R(1) R(2), R(3) and R(4) represent independently alanine, ornithine, cysteine, lysine, glutamic and aspartic acid, and wherein there is a covalent bond between the carboxyl and amino termini by which R(1) and R(4) are interconnected to each other via a methylene bridge which is $—(CH_2)_m—$ or $—(CH_2)_m—M—(CH_2)_{m'}—$, wherein m and m' are integers from 1, 2, 3, or 4, and M is NH, N[R(5)], O, or S, and wherein R(5) is methyl, ethyl, n-propyl, isopropyl, cyclopropyl, or cyclobutyl, or the sidechain of any naturally occurring amino acid, and a physiologically acceptable salt thereof.

3. The cyclic peptide of claim 2 wherein said peptide has a structure which is

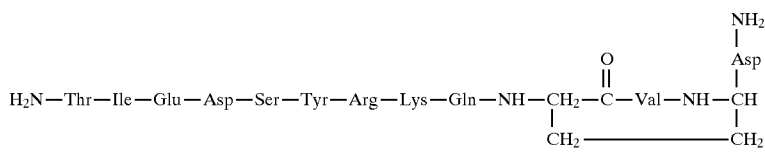

or a pharmaceutically acceptable salt thereof.

4. A pharmaceutical composition comprising an amount effective for the inhibition of the transforming or oncogenic activity of p21 ras of the peptide of claim 1 in a pharmaceutically acceptable carrier.

5. A pharmaceutical composition comprising an amount effective for the inhibition of the transforming or oncogenic activity of p21 ras of at least one cyclic peptide of claim 2 in a pharmaceutically acceptable carrier.

6. The pharmaceutical composition of claim 5, wherein said cyclic peptide has a structure

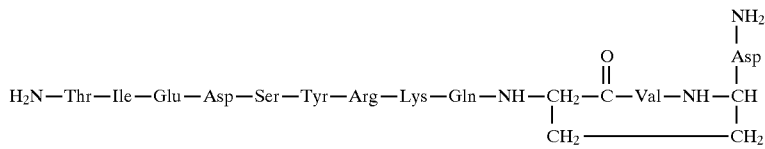

7. A pharmaceutical composition comprising an effective amount of at least one peptide of claim 2 in combination with the peptide of claim 1 with a pharmaceutically acceptable carrier.

8. A method for inhibiting the oncogenic or transforming activity of p21 ras, said method comprising the step of administering an effective amount of the peptide of claim 1, with the result that the transforming and/or oncogenic activity of the p21 ras protein is inhibited.

9. A method for inhibiting the oncogenic or transforming activity of p21 ras, said method comprising the step of

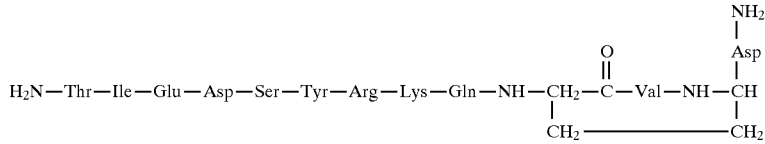

administering an effective amount of at least one cyclized peptide of claim 2, with the result that the transforming and/or oncogenic activity of the p21 ras protein is inhibited.

10. The method of claim 9 wherein the cyclic peptide has a structure

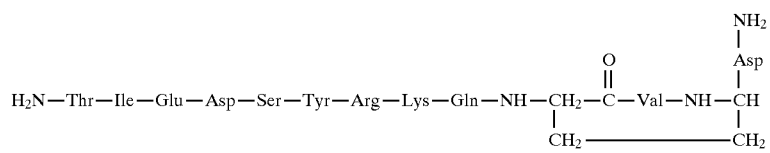
* * * * *

UNITED STATES PATENT AND TRADEMARK OFFICE
CERTIFICATE OF CORRECTION

PATENT NO.   : 5,840,683

DATED        : November 24, 1998

INVENTOR(S)  : Hlavka et al.

It is certified that error appears in the above-identified patent and that said Letters Patent is hereby corrected as shown below:

Title page , under "Other Publications", in column two, under "Spatola et al." please rewrite "Dekkea 1953)" as --Dekker 1983--.

Signed and Sealed this

Ninth Day of March, 1999

Attest:

Q. TODD DICKINSON

Attesting Officer

Acting Commissioner of Patents and Trademarks